US010144784B2

(12) United States Patent
Jin et al.

(10) Patent No.: US 10,144,784 B2
(45) Date of Patent: Dec. 4, 2018

(54) MONOCLONAL ANTIBODIES AGAINST ANTITHROMBIN BETA

(71) Applicant: Bayer Healthcare LLC, Whippany, NJ (US)

(72) Inventors: Ye Jin, San Ramon, CA (US); John E. Murphy, Boston, MA (US); Terry Hermiston, Mill Valley, CA (US); Timothy Myles, Sunnyvale, CA (US); Frank Dittmer, Duesseldorf (DE); Michael Strerath, Düesseldorf (DE); Uwe Gritzan, Cologne (DE)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 15/908,705

(22) Filed: Feb. 28, 2018

(65) Prior Publication Data

US 2018/0244799 A1 Aug. 30, 2018

Related U.S. Application Data

(63) Continuation of application No. 14/770,222, filed as application No. PCT/US2014/029541 on Mar. 14, 2014, now Pat. No. 9,908,942.

(60) Provisional application No. 61/784,590, filed on Mar. 14, 2013.

(51) Int. Cl.

| | |
|---|---|
| *A61K 39/395* | (2006.01) |
| *C07K 16/36* | (2006.01) |
| *A61K 38/48* | (2006.01) |
| *A61K 45/06* | (2006.01) |
| *C07K 16/18* | (2006.01) |
| *C07K 16/38* | (2006.01) |

(52) U.S. Cl.
CPC .......... *C07K 16/36* (2013.01); *A61K 38/4846* (2013.01); *A61K 45/06* (2013.01); *C07K 16/18* (2013.01); *C07K 16/38* (2013.01); *C07K 2317/21* (2013.01); *C07K 2317/32* (2013.01); *C07K 2317/33* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel et al. | |
| 5,179,017 A | 1/1993 | Axel et al. | |
| 5,530,101 A | 6/1996 | Queen et al. | |
| 5,753,445 A | 5/1998 | Fillit et al. | |
| 5,891,647 A | 4/1999 | Lormeau et al. | |
| 7,482,139 B2 | 1/2009 | Bock et al. | |
| 7,541,441 B2 | 6/2009 | Rosen et al. | |
| 7,722,873 B2 | 5/2010 | Lonberg et al. | |
| 7,767,401 B2 | 8/2010 | Lescuyer et al. | |
| 8,101,394 B2 | 1/2012 | Novokhatny | |
| 8,143,385 B2 | 3/2012 | Valge-Archer et al. | |
| 9,593,166 B2 | 3/2017 | Jin et al. | |
| 9,908,942 B2 * | 3/2018 | Jin | A61K 45/06 |
| 2009/0226429 A1 | 9/2009 | Salcedo et al. | |
| 2011/0081361 A1 | 4/2011 | Carter et al. | |
| 2011/0229476 A1 | 9/2011 | Liu et al. | |
| 2011/0311550 A1 | 12/2011 | Law et al. | |
| 2012/0027686 A1 | 2/2012 | Sexton et al. | |
| 2012/0027780 A1 | 2/2012 | Van et al. | |
| 2012/0121606 A1 | 5/2012 | Ruben et al. | |

FOREIGN PATENT DOCUMENTS

| | | |
|---|---|---|
| BE | 896543 A1 | 8/1983 |
| EP | 0391433 A2 | 10/1990 |
| EP | 0669344 A2 | 8/1995 |
| EP | 1382615 A1 | 1/2004 |
| EP | 0912728 B1 | 7/2008 |
| EP | 2525812 A2 | 11/2012 |
| EP | 1597381 B2 | 5/2013 |
| EP | 2088201 B1 | 5/2013 |
| ES | 2346618 A1 | 10/2010 |
| JP | S5578253 A | 6/1980 |
| JP | S62138187 A | 6/1987 |
| JP | H0266458 A | 3/1990 |
| JP | H0694713 A | 4/1994 |
| JP | 2001321167 A | 11/2001 |
| JP | 2002316999 A | 10/2002 |
| JP | 2006516085 A | 6/2006 |
| JP | 3841364 B2 | 11/2006 |
| JP | 2007523650 A | 8/2007 |

(Continued)

OTHER PUBLICATIONS

Chuang et al,, J Biol Chem. May 4, 2001;276(18):14961-71. Epub Feb. 7, 2001.*
Alnylam Pharmaceuticals Press Release, "Ainylam Presents New Pre-clinical Data on RNAi Therapeutics for the Treatment of Hemophilia and Other Bleeding Disorders at 54th American Society of Hematology (ASH) Annual Meeting", Dec. 2012.
Asakura; et al., "Preparation and Characterization of Monolconal Antibodies Against the Human Thrombinantithrombin III Complex", Biochimica et Biophysica Acta, 1988, vol. 952, 37-47.
Bjork; et al., "Conversion of Antithrombin from an Inhibitor of Thrombin to a Substrate with Reduced Heparin Affinity and Enhanced Conformational Stability by Binding of a Tetradecapeptide Corresponding to the P-1 to P-14 Region ofthe Putative Reactive Bond Loop ofthe Inhibitor", Journal of Biological Chemistry, Jan. 20, 1992, vol. 267 No. 3, 1976-1982.

(Continued)

*Primary Examiner* — Michael Szperka
(74) *Attorney, Agent, or Firm* — Timothy H. Joyce

(57) ABSTRACT

This patent document relates to antibodies, antigen-binding antibody fragments (Fabs), and other protein scaffolds, directed against human antithrombin β complexed with heparin and/or heparin-like structure (ATβH). These ATβH binding proteins can block the anti-coagulant activity of ATβ to induce coagulation. Therapeutic uses of these antibodies and binders are described herein as are methods of panning and screening specific antibodies.

18 Claims, 26 Drawing Sheets

Specification includes a Sequence Listing.

(56) References Cited

FOREIGN PATENT DOCUMENTS

| | | |
|---|---|---|
| JP | 4829609 B2 | 12/2011 |
| RU | 2262109 C2 | 10/2005 |
| WO | 9945962 A1 | 9/1999 |
| WO | 0069256 A1 | 11/2000 |
| WO | 0202641 A1 | 1/2002 |
| WO | 2004023973 A2 | 3/2004 |
| WO | 2005016236 A2 | 2/2005 |
| WO | 2005047331 A2 | 5/2005 |
| WO | 2005091805 A2 | 10/2005 |
| WO | 2006017538 A2 | 2/2006 |
| WO | 2006084050 A2 | 8/2006 |
| WO | 2009013251 A1 | 1/2009 |
| WO | 2009021754 A2 | 2/2009 |
| WO | 2010047830 A2 | 4/2010 |
| WO | 2011089183 A2 | 7/2011 |
| WO | 2012033987 A2 | 3/2012 |
| WO | 2013028070 A2 | 2/2013 |
| WO | 2013071138 A1 | 5/2013 |

OTHER PUBLICATIONS

Brodin; et al., "Regulation of Thrombin Generation by TFPI in Plasma without and with Heparin", Translational Research, Mar. 2009, vol. 153 No. 3, 124-131.
Brown; et al., "Tolerance to Single, but Not Multiple, Amino Acid Replacements in Antibody VH CDR2: A Means of Minimizing B Cell Wastage from Somatic Hypermutation?", The Journal of Immunology, May 1996, vol. 156 No. 6, 3285-3291.
Casset; et al., "A peptide mimetic of an anti-CD4 monoclonal antibody by rational design", Biochemical and Biophysical Research Communications, 2003, vol. 307, 198-205.
Chamely et al., "Inhibition of heparin/antithrombin III cofactor activity by anticardiolipin antibodies: A mechanism for thrombosis," Thrombosis Research, 71(2): 102-11 (Jul. 15, 1993). Abstract Only.
Chan; et al., "Heparin-Antithrombin III Binding in Vitro and in Vivo Studies," Haemostasis, 8:373-89 (1979)., Haemostasis, 1979, vol. 8 No. 6, 373-389.
Chuang; et al., "Heparin Enhances the Specificity of Antithrombin for Thrombin and Factor Xa Independent of the Reactive Center Loop Sequence", The Journal of Biological Chemistry, 2001, vol. 276 No. 18, 14961-14971.
Colman; P.M., "Effects of Amino Acid Sequence Changes on Antibody-Antigen Interactions", Research in Immunology, 1994, vol. 145, 33-36.
Dawes; et al., "Conformational Change in Antithrombin Induced by Heparin, Probed with a Monoclonal Antibody against the 1C/4B Region", Biochemistry, 1994, vol. 33 No. 14, 4375-4383.
Dawes et al., "The conformational change in antithrombin-III induced by heparin, probed with monoclonalantibodies," Thrombosis and Haemostasis, 62(1):473 (Aug. 19, 1989).
Desai; Umesh, "New Antithrombin-Based Anticoagulants", Medicinal Research Reviews, Mar. 2004, vol. 24 No. 2, 151-181.
Devraj-Kizuk, R. etal!., "Antithrombin-III-Hamilton: A gene with a Point Mutation (Guanine to Adenine) in Codon 382 Causing Impaired Serine Protease Reactivity", Blood, vol. 72, No. 5, Nov. 1988, pp. 1518-1523.
Di; Micco et al., "Inhibition of Antithrombin by Protein SV-IV Normalizes the Coagulation of Hemophilic Blood", European Journal of Pharmacology, 2000, vol. 391, 1-9.
Erdjument; et al., "Antithrombin Chicago Amino Acid Substitution of Arginine 393 to Histidine", Thrombosis Research, Jun. 15, 1989, vol. 54 No. 6, 613-619.
Gershoni; et al., "Epitope Mapping: The First Step in Developing Epitope-Based Vaccines", Drug Development, 2007, vol. 21 No. 3, 145-154.
Herion et al., "Monoclonal antibodies against plasma protease inhibitors: production and characterization of 15 monoclonal antibodies against human antithrombin III. Relation between .antigenic determinants and functional sites of antithrombin III," Blood, 65(5):1201-07 (1985).
Hrkal et al., "Monoclonal antibodies against human antithrombin III," Hybridoma, 10(5):633-40 (Oct. 1991).
International Search Report and Written Opinion for PCT/US2014/029541 dated Jul. 28, 2014.
International Search Report for International Application No. PCT/NL2012/050581, International Publication No. WO 2013/028070 A3 dated Apr. 3, 2013.
International Search Report for PCT/EP2008/059486, International Publication No. WO 2009/013251 dated Oct. 28, 2008.
International Search Report issued in PCT/US2014/029541 dated Jul. 28, 2014.
Jairajpuri, M. et al., "Elimination of PI Arginine 393 Interaction with Underlying Glutamic Acid 255 Partially Activates Antithrombin III for Thrombin Inhibition but not Factor Xa Inhibition", The Journal of Biological Chemistry, Jul. 5, 2002, vol. 277, No. 27, pp. 24460-24465.
Kjellberg M., et al. The cleaved and latent forms of antihrombin are normal constituents of blood plasma: a quantitative method to measure cleaved antihrombin. J. Thromb Haemost 2006; 4: 168-176.
Knoller; et al., "Monoclonal Antibodies Against Antithrombin III", European Journal of Biochemistry, Mar. 15 , 1989, vol. 180, 319-326.
Kummer, J. et al., "Production, Characterization, and use ofSerpin Antibodies", Methods: A Companion to Methods in Enzymology, Academic Press, Inc., New York, NY, US, vol. 32, No. 2, Feb. 1, 2004, pp. 141-149.
Li et al. "Structure of the antithrombin-thrombin-heparin ternary complex reveals the antithrombotic mechanism of heparin", Nature Structural & Molecular Biology, Nature Publishing Group, US, vol. 11, No. 9 (Sep. 1, 2004), pp. 857-862.
Long; et al., "Probing Plasma Clearance of the Thrombin-Antithrombin Complex with a Monoclonal Antibody Against the Putative Serpin-Enzyme Complex Receptor-Binding Site", European Journal of Biochemistry, 2003, vol. 270, 4059-4069.
MacCallum et al. Antibody interactions: contact analysis and binding site topography. Journal of Molecular Biology, 262:732-745, 1996.
Matsuda et al., "Sole existence of antithrombin antibody in patients with systemic lupus erythematosus showing tendency of its antigenic determinants directing against exosite II (antithrombin/heparin binding site) of thrombin," Bood Coagulation & Fibrinolysis, 19(1):66-69 (Jan. 2008).
Mayer, S. et al., "Recombinant Activated Factor VII for Acute Intracerebral Hemorrhage", New England Journal of Medicine, The Massachusetts Medical Society, Waltham, MA, US, vol. 352, No. 8., Feb. 24, 2005, pp. 777-785.
Moriyama et al., "A monoclonal antibody against bovine thrombin reacting to the C-terminal side of thrombin," Hybridoma and Hybridomics, 20(5/6):397-403 (2001 ). Abstract Only.
Muszbek, L. et al., "Antithrombin deficiency and its laboratory diagnosis", Clinical Chemistry and Laboratory Medicine, vol. 48, Suppl. 1, Dec. 2010 (Dec. 2010), pp. 567-578.
Patel; et al., "Covalent Antithrombin-Heparin Complexes", Thrombosis Research, Jan. 1, 2007, vol. 120 No. 2, 151-160.
Paul, Fundamental Immunology, 3rd Edition, 1993, pp. 292-295.
Rudikoff; et al., "Single Amino Acid Substitution Altering Antigen-Binding Specificity", Proceeding of the National Academy of Sciences, Mar. 1982, vol. 79 No. 6, 1979-1983.
Vajdos et al. Comprehensive Functional Maps of the Antigen-binding Site of an Anti-ErbB2 Antibody Obtained with Shotgun Mutagenesis. Journal of Molecular Biology. Jul. 5, 2002; 320(2)415-28.
Watton et al., "A monoclonal-antibody (MAb) to antithrombin-III (AT III) that recognizes the heparin bindingsite," Thrombosis and Haemostasis, 65(6):914 (Jun. 5, 1991), Jun. 5, 1991, Nat! Inst Bioi Stand & Controls, Potters Bar, Herts, England; Charing Cross & Westminster Med Sch, London, England.

(56) References Cited

OTHER PUBLICATIONS

Watton et al., "Heparin binding affinity of normal and genetically modified antithrombin III measured using a monoclonal antibody to the heparin binding site of antithrombin III," Biochemistry, 32(28):7286-93 (1993).
Written Opinion of the International Searching Authority for corresponding application dated Jul. 28, 2014.
Wu et al, "Defining the heparin-binding domain of antithrombin," Blood Coagulation & Fibrinolysis, 5(1):83-95 (1994).
Wu et al., "Use of antithrombin recombinant derivatives and fusion products to map its heparin-binding domains," Thrombosis and Haemostasis, 69(6):1140 (Jun. 30, 1993), Jun. 30, 1993, Canadian Red Cross Soc, Hamilton, On, Canada; Mcmaster Univ, Dept Pathol, Hamilton, Ontario, Canada.

* cited by examiner

Heavy Chain

```
TPP-2803|091E-M037-F02-LC-delA    EVQLLESGGGLVQPGGSLRLSCAASGFTF SYRMS WVRQAPGKGLEWVSR    50
TPP-2009|091E-M037-F02-higGihe    EVQLLESGGGLVQPGGSLRLSCAASGFTF SYRMS WVRQAPGKGLEWVSR    50
TPP-2016|091E-M046-H07-higGihe    EVQLLESGGGLVQPGGSLRLSCAASGFTF SAYRMG WVRQAPGKGLEWVSR   50
TPP-2015|091E-M044-B02-higGihe    EVQLLESGGGLVQPGGSLRLSCAASGFTF SKYRMD WVRQAPGKGLEWVSR   50
TPP-2019|091E-M067-O08-higGihe    EVQLLESGGGLVQPGGSLRLSCAASGFTF RVAME WVRQAPGKGLEWVSH    50
                                  ****:*********************** :      **************
                                                                HCDR1

TPP-2803|091E-M037-F02-LC-delA    IYSSGGRTRYADSVKG RFTISRDNSKNTLYLQMNSLRAEDTAVYYC AREK   100
TPP-2009|091E-M037-F02-higGihe    IYSSGGRTRYADSVKG RFTISRDNSKNTLYLQMNSLRAEDTAVYYC AREK   100
TPP-2016|091E-M046-H07-higGihe    IGPSGGKTTYADSVKG RFTISRDNSKNTLYLQMNSLRAEDTAVYYC AREK   100
TPP-2015|091E-M044-B02-higGihe    IYSSGGKTMYADSVKG RFTISRDNSKNTLYLQMNSLRAEDTAVYYC AREK   100
TPP-2019|091E-M067-O08-higGihe    ISPSGGKTHYADSVKG RFTISRDNSKNTLYLQMNSLRAEDTAVYYC ARLS   100
                                  *  ***:*:*******  ****************************  **
                                        HCDR2

TPP-2803|091E-M037-F02-LC-delA    ASDLSGSFS-EALDY WGQGTLVTVSS    125
TPP-2009|091E-M037-F02-higGihe    ASDLSGSFS-EALDY WGQGTLVTVSS    125
TPP-2016|091E-M046-H07-higGihe    TSDLSGSYS-EALDY WGQGTLVTVSS    125
TPP-2015|091E-M044-B02-higGihe    ASDLSGTYS-EALDY WGQGTLVTVSS    125
TPP-2019|091E-M067-O08-higGihe    QTGYY PHYHYYGMDV WGQGTTVTVSS   126
                                  :    *  ***** *****
                                  HCDR3
```

FIG. 7C

| Antibody | Ka | Kd | KD (nm) |
|---|---|---|---|
| TPP 2009 | 1.07E+05 | 1.27E-03 | 11.9 |
| TPP 2015 | 3.95E+04 | 1.09E-03 | 27.7 |
| TPP 2016 | 6.05E+04 | 1.15E-03 | 18.9 |
| TPP 2019 | 8.11E+04 | 1.39E-03 | 17.2 |

FIG. 8B

| | FVIII-DP | AT-DP +ATIIIa | AT-DP +ATIIIb |
|---|---|---|---|
| Plasma only | 210.0 | 165.2 | 167.0 |
| Plasma + ATIIIa | -- | 238.3 | -- |
| Plasma + ATIIIb | -- | -- | 402.6 |
| TPP2009 | 176.7 | 233.0 | 237.9 |
| TPP2010 | 199.1 | 237.7 | 356.3 |
| TPP2011 | 205.9 | 234.8 | 380.7 |
| TPP2012 | 218.7 | 278.9 | 320.6 |
| TPP2013 | 206.5 | 241.5 | 366.1 |
| TPP2014 | 213.0 | 240.5 | 383.0 |
| TPP2015 | 199.7 | 229.7 | 316.3 |
| TPP2016 | 183.4 | 230.6 | 272.5 |
| TPP2017 | 203.2 | 242.6 | 332.9 |
| TPP2018 | 202.8 | 239.6 | 373.3 |
| TPP2019 | 195.8 | 233.0 | 322.8 |
| TPP754 (control) | 204.3 | 237.1 | 385.2 |

FIG. 10A
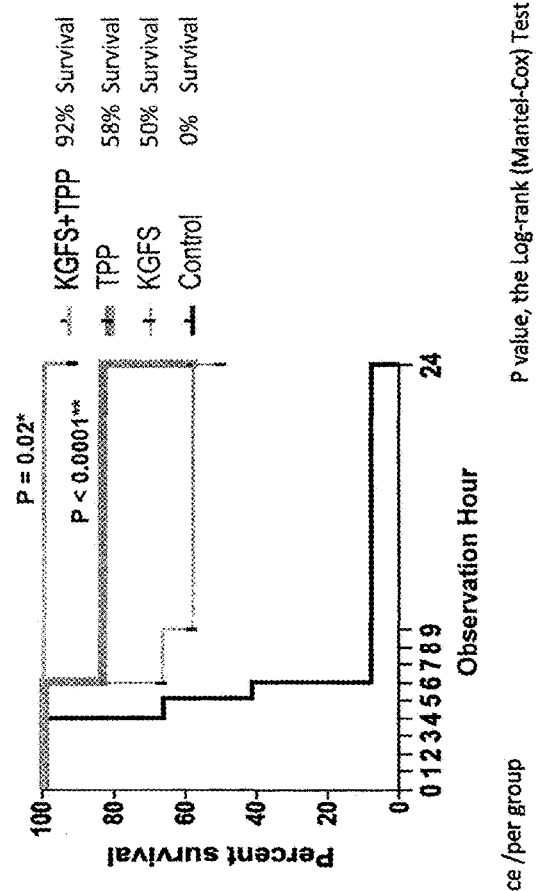
FIG. 10B
Figure 10B

SEQUENCE LISTING

```
<160> NUMBER OF SEQ ID NOS: 60

<210> SEQ ID NO 1
<211> LENGTH: 215
<212> TYPE: PRT
<213> ORGANISM: Artificial Sequence
<220> FEATURE:
<223> OTHER INFORMATION: TPP2009, Light Chain Variable Region

<400> SEQUENCE: 1

Ala Gln Ser Val Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Tyr
            20                  25                  30

Ala Ser Trp Tyr Gln Gln Lys Pro Gly Gln Ala Pro Val Leu Val Ile
        35                  40                  45

Tyr Gly Lys Asn Asn Arg Pro Ser Gly Ile Pro Asp Arg Phe Ser Gly
    50                  55                  60

Ser Ser Ser Gly Asn Thr Ala Ser Leu Thr Ile Thr Gly Ala Gln Ala
65                  70                  75                  80

Glu Asp Glu Ala Asp Tyr Tyr Cys Asn Ser Arg Asp Ser Ser Gly Asn
                85                  90                  95

His Leu Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140
```

```
Gly Ala Val Thr Val Ala Trp Lys Ala Asp Gly Ser Pro Val Lys Ala
145                 150                 155                 160

Gly Val Glu Thr Thr Lys Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
    195                 200                 205

Val Ala Pro Ala Glu Cys Ser
210                 215
```

<210> SEQ ID NO 2
<211> LENGTH: 125
<212> TYPE: PRT
<213> ORGANISM: Artificial Sequence
<220> FEATURE:
<223> OTHER INFORMATION: TPP2009, Heavy Chain Variable Region

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Arg Met Gly Trp Val Arg Gln Ala Pro Gly Lys Gly Leu Glu Trp Val
        35                  40                  45

Ser Arg Ile Tyr Ser Ser Gly Gly Arg Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Ala Ser Asp Leu Ser Gly Ser Phe Ser Glu Ala Leu
            100                 105                 110

Asp Tyr Trp Gly Gln Gly Thr Leu Val Thr Val Ser Ser
        115                 120                 125
```

<210> SEQ ID NO 3
<211> LENGTH: 216
<212> TYPE: PRT
<213> ORGANISM: Artificial Sequence
<220> FEATURE:
<223> OTHER INFORMATION: TPP2015, Light Chain Variable Region

<400> SEQUENCE: 3

```
Ala Gln Asp Ile Gln Met Thr Gln Ser Pro Gly Thr Leu Ser Leu Ser
1               5                   10                  15

Pro Gly Glu Arg Ala Thr Leu Ser Cys Arg Ala Ser Gln Ser Val Ser
            20                  25                  30

Ser Ser Tyr Leu Ala Trp Tyr Gln Gln Lys Pro Gly Gln Ala Pro Arg
        35                  40                  45

Leu Leu Ile Tyr Gly Ala Ser Ser Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Tyr Gly Ser
                85                  90                  95

Ser Arg Thr Phe Gly Gln Gly Thr Lys Val Glu Ile Arg Arg Thr Val
```

```
                    100                 105                 110
Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 4
<211> LENGTH: 125
<212> TYPE: PRT
<213> ORGANISM: Artificial Sequence
<220> FEATURE:
<223> OTHER INFORMATION: TPP2015, Heavy Chain Variable Region

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Lys Met Asp Trp Val Arg Gln Ala Pro Gly Lys Gly Leu Glu Trp Val
        35                  40                  45

Ser Arg Ile Gly Pro Ser Gly Gly Lys Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Ala Ser Asp Leu Ser Gly Tyr Ser Glu Ala Leu
            100                 105                 110

Asp Tyr Trp Gly Gln Gly Thr Leu Val Thr Val Ser Ser
        115                 120                 125

<210> SEQ ID NO 5
<211> LENGTH: 216
<212> TYPE: PRT
<213> ORGANISM: Artificial Sequence
<220> FEATURE:
<223> OTHER INFORMATION: TPP2016, Light Chain Variable Region

<400> SEQUENCE: 5

Ala Gln Asp Ile Gln Met Thr Gln Ser Pro Ala Thr Leu Ser Val Ser
1               5                   10                  15

Pro Gly Glu Arg Ala Thr Leu Ser Cys Arg Ala Ser Gln Asn Ile Asn
            20                  25                  30

Arg Asn Leu Ala Trp Tyr Gln Gln Lys Pro Gly Arg Ala Pro Arg Leu
        35                  40                  45

Leu Ile His Thr Ala Ser Thr Arg Ala Pro Gly Val Pro Val Arg Ile
    50                  55                  60
```

```
Thr Gly Ser Gly Ser Gly Thr Glu Phe Thr Leu Thr Ile Ser Ser Leu
 65                  70                  75                  80

Glu Pro Glu Asp Phe Ala Val Tyr Phe Cys Gln Gln Tyr Ala Ser Pro
                 85                  90                  95

Pro Arg Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 6
<211> LENGTH: 125
<212> TYPE: PRT
<213> ORGANISM: Artificial Sequence
<220> FEATURE:
<223> OTHER INFORMATION: TPP2016, Heavy Chain Variable Region

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Arg Met Asp Trp Val Arg Gln Ala Pro Gly Lys Gly Leu Glu Trp Val
        35                  40                  45

Ser Arg Ile Gly Pro Ser Gly Gly Lys Thr Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Lys Thr Ser Asp Leu Ser Gly Ser Tyr Ser Glu Ala Leu
            100                 105                 110

Asp Tyr Trp Gly Gln Gly Thr Leu Val Thr Val Ser Ser
            115                 120                 125

<210> SEQ ID NO 7
<211> LENGTH: 218
<212> TYPE: PRT
<213> ORGANISM: Artificial Sequence
<220> FEATURE:
<223> OTHER INFORMATION: TPP2019, Light Chain Variable Region

<400> SEQUENCE: 7

Ala Gln Asp Ile Gln Met Thr Gln Ser Pro Ala Thr Leu Ser Leu Ser
1               5                   10                  15

Pro Gly Glu Arg Ala Thr Leu Ser Cys Arg Ala Ser Gln Arg Val Ser
            20                  25                  30
```

Ser Ser Tyr Leu Thr Trp Tyr Gln Gln Lys Pro Gly Gln Ala Pro Arg
            35                  40                  45

Leu Leu Ile Tyr Gly Ala Ser Ser Arg Ala Thr Gly Ile Pro Asp Arg
 50                  55                  60

Phe Ser Gly Ser Gly Ser Gly Thr Asp Phe Thr Leu Thr Ile Ser Arg
 65                  70                  75                  80

Leu Glu Pro Glu Asp Phe Ala Val Tyr Tyr Cys Gln Gln Tyr Asp Ser
                 85                  90                  95

Thr Pro Pro Leu Thr Phe Gly Gly Thr Lys Val Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
         130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                 165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 8
<211> LENGTH: 126
<212> TYPE: PRT
<213> ORGANISM: Artificial Sequence
<220> FEATURE:
<223> OTHER INFORMATION: TPP2019, Heavy Chain Variable Region

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Tyr Trp Val Arg Gln Ala Pro Gly Lys Gly Leu Glu Trp Val
        35                  40                  45

Ser Arg Ile Ser Pro Ser Gly Gly Lys Thr His Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ser Gln Thr Gly Tyr Tyr Pro His Tyr His Tyr Tyr Gly
            100                 105                 110

Met Asp Val Trp Gly Gln Gly Thr Thr Val Thr Val Ser Ser
        115                 120                 125

<210> SEQ ID NO 9
<211> LENGTH: 214
<212> TYPE: PRT
<213> ORGANISM: Artificial Sequence
<220> FEATURE:
<223> OTHER INFORMATION: TPP2803, Light Chain Variable Region

<400> SEQUENCE: 9

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210

<210> SEQ ID NO 10
<211> LENGTH: 125
<212> TYPE: PRT
<213> ORGANISM: Artificial Sequence
<220> FEATURE:
<223> OTHER INFORMATION: TPP2803, Heavy Chain Variable Region

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Arg Ile Tyr Ser Ser Gly Gly Arg Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Ala Ser Asp Leu Ser Gly Ser Phe Ser Glu Ala Leu
            100                 105                 110

Asp Tyr Trp Gly Gln Gly Thr Leu Val Thr Val Ser Ser
        115                 120                 125

<210> SEQ ID NO 11
<211> LENGTH: 645
<212> TYPE: DNA
<213> ORGANISM: Artificial Sequence
<220> FEATURE:
<223> OTHER INFORMATION: TPP2009 Light Chain_V region

<400> SEQUENCE: 11

```
gcacagagcg tcttgactca ggaccctgct gtgtctgtgg ccttgggaca gacagtcagg      60
atcacatgcc aaggagacag cctcagaagc tattatgcaa gctggtacca gcagaagcca     120
ggacaggccc ctgtacttgt catctatggt aaaaacaacc ggccctcagg gatcccagac     180
cgattctctg gctccagctc aggaaacaca gcttccttga ccatcactgg ggctcaggcg     240
gaagatgagg ctgactatta ctgtaactcc cgggacagca gtggtaacca tctggtattc     300
ggcggaggga ccaagctgac cgtcctaggt cagcccaagg ctgccccctc ggtcactctg     360
ttcccgccct cctctgagga gcttcaagcc aacaaggcca cactagtgtg tctgatcagt     420
gacttctacc cgggagctgt gacagtggcc tggaaggcag atggcagccc cgtcaaggcg     480
ggagtggaga ccaccaaacc ctccaaacag agcaacaaca agtacgcggc cagcagctac     540
ctgagcctga cgcccgagca gtggaagtcc cacagaagct acagctgcca ggtcacgcat     600
gaagggagca ccgtggagaa gacagtggcc cctgcagaat gctct                    645
```

<210> SEQ ID NO 12
<211> LENGTH: 1362
<212> TYPE: DNA
<213> ORGANISM: Artificial Sequence
<220> FEATURE:
<223> OTHER INFORMATION: TPP2009 Heavy chain

<400> SEQUENCE: 12

```
gaagttcaat tgttagagtc tggtggcggt cttgttcagc ctggtggttc tttacgtctt      60
tcttgcgctg cttccggatt cactttctct gcttaccgta tgggttgggt tcgccaagct     120
cctggtaaag gtttggagtg gtttctcgt atctattctt ctggtggccg tactcgttat     180
gctgactccg ttaaaggtcg cttcactatc tctagagaca actctaagaa tactctctac     240
ttgcagatga acagcttaag ggctgaggac acggccgtgt attactgtgc gagagagaaa     300
gcgtcggatc tatcggggag ttttttctgag gcccttgact actggggcca gggaaccctg     360
gtcaccgtct caagcgcctc caccaagggc ccatcggtct tccccgctag cccagcagc     420
aagagcacca gcggcggaac agccgccctg gctgcctg tgaaagacta cttccccgag     480
cccgtgaccg tgtcctggaa ctctggcgcc ctgaccagcg gagtgcatac cttccccgcc     540
gtgctgcaga gcagcggcct gtacagcctg agcagcgtgg tgacagtgcc cagcagcagc     600
ctgggaaccc agacctacat ctgcaacgtg aaccacaagc ccagcaacac caaggtggac     660
aagaaggtgg aacccaagag ctgcgacaag acccacacct gtcccccctg ccctgcccct     720
gaactgctgg gcggacccag cgtgttcctg ttccccccaa agcccaagga caccctgatg     780
atcagccgga cccccgaagt gacctgcgtg gtggtggacg tgtcccacga ggacccagaa     840
gtgaagttta attggtacgt ggacggcgtg gaagtgcata acgccaagac caagccagag     900
gaggaacagt acaacagcac ctaccgggtg gtgtccgtgc tgaccgtgct gcaccaggac     960
tggctgaacg gcaaagagta caagtgcaag gtctccaaca aggccctgcc tgccccatc     1020
gagaaaacca tcagcaaggc caagggccag ccccgcgagc ctcaggtgta cactctgccc     1080
cccagccggg atgagctgac caagaaccag gtgtccctga cctgtctggt gaaaggcttc     1140
```

-continued

| | |
|---|---|
| taccccagcg atatcgccgt ggaatgggag agcaacggcc agcccgagaa caattacaag | 1200 |
| accaccccc ctgtgctgga cagcgacggc tcattcttcc tgtactccaa gctgaccgtg | 1260 |
| gacaagagcc ggtggcagca gggcaacgtg ttcagctgca gcgtgatgca cgaggccctg | 1320 |
| cacaatcact acacccagaa gtccctgagc ctgagccccg gc | 1362 |

<210> SEQ ID NO 13
<211> LENGTH: 642
<212> TYPE: DNA
<213> ORGANISM: Artificial Sequence
<220> FEATURE:
<223> OTHER INFORMATION: TPP2015 Light Chain_V region

<400> SEQUENCE: 13

| | |
|---|---|
| gcacaagaca tccagatgac ccagtctcca ggcaccctgt ctttgtctcc aggggaaaga | 60 |
| gccaccctct cctgcagggc cagtcagagt gttagcagca gctacttagc ctggtaccag | 120 |
| cagaaacctg gccaggctcc caggctcctc atctatggtg catccagcag ggccactggc | 180 |
| atcccagaca ggttcagtgg cagtgggtct gggacagact tcactctcac catcagcaga | 240 |
| cggagcctga gattttgca gtgtattact gtcagcagta tggtagctca acgttcggcc | 300 |
| aagggaccaa ggtggaaatc agacgaactg tggctgcaat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 14
<211> LENGTH: 1362
<212> TYPE: DNA
<213> ORGANISM: Artificial Sequence
<220> FEATURE:
<223> OTHER INFORMATION: TPP2015 Heavy Chain

<400> SEQUENCE: 14

| | |
|---|---|
| gaagttcaat tgttagagtc tggtggcggt cttgttcagc ctggtggttc tttacgtctt | 60 |
| tcttgcgctg cttccggatt cactttctct aagtacaaga tggattgggt tcgccaagct | 120 |
| cctggtaaag gtttggagtg ggtttctcgt atcggtcctt ctggtggcaa gactatgtat | 180 |
| gctgactccg ttaaaggtcg cttcactatc tctagagaca actctaagaa tactctctac | 240 |
| ttgcagatga acagcttaag ggctgaggac acggccgtgt attactgtgc gagagagaaa | 300 |
| gcgtcggatc tatcggggac ttattctgag gcccttgact actggggcca gggaaccctg | 360 |
| gtcaccgtct caagcgcctc caccaagggc ccatcggtct tccccgctag cccagcagc | 420 |
| aagagcacca gcggcggaac agccgccctg ggctgcctgg tgaaagacta cttccccgag | 480 |
| cccgtgaccg tgtcctggaa ctctggcgcc ctgaccagcg gagtgcatac cttccccgcc | 540 |
| gtgctgcaga gcagcggcct gtacagcctg agcagcgtgg tgacagtgcc cagcagcagc | 600 |
| ctgggaaccc agacctacat ctgcaacgtg aaccacaagc ccagcaacac caaggtggac | 660 |
| aagaaggtgg aacccaagag ctgcgacaag acccacacct gtcccccctg ccctgcccct | 720 |
| gaactgctgg gcggacccag cgtgttcctg ttccccccaa agcccaagga caccctgatg | 780 |
| atcagccgga cccccgaagt gacctgcgtg gtggtggacg tgtcccacga ggacccagaa | 840 |
| gtgaagttta attggtacgt ggacggcgtg gaagtgcata acgccaagac caagcccaga | 900 |

```
gaggaacagt acaacagcac ctaccgggtg gtgtccgtgc tgaccgtgct gcaccaggac      960
tggctgaacg gcaaagagta caagtgcaag gtctccaaca aggccctgcc tgcccccatc     1020
gagaaaacca tcagcaaggc caagggccag ccccgcgagc tcaggtgta cacactgccc     1080 cccagccggg atgagctgac caagaaccag gtgtccctga cctgtctggt gaaaggcttc     1140
taccccagcg atatcgccgt ggaatgggag agcaacggcc agcccgagaa caattacaag     1200 accaccccc ctgtgctgga cagcgacggc tcattcttcc tgtactccaa gctgaccgtg     1260
gacaagagcc ggtggcagca gggcaacgtg ttcagctgca gcgtgatgca cgaggccctg     1320
cacaatcact acacccagaa gtccctgagc ctgagccccg gc                        1362
```

<210> SEQ ID NO 15
<211> LENGTH: 648
<212> TYPE: DNA
<213> ORGANISM: Artificial Sequence
<220> FEATURE:
<223> OTHER INFORMATION: TPP2016 Light Chain_V region

<400> SEQUENCE: 15

```
gcacaagaca tccagatgac ccagtctcca gccaccctgt ctgtgtctcc aggggaaaga      60
gccaccctct cctgcagggc cagtcagaat attaatagaa acttggcctg gtaccagcag     120
aagcctggcc gggctcccag actcctcatc catacogcat ccactagggc ccctggtgtc     180
ccagtcagga tcactggcag tgggtctgga acagagttca ctctcaccat cagcagcctg     240
gaacctgaag attttgcagt gtatttctgt cagcagtatg ctagcccacc tcggacgttc     300
ggccaaggga ccaaggtgga aatcaagcga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648
```

<210> SEQ ID NO 16
<211> LENGTH: 1362
<212> TYPE: DNA
<213> ORGANISM: Artificial Sequence
<220> FEATURE:
<223> OTHER INFORMATION: TPP2016 Heavy Chain

<400> SEQUENCE: 16

```
gaagttcaat tgttagagtc tggtggcggt cttgttcagc ctggtggttc tttacgtctt      60
tcttgcgctg cttccggatt cactttctct aagtaccgta tggattgggt tcgccaagct     120
cctggtaaag gtttggagtg ggtttctcgt atcggtcctt ctggtggcaa gactacttat     180
gctgactccg ttaaaggtcg cttcactatc tctagagaca actctaagaa tactctctac     240
ttgcagatga acagcttaag ggctgaggac acggccgtgt attactgtgc gagagagaaa     300
acgtcggatc tatcggggag ttattctgag gcccttgact actggggcca gggaaccctg     360
gtcaccgtct caagcgcctc caccaagggc ccatcggtct tccccgctag cacccagcagc     420 aagagcacca gcggcggaac agccgccctg ggctgcctgg tgaaagacta cttccccgag     480
cccgtgaccg tgtcctggaa ctctggcgcc ctgaccagcg gagtgcatac cttccccgcc     540
gtgctgcaga gcagcggcct gtacagcctg agcagcgtgg tgacagtgcc cagcagcagc     600
```

| | |
|---|---|
| ctgggaaccc agacctacat ctgcaacgtg aaccacaagc ccagcaacac caaggtggac | 660 |
| aagaaggtgg aacccaagag ctgcgacaag acccacacct gtccccctg ccctgcccct | 720 |
| gaactgctgg gcggaccag cgtgttcctg ttcccccaa agcccaagga caccctgatg | 780 |
| atcagccgga cccccgaagt gacctgcgtg gtggtggacg tgtcccacga ggacccagaa | 840 |
| gtgaagttta attggtacgt ggacggcgtg gaagtgcata cgccaagac caagcccaga | 900 |
| gaggaacagt acaacagcac ctaccgggtg gtgtccgtgc tgaccgtgct gcaccaggac | 960 |
| tggctgaacg gcaaagagta caagtgcaag gtctccaaca aggccctgcc tgcccccatc | 1020 |
| gagaaaacca tcagcaaggc caagggccag ccccgcgagc ctcaggtgta cactgccc | 1080 |
| cccagccggg atgagctgac caagaaccag gtgtccctga cctgtctggt gaaaggcttc | 1140 |
| taccccagcg atatcgccgt ggaatgggag agcaacggcc agcccgagaa caattacaag | 1200 |
| accacccccc ctgtgctgga cagcgacggc tcattcttcc tgtactccaa gctgaccgtg | 1260 |
| gacaagagcc ggtggcagca gggcaacgtg ttcagctgca gcgtgatgca cgaggccctg | 1320 |
| cacaatcact acacccagaa gtccctgagc ctgagccccg gc | 1362 |

<210> SEQ ID NO 17
<211> LENGTH: 654
<212> TYPE: DNA
<213> ORGANISM: Artificial Sequence
<220> FEATURE:
<223> OTHER INFORMATION: TPP2019 Light Chain_V region

<400> SEQUENCE: 17

| | |
|---|---|
| gcacaagaca tccagatgac ccagtctcca gccaccctgt ctttgtctcc aggggaaaga | 60 |
| gccaccctct cctgcagggc cagtcagcgt gttagcagca gctacttaac ctggtaccag | 120 |
| cagaaacctg gccaggctcc caggctcctc atctatggtg catccagcag ggccactggc | 180 |
| atcccagaca ggttcagtgg cagtgggtct gggacagact tcactctcac catcagcaga | 240 |
| ctggagcctg aagattttgc agtttattac tgtcagcagt atgatagtac gcctccgctc | 300 |
| accttcggcg gagggaccaa ggtggagatc aaacgaactg tggctgcacc atctgtcttc | 360 |
| atcttcccgc catctgatga gcagttgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca agtctacgc ctgcgaagtc | 600 |
| acccatcagg gcctgagctc gcccgtcaca aagagcttca caggggaga gtgt | 654 |

<210> SEQ ID NO 18
<211> LENGTH: 1365
<212> TYPE: DNA
<213> ORGANISM: Artificial Sequence
<220> FEATURE:
<223> OTHER INFORMATION: TPP2019 Heavy chain

<400> SEQUENCE: 18

| | |
|---|---|
| gaagttcaat tgttagagtc tggtggcggt cttgttcagc ctggtggttc tttacgtctt | 60 |
| tcttgcgctg cttccggatt cactttctct cgttacgcta tgtattgggt tcgccaagct | 120 |
| cctggtaaag gtttggagtg ggtttctcgt atctctcctt ctggtggcaa gactcattat | 180 |
| gctgactccg ttaaaggtcg cttcactatc tctagagaca actctaagaa tactctctac | 240 |
| ttgcagatga cagccttaag ggctgaggac acggccgtgt attactgtgc gagactgtct | 300 |
| caaactggtt attaccctca ctaccactac tacggtatgg acgtctgggg ccaagggacc | 360 |

```
acggtcaccg tctcaagcgc ctccaccaag ggcccatcgg tcttcccgct agcacccagc    420
agcaagagca ccagcggcgg aacagccgcc ctgggctgcc tggtgaaaga ctacttcccc    480
gagcccgtga ccgtgtcctg gaactctggc gccctgacca gcggagtgca taccttcccc    540
gccgtgctgc agagcagcgg cctgtacagc ctgagcagcg tggtgacagt gcccagcagc    600
agcctgggaa cccagaccta catctgcaac gtgaaccaca agcccagcaa caccaaggtg    660
gacaagaagg tggaacccaa gagctgcgac aagacccaca cctgtccccc ctgccctgcc    720
cctgaactgc tgggcggacc cagcgtgttc ctgttccccc caaagcccaa ggacaccctg    780
atgatcagcc ggaccccga agtgacctgc gtggtggtgg acgtgtccca cgaggaccca    840
gaagtgaagt ttaattggta cgtggacggc gtggaagtgc ataacgccaa gaccaagccc    900
agagaggaac agtacaacag cacctaccgg gtggtgtccg tgctgaccgt gctgcaccag    960
gactggctga acggcaaaga gtacaagtgc aaggtctcca acaaggccct gcctgccccc   1020
atcgagaaaa ccatcagcaa ggccaagggc cagccccgcg agcctcaggt gtacacactg   1080 cccccagcc gggatgagct gaccaagaac caggtgtccc tgacctgtct ggtgaaaggc   1140
ttctacccca gcgatatcgc cgtggaatgg gagagcaacg gccagcccga gaacaattac   1200
aagaccaccc cccctgtgct ggacagcgac ggctcattct tcctgtactc caagctgacc   1260
gtggacaaga gccggtggca gcagggcaac gtgttcagct gcagcgtgat gcacgaggcc   1320
ctgcacaatc actacaccca gaagtccctg agcctgagcc ccggc                    1365

<210> SEQ ID NO 19
<211> LENGTH: 639
<212> TYPE: DNA
<213> ORGANISM: Artificial Sequence
<220> FEATURE:
<223> OTHER INFORMATION: TPP2803 Light Chain_V region

<400> SEQUENCE: 19
agcgaattga ctcaggaccc tgctgtgtct gtggccttgg acagacagt caggatcaca     60 tgccaaggag acagcctcag aagctattat gcaagctggt accagcagaa gccaggacag    120
gcccctgtac ttgtcatcta tggtaaaaac aaccggccct cagggatccc agaccgattc    180
tctggctcca gctcaggaaa cacagcttcc ttgaccatca ctgggctca ggcggaagat    240 gaggctgact attactgtaa ctcccgggac agcagtggta accatctggt attcggcgga    300
gggaccaagc tgaccgtcct aggtcagccc aaggctgccc cctcggtcac tctgttcccg    360
ccctcctctg aggagcttca agccaacaag gccacactag tgtgtctgat cagtgacttc    420
tacccgggag ctgtgacagt ggcctggaag gcagatggca gccccgtcaa ggcgggagtg    480
gagaccacca aaccctccaa acagagcaac aacaagtacg cggccagcag ctacctgagc    540
ctgacgcccg agcagtggaa gtcccacaga gctacagct gccaggtcac gcatgaaggg    600
agcaccgtgg agaagacagt ggcccctgca gaatgctct                           639

<210> SEQ ID NO 20
<211> LENGTH: 1348
<212> TYPE: DNA
<213> ORGANISM: Artificial Sequence
<220> FEATURE:
<223> OTHER INFORMATION: TPP2803 Heavy Chain

<400> SEQUENCE: 20
gaagtgcagc tgctggaaag cggcggaggc ctggtgcagc ctggcggatc tctgagactg     60
```

| | |
|---|---|
| agctgtgccg ccagcggctt caccttcagc agctacagaa tgagctgggt gcgccaggcc | 120 |
| cctggcaagg gactggaatg ggtgtcccgg atctacagca gcggcggcag aaccagatac | 180 |
| gccgacagcg tgaagggccg gttcaccatc tcccgggaca acagcaagaa caccctgtac | 240 |
| ctgcagatga acagcctgcg ggccgaggac accgccgtgt actattgcgc cagagagaag | 300 |
| gccagcgacc tgagcggcag ctttagcgag gccctggatt attggggcca gggcacactc | 360 |
| gtgaccgtgt ctagcgccag cacaaagggc ccagcgtgt ccctctggc ccctgtagc | 420 |
| agaagcacca gcgagtctac agccgccctg gctgcctcg tgaaggacta ctttcccgag | 480 |
| cccgtgacag tgtcctggaa ctctggcgcc ctgacaagcg gcgtgcacac ctttccagcc | 540 |
| gtgctgcaga gcagcggcct gtactctctg agcagcgtcg tgactgtgcc cagcagcaac | 600 |
| ttcggcaccc agacctacac ctgtaacgtg accacaagc ccagcaacac caaggtggac | 660 |
| aagaccgtgg aacggaagtg ctgcgtggaa tgccccccctt gtcctgcccc tccagtggct | 720 |
| ggcccttccg tgttcctgtt ccccccaaag cccaaggaca ccctgatgat cagccggacc | 780 |
| ccgaagtgac ctgcgtggtg gtggatgtgt cccacgagga ccccgaggtg cagttcaatt | 840 |
| ggtacgtgga cggcgtggaa gtgcacaacg ccaagaccaa gcccagagag gaacagttca | 900 |
| acagcaccttt ccgggtggtg tccgtgctga ccgtggtgca tcaggactgg ctgaacggca | 960 |
| aagagtacaa gtgcaaggtg tccaacaagg cctgcctgc ccccatcgag aaaaccatca | 1020 |
| gcaagaccaa aggccagccc cgcgagcccc aggtgtacac actgcctcca agccgggaag | 1080 |
| agatgaccaa gaaccaggtg tccctgacct gtctcgtgaa aggcttctac ccctccgata | 1140 |
| tcgccgtgga atgggagagc aacggccagc ccgagaacaa ctacaagacc acccccccca | 1200 |
| tgctggacag cgcggctcat tcttcctgta cagcaagctg acagtggaca agtcccggtg | 1260 |
| gcagcagggc aacgtgttca gctgcagcgt gatgcacgaa gccctgcaca accactacac | 1320 |
| ccagaagtcc ctgagcctga gccctggc | 1348 |

<210> SEQ ID NO 21
<211> LENGTH: 11
<212> TYPE: PRT
<213> ORGANISM: Artificial Sequence
<220> FEATURE:
<223> OTHER INFORMATION: TPP2009 LCDR1

<400> SEQUENCE: 21

Gln Gly Asp Ser Leu Arg Ser Tyr Tyr Ala Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: TPP2015 LCDR1

<400> SEQUENCE: 22

Arg Ala Ser Gln Ser Val Ser Ser Ser Tyr Leu Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: TPP2016 LCDR1

<400> SEQUENCE: 23

-continued

Arg Ala Ser Gln Asn Ile Asn Arg Asn Leu Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: TPP2019 LCDR1

<400> SEQUENCE: 24

Arg Ala Ser Gln Arg Val Ser Ser Ser Tyr Leu Thr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: TPP2803 LCDR1

<400> SEQUENCE: 25

Gln Gly Asp Ser Leu Arg Ser Tyr Tyr Ala Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: TPP2009 LCDR2

<400> SEQUENCE: 26

Gly Lys Asn Asn Arg Pro Ser
1               5

<210> SEQ ID NO 27
<211> LENGTH: 7
<212> TYPE: PRT
<213> ORGANISM: Artificial Sequence
<220> FEATURE:
<223> OTHER INFORMATION: TPP2015 LCDR2

<400> SEQUENCE: 27

Gly Ala Ser Ser Arg Ala Thr
1               5

<210> SEQ ID NO 28
<211> LENGTH: 7
<212> TYPE: PRT
<213> ORGANISM: Artificial Sequence
<220> FEATURE:
<223> OTHER INFORMATION: TPP2016 LCDR2

<400> SEQUENCE: 28

Thr Ala Ser Thr Arg Ala Pro
1               5

<210> SEQ ID NO 29
<211> LENGTH: 7
<212> TYPE: PRT
<213> ORGANISM: Artificial Sequence
<220> FEATURE:
<223> OTHER INFORMATION: TPP2019 LCDR2

<400> SEQUENCE: 29

Gly Ala Ser Ser Arg Ala Thr
1               5

<210> SEQ ID NO 30
<211> LENGTH: 7
<212> TYPE: PRT
<213> ORGANISM: Artificial Sequence
<220> FEATURE:
<223> OTHER INFORMATION: TPP2803 LCDR2

<400> SEQUENCE: 30

Gly Lys Asn Asn Arg Pro Ser
1               5

<210> SEQ ID NO 31
<211> LENGTH: 11
<212> TYPE: PRT
<213> ORGANISM: Artificial Sequence
<220> FEATURE:
<223> OTHER INFORMATION: TPP2009 LCDR3

<400> SEQUENCE: 31

Asn Ser Arg Asp Ser Ser Gly Asn His Leu Val
1               5                   10

<210> SEQ ID NO 32
<211> LENGTH: 8
<212> TYPE: PRT
<213> ORGANISM: Artificial Sequence
<220> FEATURE:
<223> OTHER INFORMATION: TPP2015 LCDR3

<400> SEQUENCE: 32

Gln Gln Tyr Gly Ser Ser Arg Thr
1               5

<210> SEQ ID NO 33
<211> LENGTH: 9
<212> TYPE: PRT
<213> ORGANISM: Artificial Sequence
<220> FEATURE:
<223> OTHER INFORMATION: TPP2016 LCDR3

<400> SEQUENCE: 33

Gln Gln Tyr Ala Ser Pro Pro Arg Thr
1               5

<210> SEQ ID NO 34
<211> LENGTH: 10
<212> TYPE: PRT
<213> ORGANISM: Artificial Sequence
<220> FEATURE:
<223> OTHER INFORMATION: TPP2019 LCDR3

<400> SEQUENCE: 34

Gln Gln Tyr Asp Ser Thr Pro Pro Leu Thr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: TPP2803 LCDR3

<400> SEQUENCE: 35

Asn Ser Arg Asp Ser Ser Gly Asn His Leu Val

```
1               5                   10
```

```
<210> SEQ ID NO 36
<211> LENGTH: 5
<212> TYPE: PRT
<213> ORGANISM: Artificial Sequence
<220> FEATURE:
<223> OTHER INFORMATION: TPP2009 HCDR1

<400> SEQUENCE: 36

Ala Tyr Arg Met Gly
1               5

<210> SEQ ID NO 37
<211> LENGTH: 5
<212> TYPE: PRT
<213> ORGANISM: Artificial Sequence
<220> FEATURE:
<223> OTHER INFORMATION: TPP2015 HCDR1

<400> SEQUENCE: 37

Lys Tyr Lys Met Asp
1               5

<210> SEQ ID NO 38
<211> LENGTH: 5
<212> TYPE: PRT
<213> ORGANISM: Artificial Sequence
<220> FEATURE:
<223> OTHER INFORMATION: TPP2016 HCDR1

<400> SEQUENCE: 38

Lys Tyr Arg Met Asp
1               5

<210> SEQ ID NO 39
<211> LENGTH: 5
<212> TYPE: PRT
<213> ORGANISM: Artificial Sequence
<220> FEATURE:
<223> OTHER INFORMATION: TPP2019 HCDR1

<400> SEQUENCE: 39

Arg Tyr Ala Met Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: TPP2803 HCDR1

<400> SEQUENCE: 40

Ser Tyr Arg Met Ser
1               5

<210> SEQ ID NO 41
<211> LENGTH: 17
<212> TYPE: PRT
<213> ORGANISM: Artificial Sequence
<220> FEATURE:
<223> OTHER INFORMATION: TPP2009 HCDR2

<400> SEQUENCE: 41

Arg Ile Tyr Ser Ser Gly Gly Arg Thr Arg Tyr Ala Asp Ser Val Lys
1               5                   10                  15
```

<210> SEQ ID NO 42
<211> LENGTH: 17
<212> TYPE: PRT
<213> ORGANISM: Artificial Sequence
<220> FEATURE:
<223> OTHER INFORMATION: TPP2015 HCDR2

<400> SEQUENCE: 42

Arg Ile Gly Pro Ser Gly Gly Lys Thr Met Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: TPP2016 HCDR2

<400> SEQUENCE: 43

Arg Ile Gly Pro Ser Gly Gly Lys Thr Thr Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: TPP2019 HCDR2

<400> SEQUENCE: 44

Arg Ile Ser Pro Ser Gly Gly Lys Thr His Tyr Ala Asp Ser Val Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: TPP2803 HCDR2

<400> SEQUENCE: 45

Arg Ile Tyr Ser Ser Gly Gly Arg Thr Arg Tyr Ala Asp Ser Val Lys
1               5                   10                  15

Gly

<210> SEQ ID NO 46
<211> LENGTH: 18
<212> TYPE: PRT
<213> ORGANISM: Artificial Sequence
<220> FEATURE:
<223> OTHER INFORMATION: TPP2009 HCDR3

<400> SEQUENCE: 46

Ala Arg Glu Lys Ala Ser Asp Leu Ser Gly Ser Phe Ser Glu Ala Leu
1               5                   10                  15

Asp Tyr

```
<210> SEQ ID NO 47
<211> LENGTH: 18
<212> TYPE: PRT
<213> ORGANISM: Artificial Sequence
<220> FEATURE:
<223> OTHER INFORMATION: TPP2015 HCDR3

<400> SEQUENCE: 47

Ala Arg Glu Lys Ala Ser Asp Leu Ser Gly Thr Tyr Ser Glu Ala Leu
1               5                   10                  15

Asp Tyr

<210> SEQ ID NO 48
<211> LENGTH: 18
<212> TYPE: PRT
<213> ORGANISM: Artificial Sequence
<220> FEATURE:
<223> OTHER INFORMATION: TPP2016 HCDR3

<400> SEQUENCE: 48

Ala Arg Glu Lys Thr Ser Asp Leu Ser Gly Ser Tyr Ser Glu Ala Leu
1               5                   10                  15

Asp Tyr

<210> SEQ ID NO 49
<211> LENGTH: 19
<212> TYPE: PRT
<213> ORGANISM: Artificial Sequence
<220> FEATURE:
<223> OTHER INFORMATION: TPP2019 HCDR3

<400> SEQUENCE: 49

Ala Arg Leu Ser Gln Thr Gly Tyr Tyr Pro His Tyr His Tyr Tyr Gly
1               5                   10                  15

Met Asp Val

<210> SEQ ID NO 50
<211> LENGTH: 18
<212> TYPE: PRT
<213> ORGANISM: Artificial Sequence
<220> FEATURE:
<223> OTHER INFORMATION: TPP2803 HCDR3

<400> SEQUENCE: 50

Ala Arg Glu Lys Ala Ser Asp Leu Ser Gly Ser Phe Ser Glu Ala Leu
1               5                   10                  15

Asp Tyr

<210> SEQ ID NO 51
<211> LENGTH: 215
<212> TYPE: PRT
<213> ORGANISM: Artificial Sequence
<220> FEATURE:
<223> OTHER INFORMATION: TPP2009 , hIgG, Light_Chain

<400> SEQUENCE: 51

Ala Gln Ser Val Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Tyr
            20                  25                  30

Ala Ser Trp Tyr Gln Gln Lys Pro Gly Gln Ala Pro Val Leu Val Ile
        35                  40                  45

Tyr Gly Lys Asn Asn Arg Pro Ser Gly Ile Pro Asp Arg Phe Ser Gly
```

Ser Ser Ser Gly Asn Thr Ala Ser Leu Thr Ile Thr Gly Ala Gln Ala
65                  70                  75                  80

Glu Asp Glu Ala Asp Tyr Tyr Cys Asn Ser Arg Asp Ser Ser Gly Asn
                85                  90                  95

His Leu Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Gly Ser Pro Val Lys Ala
145                 150                 155                 160

Gly Val Glu Thr Thr Lys Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Ala Glu Cys Ser
    210                 215

<210> SEQ ID NO 52
<211> LENGTH: 454
<212> TYPE: PRT
<213> ORGANISM: Artificial Sequence
<220> FEATURE:
<223> OTHER INFORMATION: TPP2009, hIgG, Heavy_chain

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Arg Met Gly Trp Val Arg Gln Ala Pro Gly Lys Gly Leu Glu Trp Val
        35                  40                  45

Ser Arg Ile Tyr Ser Ser Gly Gly Arg Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Ala Ser Asp Leu Ser Gly Ser Phe Ser Glu Ala Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys

-continued

```
                195                 200                 205
Asn Val Asn His Lys Pro Ser Asn Thr Lys Val Asp Lys Lys Val Glu
            210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly
    450

<210> SEQ ID NO 53
<211> LENGTH: 216
<212> TYPE: PRT
<213> ORGANISM: Artificial Sequence
<220> FEATURE:
<223> OTHER INFORMATION: TPP-2015, hIgG, light_chain

<400> SEQUENCE: 53

Ala Gln Asp Ile Gln Met Thr Gln Ser Pro Gly Thr Leu Ser Leu Ser
1               5                   10                  15
Pro Gly Glu Arg Ala Thr Leu Ser Cys Arg Ala Ser Gln Ser Val Ser
            20                  25                  30
Ser Ser Tyr Leu Ala Trp Tyr Gln Gln Lys Pro Gly Gln Ala Pro Arg
        35                  40                  45
Leu Leu Ile Tyr Gly Ala Ser Ser Arg Ala Thr Gly Ile Pro Asp Arg
    50                  55                  60
Phe Ser Gly Ser Gly Ser Gly Thr Asp Phe Thr Leu Thr Ile Ser Arg
65                  70                  75                  80
Leu Glu Pro Glu Asp Phe Ala Val Tyr Tyr Cys Gln Gln Tyr Gly Ser
                85                  90                  95
Ser Arg Thr Phe Gly Gln Gly Thr Lys Val Glu Ile Arg Arg Thr Val
```

```
                100                 105                 110
Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
210                 215
```

<210> SEQ ID NO 54
<211> LENGTH: 453
<212> TYPE: PRT
<213> ORGANISM: Artificial Sequence
<220> FEATURE:
<223> OTHER INFORMATION: TPP-2015, hIgG, heavy_chain

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Lys Met Asp Trp Val Arg Gln Ala Pro Gly Lys Gly Leu Glu Trp Val
            35                  40                  45

Ser Arg Ile Gly Pro Ser Gly Gly Lys Thr Met Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Lys Ala Ser Asp Leu Ser Gly Thr Tyr Ser Glu Ala Leu
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
```

-continued

```
                245                 250                 255
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Gly
                450

<210> SEQ ID NO 55
<211> LENGTH: 216
<212> TYPE: PRT
<213> ORGANISM: Artificial Sequence
<220> FEATURE:
<223> OTHER INFORMATION: TPP-2016, hIgG, light_chain, Kappa

<400> SEQUENCE: 55

Ala Gln Asp Ile Gln Met Thr Gln Ser Pro Ala Thr Leu Ser Val Ser
1               5                   10                  15

Pro Gly Glu Arg Ala Thr Leu Ser Cys Arg Ala Ser Gln Asn Ile Asn
                20                  25                  30

Arg Asn Leu Ala Trp Tyr Gln Gln Lys Pro Gly Arg Ala Pro Arg Leu
            35                  40                  45

Leu Ile His Thr Ala Ser Thr Arg Ala Pro Gly Val Pro Val Arg Ile
        50                  55                  60

Thr Gly Ser Gly Ser Gly Thr Glu Phe Thr Leu Thr Ile Ser Ser Leu
65                  70                  75                  80

Glu Pro Glu Asp Phe Ala Val Tyr Phe Cys Gln Gln Tyr Ala Ser Pro
                85                  90                  95

Pro Arg Thr Phe Gly Gln Gly Thr Lys Val Glu Ile Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
```

```
            145                 150                 155                 160
Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
    210                 215

<210> SEQ ID NO 56
<211> LENGTH: 454
<212> TYPE: PRT
<213> ORGANISM: Artificial Sequence
<220> FEATURE:
<223> OTHER INFORMATION: TPP-2016, hIgG, heavy_chain

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
                20                  25                  30

Arg Met Asp Trp Val Arg Gln Ala Pro Gly Lys Gly Leu Glu Trp Val
            35                  40                  45

Ser Arg Ile Gly Pro Ser Gly Gly Lys Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Thr Ser Asp Leu Ser Gly Ser Tyr Ser Glu Ala Leu
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
```

```
                290                 295                 300
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly
    450

<210> SEQ ID NO 57
<211> LENGTH: 218
<212> TYPE: PRT
<213> ORGANISM: Artificial Sequence
<220> FEATURE:
<223> OTHER INFORMATION: TPP-2019, hIgG, light_chain, Kappa

<400> SEQUENCE: 57

Ala Gln Asp Ile Gln Met Thr Gln Ser Pro Ala Thr Leu Ser Leu Ser
1               5                   10                  15

Pro Gly Glu Arg Ala Thr Leu Ser Cys Arg Ala Ser Gln Arg Val Ser
                20                  25                  30

Ser Ser Tyr Leu Thr Trp Tyr Gln Gln Lys Pro Gly Gln Ala Pro Arg
                35                  40                  45

Leu Leu Ile Tyr Gly Ala Ser Ser Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Tyr Asp Ser
                85                  90                  95

Thr Pro Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
```

Val Thr Lys Ser Phe Asn Arg Gly Glu Cys
    210                 215

<210> SEQ ID NO 58
<211> LENGTH: 455
<212> TYPE: PRT
<213> ORGANISM: Artificial Sequence
<220> FEATURE:
<223> OTHER INFORMATION: TPP-2019, hIgG, heavy_chain

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Tyr Trp Val Arg Gln Ala Pro Gly Lys Gly Leu Glu Trp Val
        35                  40                  45

Ser Arg Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ser Gln Thr Gly Tyr Tyr Pro His Tyr His Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro

```
                    340                 345                 350
Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly
    450                 455

<210> SEQ ID NO 59
<211> LENGTH: 214
<212> TYPE: PRT
<213> ORGANISM: Artificial Sequence
<220> FEATURE:
<223> OTHER INFORMATION: TPP-2803, hIgG2, light_chain, lambda

<400> SEQUENCE: 59

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210

<210> SEQ ID NO 60
<211> LENGTH: 450
<212> TYPE: PRT
```

<213> ORGANISM: Artificial Sequence
<220> FEATURE:
<223> OTHER INFORMATION: TPP-2803, hIgG2, heavy_chain

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Arg Ile Tyr Ser Ser Gly Gly Arg Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Ala Ser Asp Leu Ser Gly Ser Phe Ser Glu Ala Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

-continued

```
385                 390                 395                 400
Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450
```

MONOCLONAL ANTIBODIES AGAINST ANTITHROMBIN BETA

CROSS-REFERENCES TO RELATED APPLICATIONS

This application is a continuation of U.S. patent application Ser. No. 14/770,222, filed Aug. 25, 2015, which is a National Stage application of International Application No. PCT/US2014/029541, filed Mar. 14, 2014, which claims the benefit of U.S. Provisional Patent Application No. 61/784,590, filed Mar. 14, 2013, the entire disclosure of each of which are hereby incorporated by reference in their entirety.

SUBMISSION OF SEQUENCE LISTING ON ASCII TEXT FILE

The present application includes a Sequence Listing in electronic format as a txt file titled "599582000601seqlist.txt" which was recorded on Feb. 28, 2018 and which has a size of 66 kilobytes (KB). The contents of txt file "599582000601seqlist.txt" are incorporated by reference herein.

BACKGROUND

Current unmet medical needs in the hemophilia field are mainly: (1) treatment of hemophilia patients with inhibitors (~30% of hemophilia patients); and (2) long acting and efficacious coagulant factors (FVIII/FIX) and/or their replacement (bypass drugs) (WFH report 2012, Paris). The most widely used bypass drug for treating hemophilia patients with inhibitors is rFVII, which has major drawbacks such as risk of thrombogenicity, short half-life in plasma and high production cost. Antibodies against anti-coagulant factors, such as Tissue Factor Protein Inhibitor (TFPI), APC (Activated Protein C) and Antithrombin (AT) represent a new treatment paradigm. These antibodies not only bypass or reduce the need for FVIII or FIX coagulation factors in hemophilia patients with inhibitors, but also exhibit longer plasma half-life (which reduces the dosing frequency) and, thus, increases patient compliance. To date, there have been several antibody-based procoagulant drugs at the preclinical development or research stage, such as anti-TFPI and anti-APC.

AT is a major anticoagulant in human plasma. It inhibits thrombin, FXa and other serine proteases functioning in the coagulation pathway. It consists of 432 amino acids, is produced by the liver hepatocyte and has a long plasma half-life of three days (Cotten, Schetz et al. 1977). The amino acid sequence of AT is well-conserved and the homology among cow, sheep, rabbit, mouse and human is 84%-89% (Olson and Bjork 1994). Although the primary physiological targets of AT are thrombin and FXa, AT also inhibits FIXa, FXIa, FXIIa, as well as FVIIa to a lesser extent. AT exerts its inhibition together with heparin. In presence of heparin the inhibition rate of thrombin and FXa by AT increases by 3 to 4 orders of magnitude from $7\text{-}11\times10^3 M^{-1} s^{-1}$ to $1.5\text{-}4\times10^7 M^{-1} s^{-1}$ and from $2.5\times10^{-3} M^{-1} s^{-1}$ to $1.25\text{-}2.5 M^{-1} s^{-1}$ respectively (Olson, Swanson et al. 2004).

Unlike TFPI and APC which inhibit coagulation solely at the initiating stage and the amplification stage respectively, AT exerts its inhibition on coagulation at both the initiation and amplification stage. Therefore, blocking AT could have more potent pro-coagulant effect than blocking either TFPI or APC alone. Decreased AT levels and activity have been shown to correlate with increased thrombosis in human. Patients with AT deficiency tend to show recurrent venous thrombosis and pulmonary embolisms (van Boven and Lane 1997). Furthermore, homozygous AT knockout mice die in the embryonic stage with an extreme hypercoagulable state (Ishiguro, Kojima et al. 2000). A recent study shows that heterozygous AT knockout hema mice in which AT is reduced by 50% significantly have less blood loss and enhanced thrombin generation in a tail-clip bleeding model (Bolliger, Szlam et al. 2010).

AT is a glycoprotein with two isoforms based on differential glycosylation on Asn135, ATα and ATβ (Bjork 1997). ATβ lacks glycosylation at Asn135 and is a minor glycoisoform representing 10% of human plasma AT. Asn135 is located adjacent to the initial heparin attachment site and constitutes part of extended heparin binding site after allosteric activation and D helix extension (dela. Cruz, Jairajpuri et al. 2006). The lack of bulky-sized glycan at Asn135 affects ATβ activation profoundly in two ways: 1) a faster allosteric activation upon heparin binding required for inhibition of FXa and FIXa; and 2) extra accessible binding sites for higher affinity heparin binding for inhibition of FXa and thrombin by a bridging mechanism. Indeed, under physiological salt concentration, plasma-derived ATβ binds to heparin with a $K_D$ of 36+/−3 nm while ATα binds to heparin with a $K_D$ of 500+/−50 nm (Turk I V. et al., 1993). The higher affinity of ATβ for heparin leads to its preferential distribution to the sub-endothelial layer which is enriched in the heparin-like structure—glycosaminoglycan. Consequently, ATβ is proposed to play a major and potent role in inhibition of FXa and thrombin at the vascular injury sites (Carlson and Atencio 1982; McCoy A J, Pei X Y, et al. 2003; Turk B, Brieditis I. et al. 1997; Witmer M R, Hatton M W. 1991; Frebelius S, et al. 1996). The importance and stronger potency of ATβ relative to that of ATα is also reported in clinical studies. In patients, the severity of AT homozygous mutations defective in heparin-binding is ameliorated by the beta form of AT (Martinez-Martinez, Navarro-Fernandez et al. 2012). In another study, a borderline level (~70% of normal AT antigen and activity) of AT is compensated by the 20%~30% ATβ in plasma (Bayston, Tripodi et al. 1999).

SUMMARY

Monoclonal antibodies to human ATβH (ATβ complexed with heparin and/or heparin-like structure) are provided. In at least one embodiment, the anti-ATβH monoclonal antibodies exhibit binding to ATβ complexed with Heparin.

In other embodiments, the monoclonal antibodies to ATβH may be optimized, for example to have increased affinity or increased functional activity. Also provided are specific epitopes that may be on human ATβH and are bound by an isolated monoclonal antibody. Further provided are the isolated nucleic acid molecules encoding the same.

Pharmaceutical compositions comprising the anti-ATβH monoclonal antibodies and methods of treatment of genetic and acquired deficiencies or defects in coagulation such as hemophilia A and B are also provided.

Also provided are methods for shortening bleeding time by administering an anti-ATβH monoclonal antibody to a patient in need thereof. Methods for producing a monoclonal antibody that binds human ATβH are also provided.

BRIEF DESCRIPTION OF THE DRAWINGS

The skilled artisan will understand that the drawings, described below, are for illustration purposes only. The drawings are not intended to limit the scope of the present teachings or claims in any way.

Figure 6A:
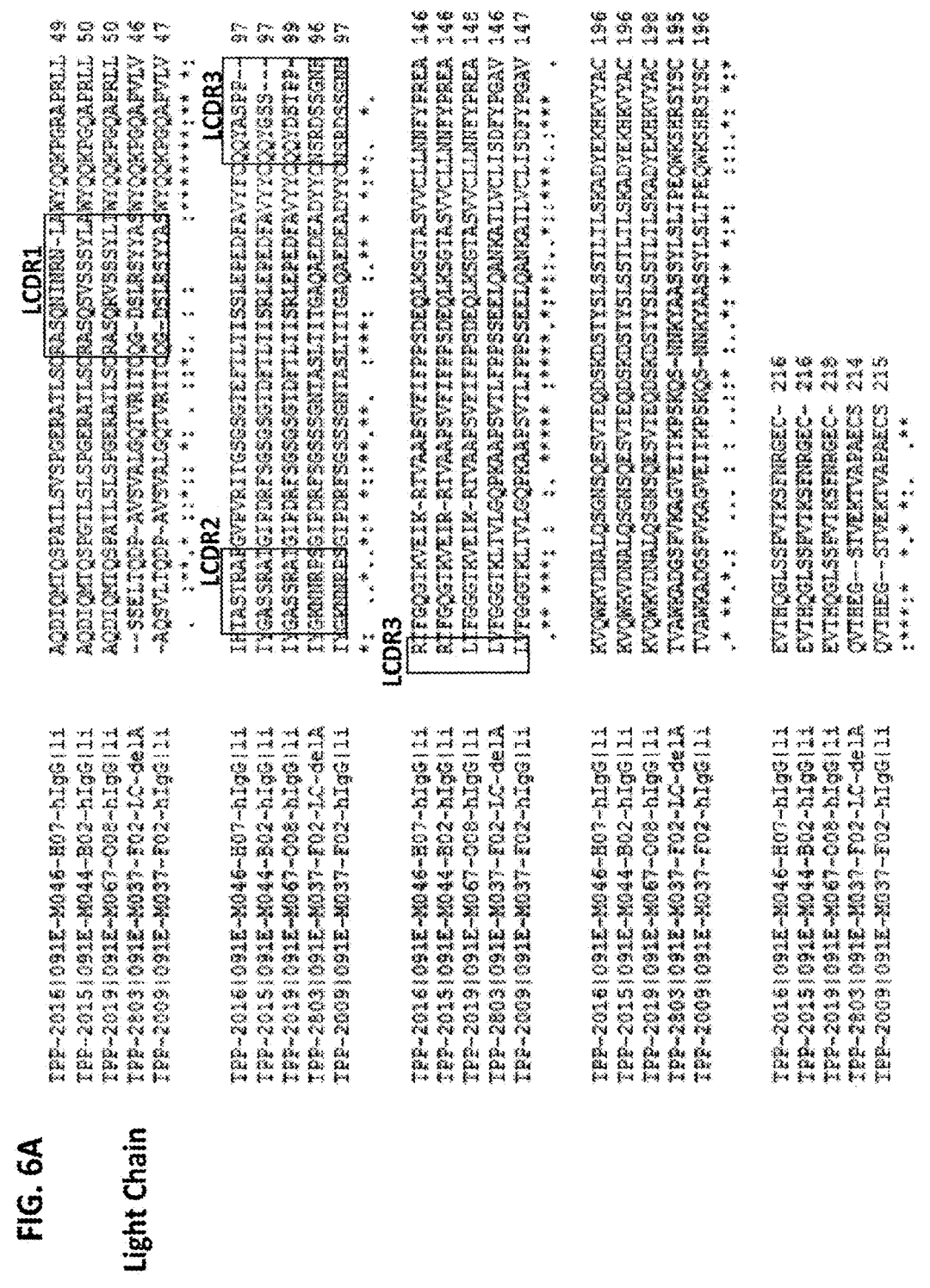

FIGS. 6A and 6B shows alignment of the amino acid sequences of the light chain domain and heavy chain domain, respectively, of antibodies TPP-2009 (SEQ ID NO:1 and SEQ ID NO: 2, respectively), TPP-2015 (SEQ ID NO:3 and SEQ ID NO:4, respectively), TPP-2016 (SEQ ID NO:5 and SEQ ID NO:6 respectively), TPP-2019 (SEQ ID NO:7 and SEQ ID NO:8, respectively), and TPP-2803 (SEQ ID NO:9 and SEQ ID NO:10, respectively).

FIGS. 7A-7C show antibody binding specificity determined by Biacore (FIG. 7A) and ELISA (FIG. 7B) tests, and antibody binding affinity to human AtβH (FIG. 7C).

FIG. 8B is a table showing antibodies shorten clotting time in human HemA plasma and in human AT-deficient plasma spiked in with Atβ or Atα.

FIGS. 10A and 10B show an experimental protocol for a tail vein transection (TVT) model in HemA and the efficacy of antibody TPP-2009 in the TVT model in HemA mice. FIG. 10B shows the antibody TPP-2009 has potent efficacy in the Tail Vein Transection (TVT) model of HemA mice.

DETAILED DESCRIPTION

Figure 1:
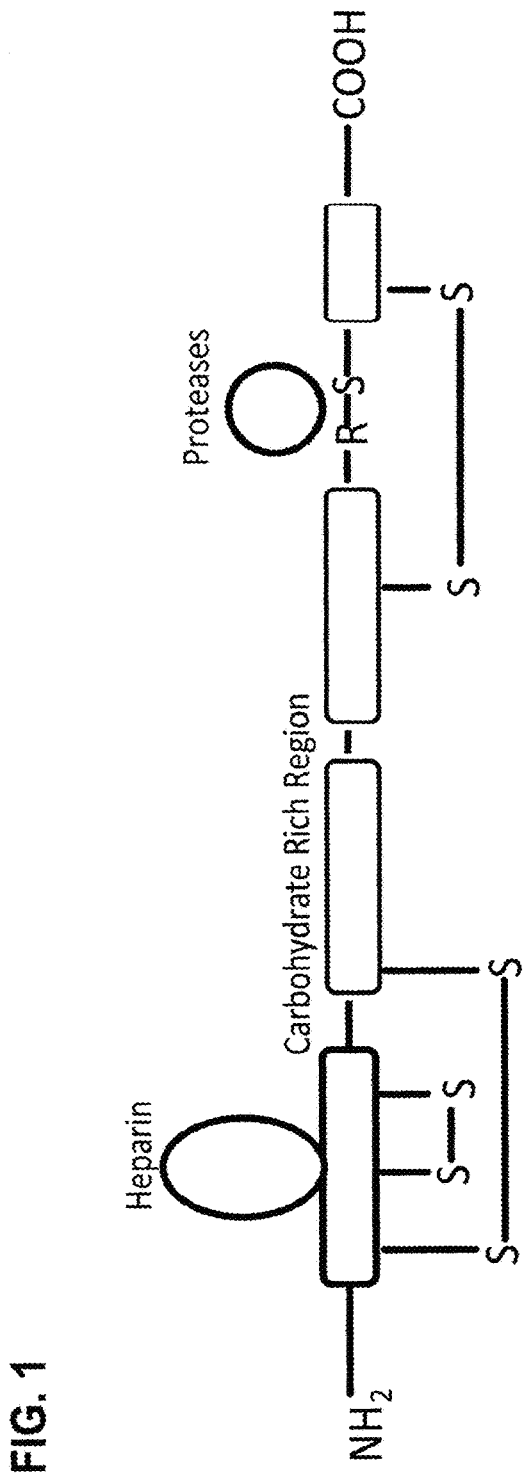
FIG. 1 shows a schematic representation of ATβ bound to heparin and the various binding domains of ATβ.
Figure 2A:
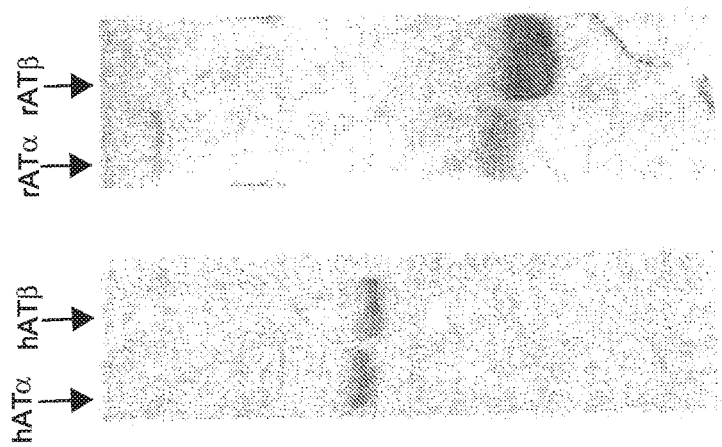
FIGS. 2A-2C show how ATβ is distinguished from ATα by lacking of one N-glycan.
Figure 2B:
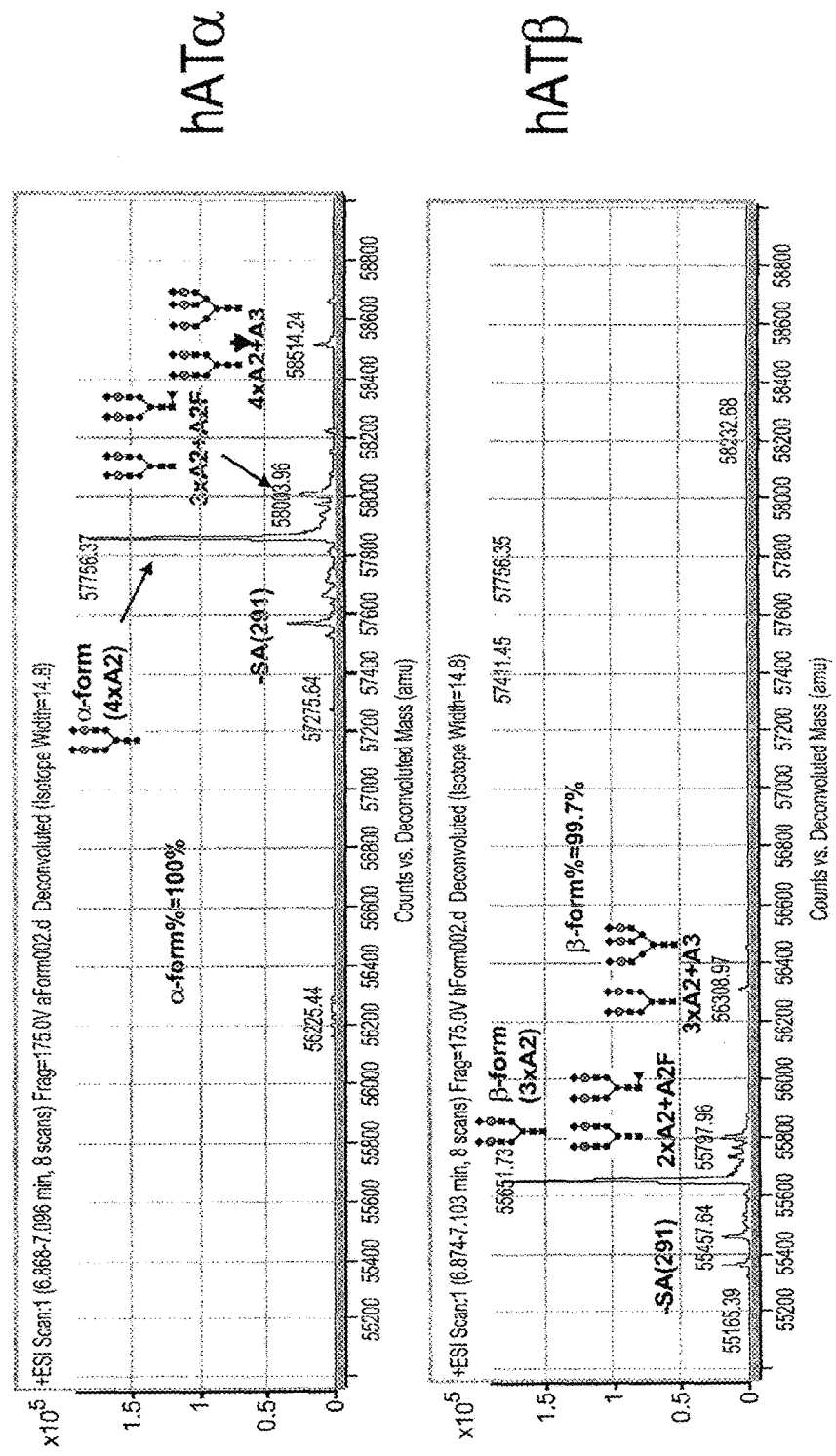
Figure 2C:
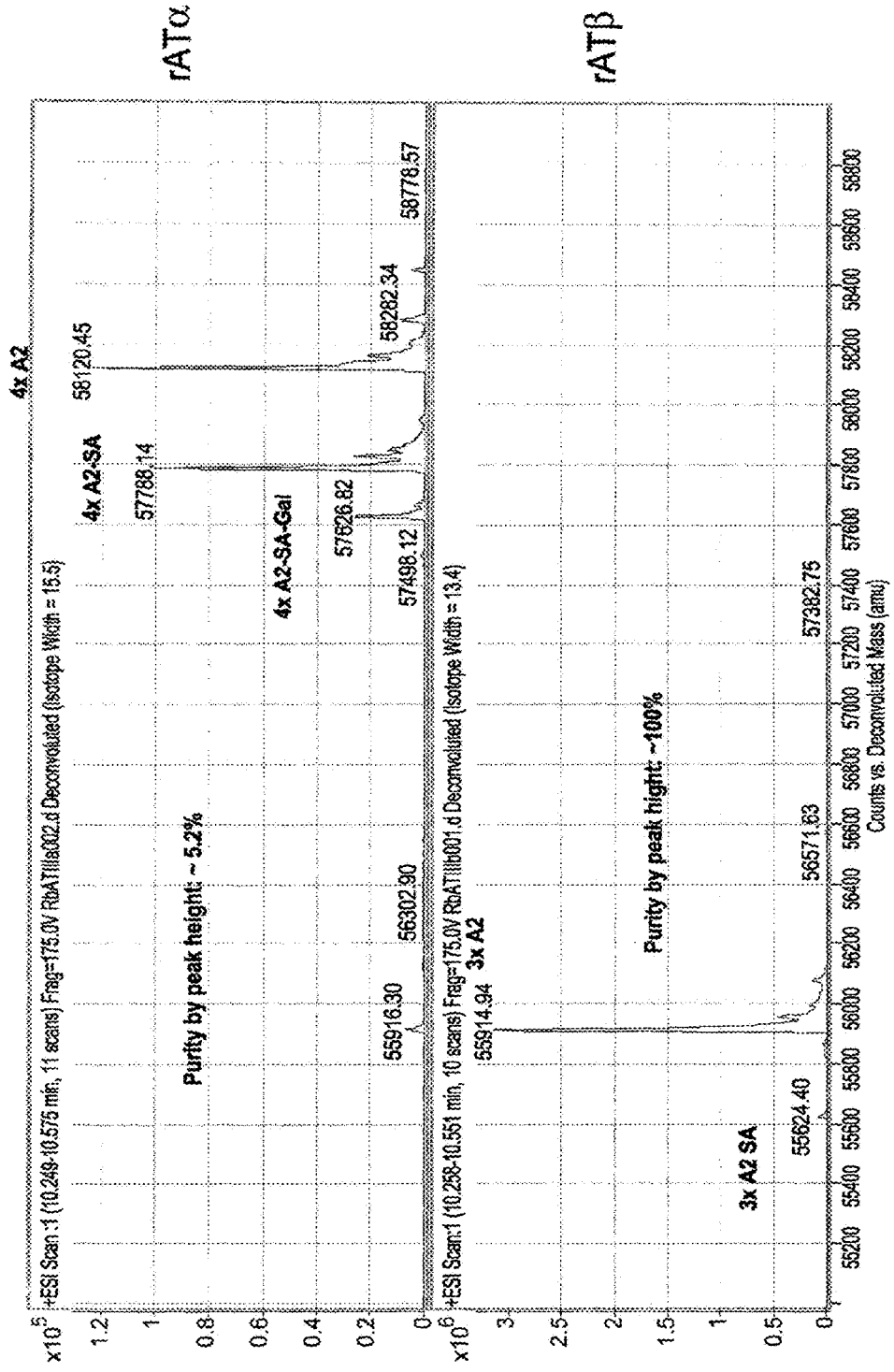
Figure 3A:
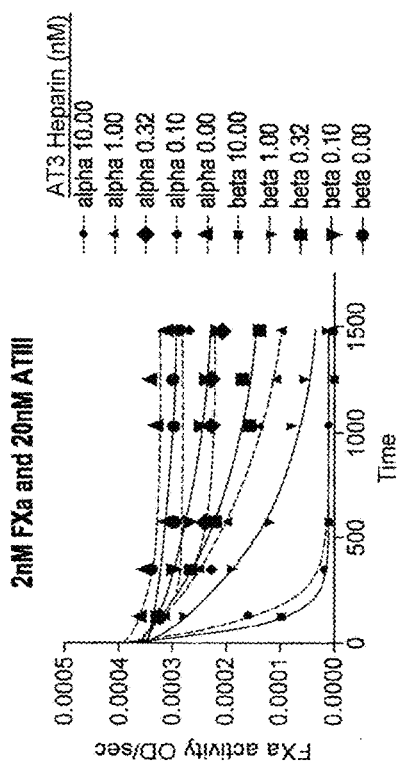
FIGS. 3A-3D show ATβ with faster binding to heparin and more potent inhibition than ATα.
Figure 3B:
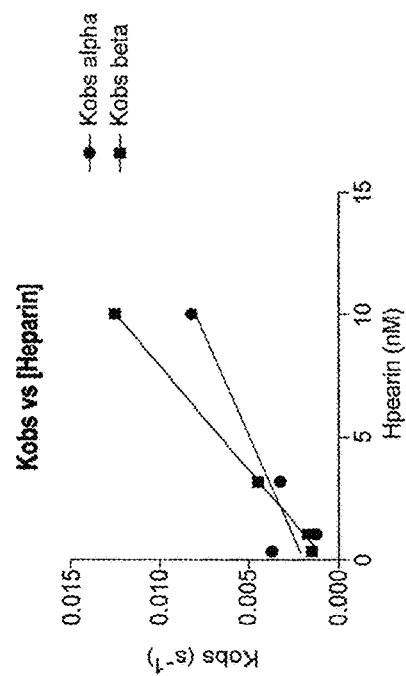
Figure 3C:
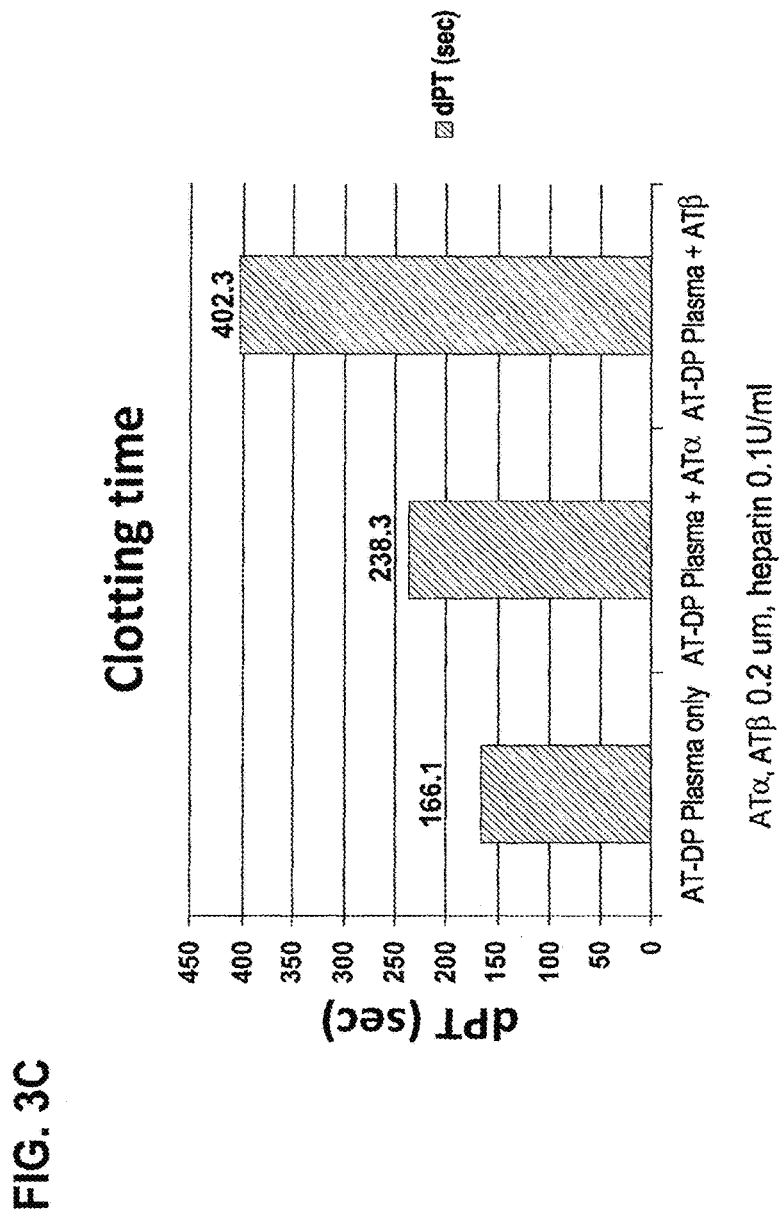
Figure 3D:
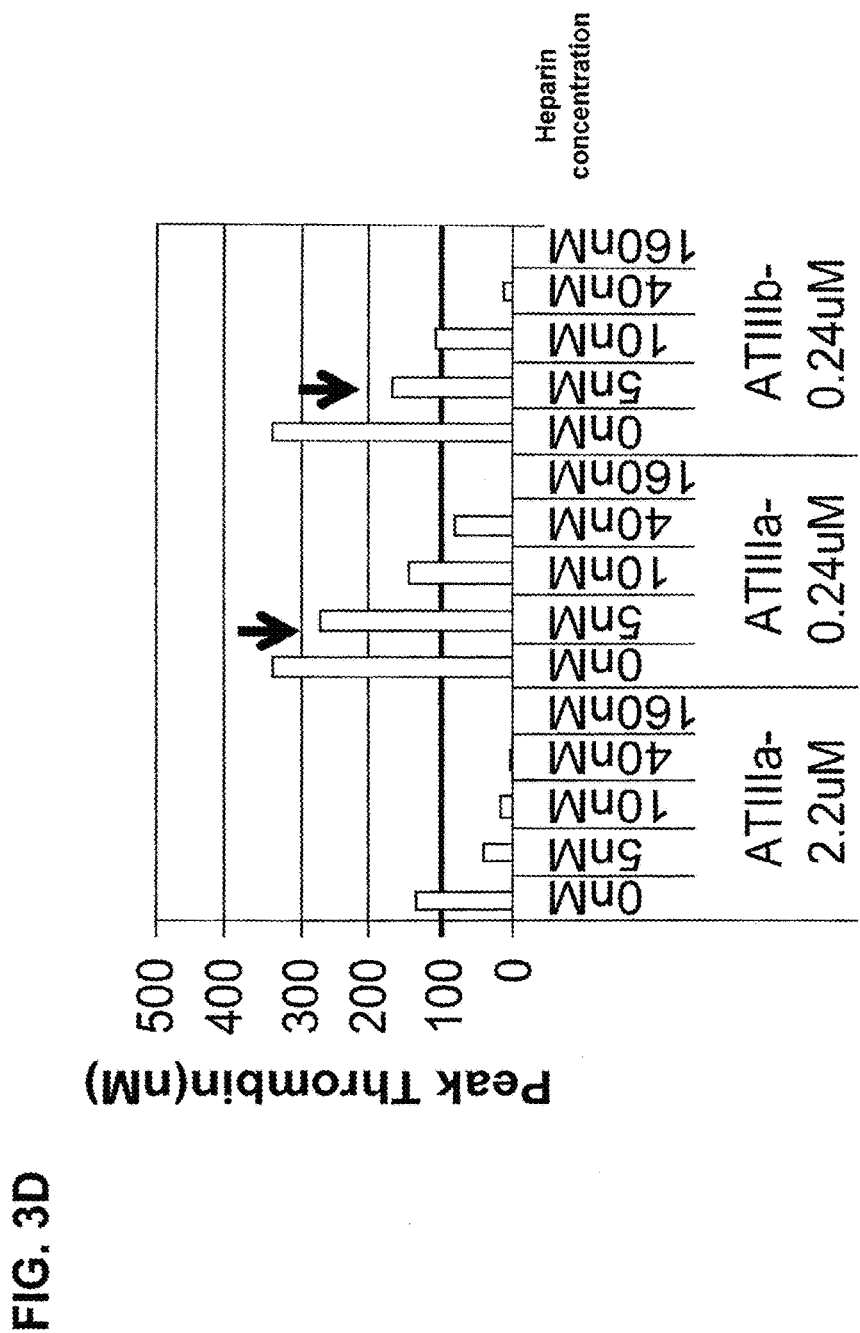
Figure 4A:
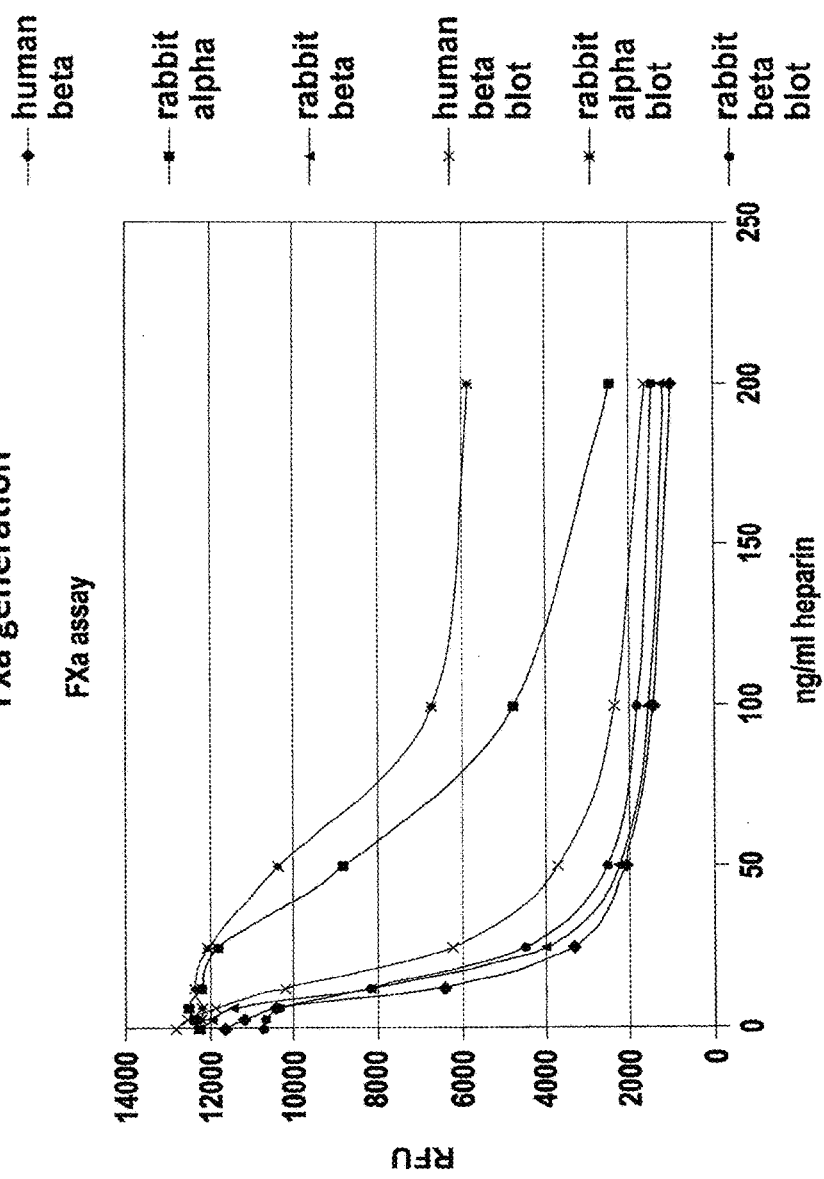
FIG. 4A shows biotinlayted hAT and rAT are functional in inhibition of Fxa generation (FIG. 4A).
Figure 4B:
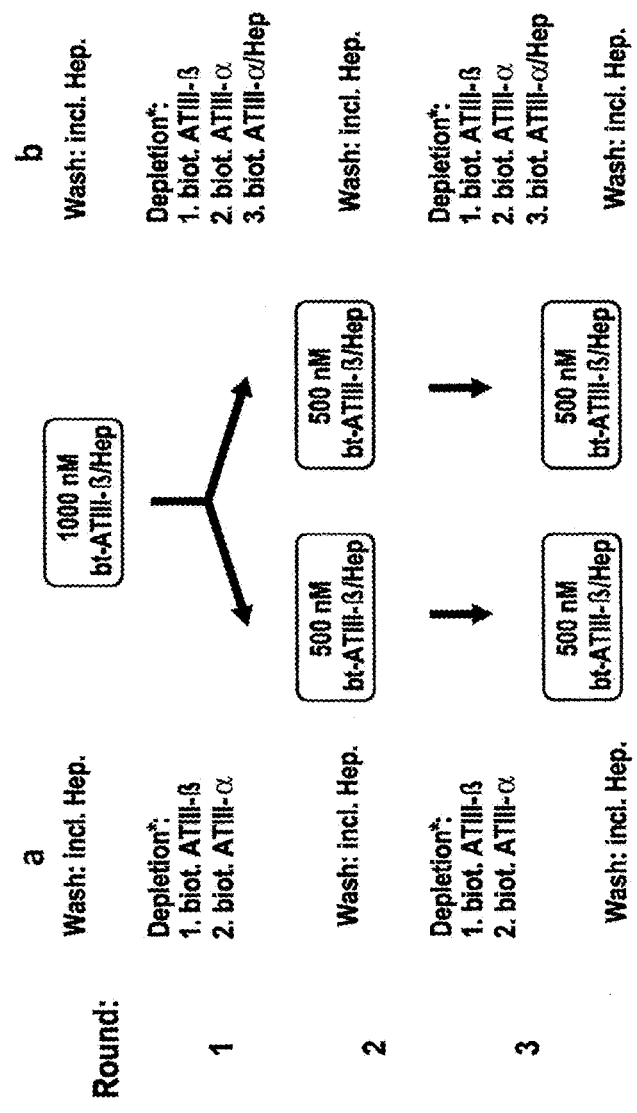
FIGS. 4B-4C show various strategies for antibody discovery by phage display.
Figure 4C:
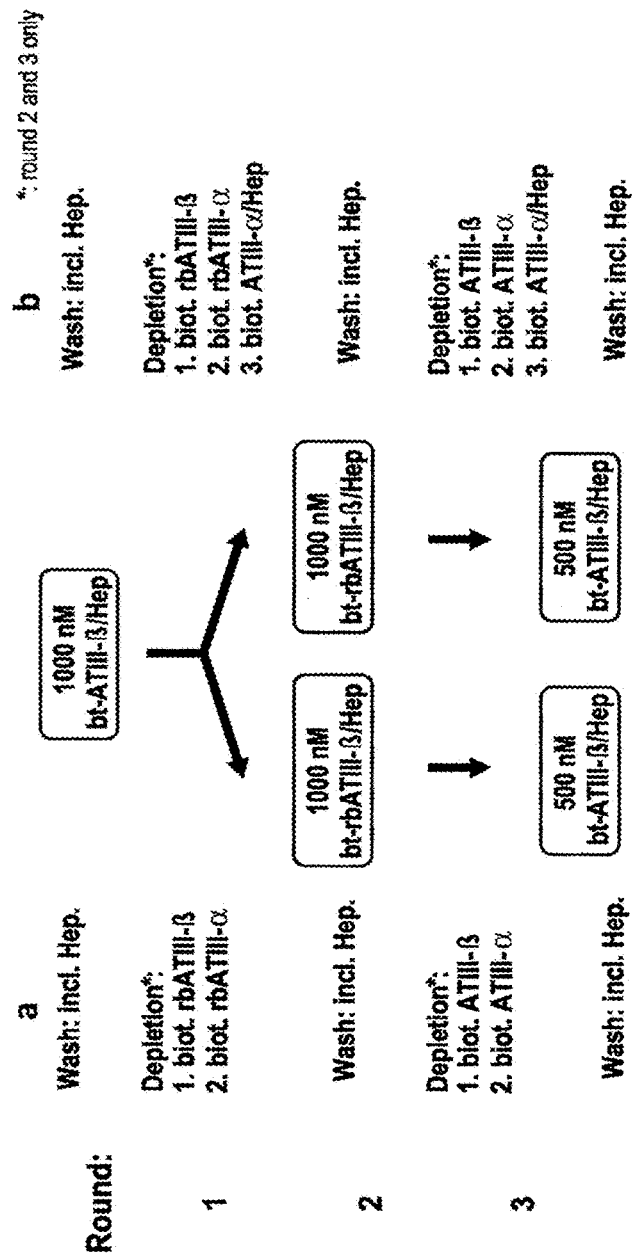
Figure 5:
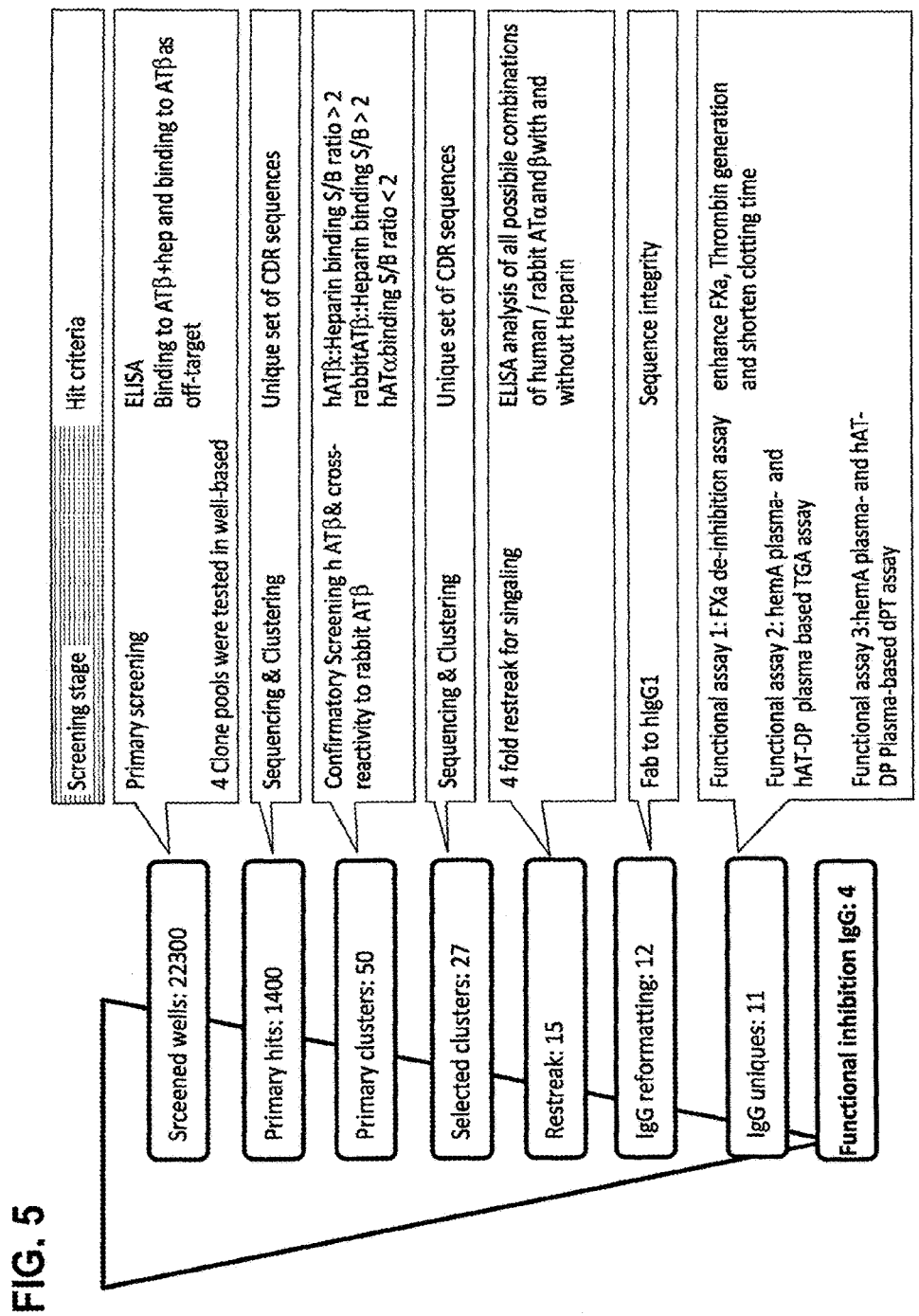
FIG. 5 shows a screening method for identifying antibodies capable of functional inhibition of ATβ::heparin.
Figure 7A:
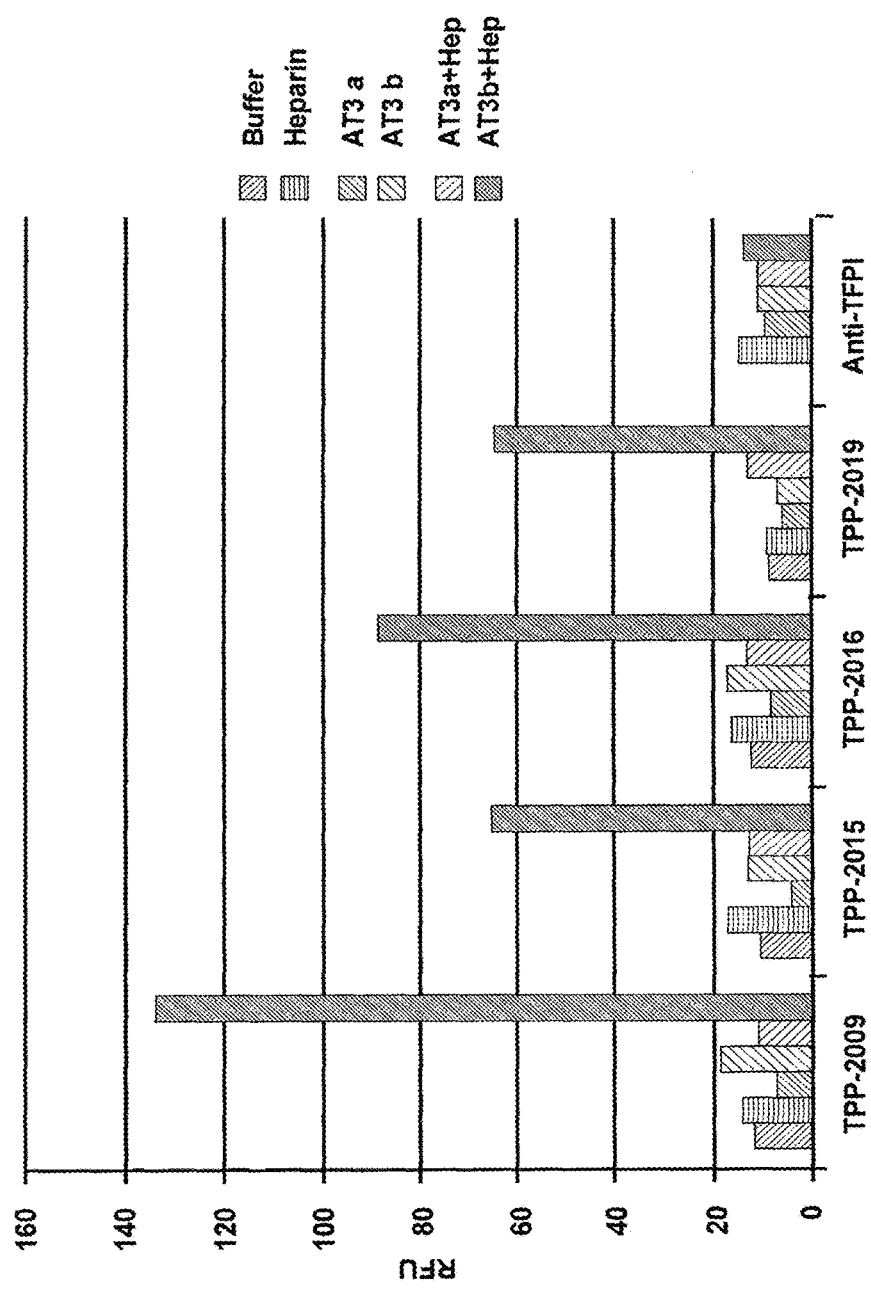
Figure 7B:
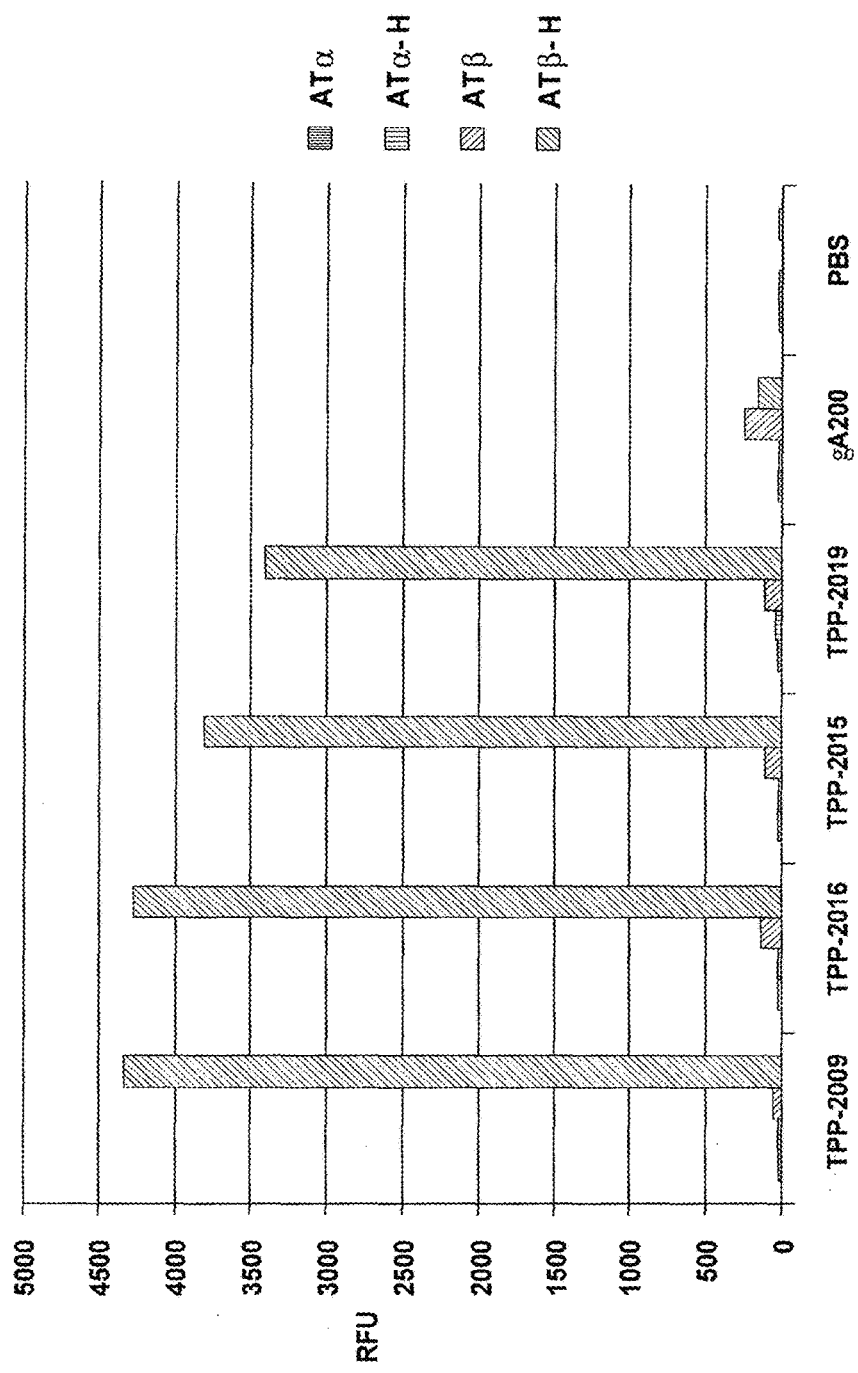
Figure 8A:
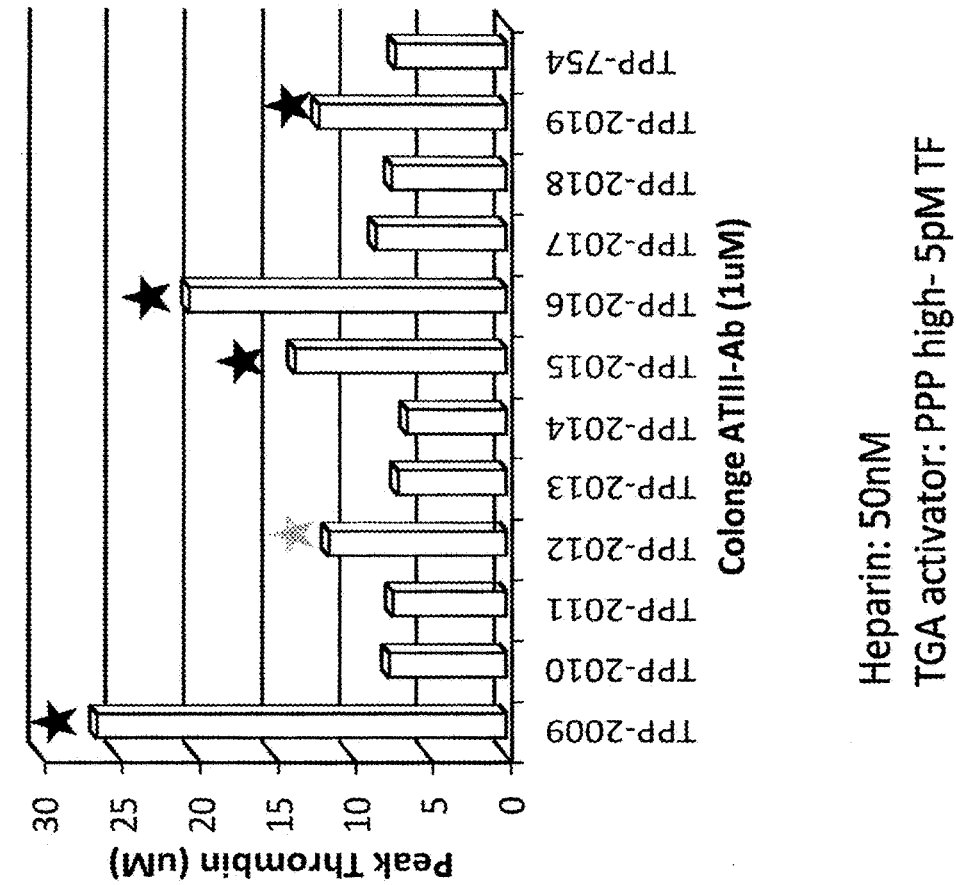
FIG. 8A is a graphical representation of the effect of TPP antibodies on thrombin generation in human HEM-A plasma, and illustrates that antibody presence increases peak thrombin generation in human HEM-A plasma.
Figure 9:
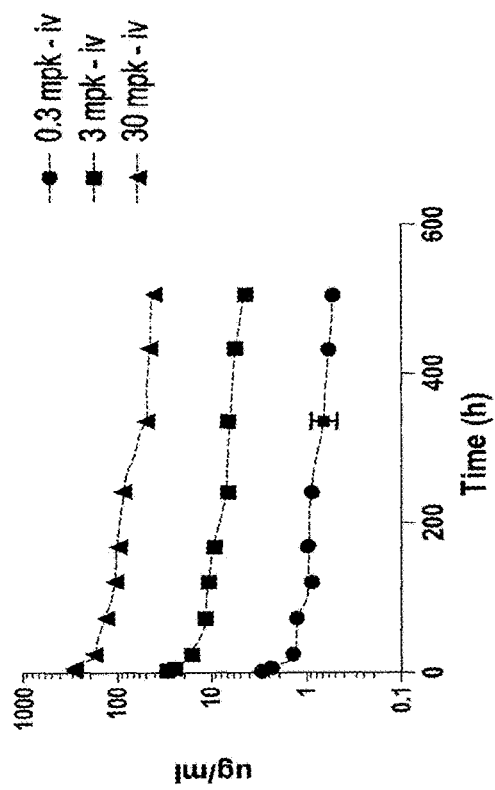
FIG. 9 is a graphical representation of the PK of antibody TPP 2009 in HEM-A mice using IV dosing at 0.3, 3 and 30 mg/kg, three mice per time point (10 time points over 21 days), and associated PK parameters.

This disclosure provides antibodies, including monoclonal antibodies and other binding proteins that specifically bind to the activated form of ATβ, but exhibit comparatively little or no reactivity against the ATα form, either naïve or activated.

Definitions

For the purpose of interpreting this specification, the following definitions will apply. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

Whenever appropriate, terms used in the singular will also include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and are not limiting. The terms "such as," "for example," and "e.g." also are not intended to be limiting. For example, the term "including" shall mean "including, but not limited to."

As used herein, the term "about" refers to +/−10% of the unit value provided. As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result because of the many variables that affect testing, production, and storage of biological and chemical compositions and materials, and because of the inherent error in the instruments and equipment used in the testing, production, and storage of biological and chemical compositions and materials. The term substantially is therefore used herein to capture the potential lack of completeness inherent in many biological and chemical phenomena.

The term "ATβ" or "ATβH" as used herein refers to any variant, isoform, and/or species homolog of AT in its form that is naturally expressed by cells and present in plasma and is distinct from ATα. Further, the term "ATβ" or "ATβH" as used herein can also refer to an activated form of ATβ complexed with heparin or a heparin-like structure.

The term "antibody" as used herein refers to a whole antibody and any antigen binding fragment (i.e., "antigen-binding portion") or single chain thereof. This term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-ATβH monoclonal antibody fragment binds to an epitope of ATβH. The antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VII and CH1 domains; (iv) a Fv fragment consisting of the VL and VH domains of a single arm of an antibody; (v) a dAb fragment (Ward et al., (1989) Nature 341:544-546), which consists of a $V_H$ domain; (vi) an isolated complementarily determining region (CDR); (vii) minibodies, diabodies, triabodies, tetrabodies, and kappa bodies (see, e.g., Ill et al., Protein Eng 1997; 10:949-57); (viii) camel IgG; and (ix) IgNAR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al (1988) Proc. Natl. Acad. Sci. USA 85:5879-5883). Such single chain antibodies are also encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment can be encompassed in an antibody mimetic. The term "antibody mimetic" or "mimetic" as used herein refers to a protein that exhibits binding activity similar to a particular antibody but is a smaller alternative antibody or a non-antibody protein. Such antibody mimetic can be comprised in a scaffold. The term "scaffold" refers to a polypeptide platform for the engineering of new products with tailored functions and characteristics.

The term "anti-ATβ antibody" as used herein refers to an antibody that specifically binds to an epitope of ATβ associated with heparin or heparin-like. When bound in vivo to an epitope of ATβH, the anti-ATβ antibodies disclosed herein augment one or more aspects of the blood clotting cascade.

The terms "inhibits binding" and "blocks binding" (e.g., referring to inhibition/blocking of binding of ATβ substrate to ATβH) as used herein are used interchangeably and encompass both partial and complete inhibition or blocking of a protein with its substrate, such as an inhibition or blocking by at least about 10%, about 20%, about 30%, about 40%, about 50%, about 60%, about 70%, about 80%, about 90%, about 95%, about 96%, about 97%, about 98%, about 99%, or about 100%.

In reference to the inhibition and/or blocking of binding of ATβ substrate to ATβ, the terms inhibition and blocking also include any measurable decrease in the binding affinity of ATβ and/or ATβH to a physiological substrate when in contact with an anti-ATβ antibody as compared to ATβ not in contact with an anti-ATβ antibody, e.g., the blocking of the interaction of ATβ with its substrates by at least about 10%, about 20%, about 30%, about 40%, about 50%, about 60%, about 70%, about 80%, about 90%, about 95%, about 96%, about 97%, about 98%, about 99%, or about 100%.

The terms "monoclonal antibody" or "monoclonal antibody composition" as used herein refer to antibody molecules of single Molecular composition. A monoclonal antibody composition displays a single binding specificity and affinity for a particular epitope. Accordingly, the term "human monoclonal antibody" as used herein refers to antibodies displaying a single binding specificity that have variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo).

The term "isolated antibody" as used herein is intended to refer to an antibody which is substantially free of other biological molecules, including antibodies having different antigenic specificities (e.g., an isolated antibody that binds to ATβH is substantially free of antibodies that bind antigens other than ATβH). In some embodiments, the isolated antibody is at least about 75%, about 80%, about 90%, about 95%, about 97%, about 99%, about 99.9% or about 100% pure by dry weight. In some embodiments, purity can be measured by a method such as column chromatography, polyacrylamide gel electrophoresis, or HPLC analysis. An isolated antibody that binds to an epitope, isoform or variant of human ATβH can, however, have cross-reactivity to other related antigens, e.g., from other species (e.g., ATβH species homologs). Moreover, an isolated antibody can be substantially free of other cellular material and/or chemicals.

The term "specific binding" as used herein refers to antibody binding to a predetermined antigen. An antibody that exhibits specific binding typically binds to an antigen with an affinity of at least about $10^5$ $M^{-1}$ and binds to that antigen with an affinity that is higher, for example at least two-fold greater, than its binding affinity for an irrelevant antigen (e.g., BSA, casein). The phrases "an antibody recognizing an antigen" and "an antibody specific for an antigen" are used interchangeably herein with the term "an antibody which binds specifically to an antigen." As used herein, the term "minimal binding" refers to an antibody that does not bind to and/or exhibits low affinity to a specified antigen. Typically, an antibody having minimal binding to an antigen binds to that antigen with an affinity that is lower than about $10^2$ $M^{-1}$ and does not bind to a predetermined antigen with higher affinity than it binds to an irrelevant antigen.

When used herein for an antibody such as an IgG antibody, the term "high affinity" refers to a binding affinity of at least about $10^7$ $M^{-1}$, in at least one embodiment at least about $10^8$ $M^{-1}$, in some embodiments at least about $10^9$ $M^{-1}$, about $10^{10}$ $M^{-1}$, about $10^{11}$ $M^{-1}$ or greater, e.g., up to about $10^{13}$ $M^{-1}$ or greater. However, "high affinity" binding can vary for other antibody isotypes. For example, "high affinity" binding for an IgM isotype refers to a binding affinity of at least about $10^7$ $M^{-1}$.

The term "isotype" as used herein refers to the antibody class (e.g., IgM or IgG1) that is encoded by heavy chain constant region genes.

The terms "Complementarity-determining region" or "CDR" as used herein refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively [Wu T T, Kabat E A, Bilofsky H, Proc Natl Acad Sci USA. 1975 December; 72(12):5107 and Wu T T, Kabat E A, J Exp Med. 1970 Aug. 1; 132(2):211]. CDRs are involved in antigen-antibody binding, and the CDR3 comprises a unique region specific for antigen-antibody binding. An antigen-binding site, therefore, can include six CDRs, comprising the CDR regions from each of a heavy and a light chain V region. The term "epitope" refers to the area or region of an antigen to which an antibody specifically binds or interacts, which in some embodiments indicates where the antigen is in physical contact with the antibody. Conversely, the term "paratope" refers to the area or region of the antibody on which the antigen specifically binds. Epitopes characterized by competition binding are said to be overlapping if the binding of the corresponding antibodies are mutually exclusive, i.e. binding of one antibody excludes simultaneous binding of another antibody. The epitopes are said to be separate (unique) if the antigen is able to accommodate binding of both corresponding antibodies simultaneously.

The term "competing antibodies" as used herein refers to antibodies that bind to about the same, substantially the same, essentially the same, or even the same epitope as an antibody against ATβH as described herein. Competing antibodies include antibodies with overlapping epitope specificities. Competing antibodies are thus able to effectively compete with an antibody as described herein for binding to ATβH. In some embodiments, the competing antibody can bind to the same epitope as the antibody described herein. Alternatively viewed, the competing antibody has the same epitope specificity as the antibody described herein.

The term "conservative substitutions" as used herein refers to modifications of a polypeptide that involve the substitution of one or more amino acids for amino acids having similar biochemical properties that do not result in loss of a biological or biochemical function of the polypeptide. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, value, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Antibodies of the present disclosure can have one or more conservative amino acid substitutions yet retain antigen binding activity.

For nucleic acids and polypeptides, the term "substantial homology" as used herein indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, in some embodiments about 90%, about 91%, about 92%, about 93%, about 94%, or about 95%, in at least one embodiment at least about 96%, about 97%, about 98%, about 99%, about 99.1%, about 99.2%, about 99.3%, about 99.4%, or about 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein. The percent identity between two sequences is a function of the number of identical positions shared by the sequences (i.e., % homology=# of identical positions/ total # of positions×100), taking into account the number of gaps, and the length of each gap, that need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40. (further details found at http://www.invitrogen.com/site/us/en/home/LINNEA-Online-Guides/LINNEACommunities/Vector-NTI-Community/Sequence-analysis-and-data-management-software-for-PCs/AlignX-Module-for-Vector-NTI-Advance.reg.us.html).

Another method for determining the an overall match between a query sequence (a sequence of the present disclosure) and a subject sequence, also referred to as a global sequence alignment, can be determined using the CLUSTALW computer program (Thompson et al., Nucleic Acids Research, 1994, 2(22): 4673-4680), which is based on the algorithm of Higgins et al., Computer Applications in the Biosciences (CABIOS), 1992, 8(2): 189-191. In a sequence alignment the query and subject sequences are both DNA sequences. The result of said global sequence alignment is in percent identity. Parameters that can be used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters can be used: Gap Opening Penalty=10, Gap Extension Parameter=0.05; Gap Separation Penalty Range=8; % Identity for Alignment Delay=40.

The nucleic acids can be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following can be used: alkaline/SDS treatment, CsCl banding, column chromatography, agarose gel electrophoresis and others well known in the art.

Monoclonal Antibodies Against ATβH

Bleeding disorders where homeostasis is deregulated in hemophilia or in trauma patients where the wound results in a temporary loss of hemostasis, can be treated by AT inhibitors. Antibodies, antigen-binding fragments thereof, and other AT-specific protein scaffolds can be used to provide targeting specificity to inhibit a subset of AT protein functions while preserving the rest. Given the at least 10-fold difference in plasma concentration of ATβ (<12 ug/ml) versus ATα (120 ug/ml), increased specificity of any potential ATβ inhibitor therapeutics is helpful to block ATβ function in the presence of a high circulating excess of ATα. ATβ specific antibodies that block the anti-coagulant function of ATβ can be used as therapeutics for patients with bleeding disorders. Examples of bleeding disorders include hemophilia, hemophilia patients with inhibitors, trauma-induced coagulopathy, severe bleeding patients during sepsis treatment by AT, bleeding resulting from elective surgery such as transplantation, cardiac surgery, orthopedic surgery, and excessive bleeding from Menorrhagia. Anti-ATβH antibodies having long circulating half-live can be useful in treating chronic diseases like hemophilia. ATβH antibody fragments or ATβH-binding protein scaffolds with shorter half-lives can be more effective for acute use (e.g. therapeutic use in trauma), ATβH-binding antibodies were identified by panning and screening human antibody libraries against human ATβ in complex with heparin. The identified antibodies exhibited binding to human ATβH. The heavy chain variable region and light chain variable region of each monoclonal antibody isolated was sequenced and its CDR regions were identified. The sequence identifier numbers ("SEQ ID NO") that correspond to the heavy and light chain variable regions of the ATβH-specific monoclonal antibodies are summarized in Table 1A.

TABLE 1A

Human anti-ATβH (heparin complexed ATβ) antibodies

| Clone | Light Chain variable Region | SEQ ID | Heavy Chain Variable Region | SEQ ID |
|---|---|---|---|---|
| TPP2009 | AQSVLTQDPAVSVALGQTVRIT CQGDSLRSYYASWYQQKPGQ APVLVIYGKNNRPSGIPDRFSGS SSGNTASLTITGAQAEDEADYY CNSRDSSGNHLVFGGGTKLTV LGQPKAAPSVTLFPPSSEELQA NKATLVCLISDFYPGAVTVAW KADGSPVKAGVETTKPSKQSN NKYAASSYLSLTPEQWKSHRS YSCQVTHEGSTVEKTVAPAECS | No. 1 | EVQLLESGGGLVQPG GSLRLSCAASGFTFS AYRMGWVRQAPGK GLEWVSRIYSSGGRT RYADSVKGRFTISRD NSKNTLYLQMNSLR AEDTAVYYCAREKA SDLSGSFSEALDYWG QGTLVTVSS | No. 2 |
| TPP2015 | AQDIQMTQSPGTLSLSPGERAT LSCRASQSVSSSYLAWYQQKP GQAPRLLIYGASSRATGIPDRFS GSGSGTDFTLTISRLEPEDFAVY YCQQYGSSRTFGQGTKVEIRRT VAAPSVFIFPPSDEQLKSGTASV VCLLNNFYPREAKVQWKVDN ALQSGNSQESVTEQDSKDSTYS LSSTLTLSKADYEKHKVYACE VTH QGLSSPVTKS FNRGEC | No. 3 | EVQLLESGGGLVQPG GSLRLSCAASGFTFS KYKMDWVRQAPGK GLEWVSRIGPSGGKT MYADSVKGRFTISRD NSKNTLYLQMNSLR AEDTAVYYCAREKA SDLSGTYSEALDYW GQGTLVTVSS | No. 4 |
| TPP2016 | AQDIQMTQSPATLSVSPGERAT LSCRASQNINRNLAWYQQKPG RAPRLLIHTASTRAPGVPVRITG SGSGTEFTLTISSLEPEDFAVYF CQQYASPPRTFGQGTKVEIKRT VAAPSVFIFPPSDEQLKSGTASV VCLLNNFYPREAKVQWKVDN ALQSGNSQESVTEQDSKDSTYS LSST LTLSKADYEK HKVYACEVTH QGLSSPVTKS FNRGEC | No. 5 | EVQLLESGGGLVQPG GSLRLSCAASGFTFS KYRMDWVRQAPGK GLEWVSRIGPSGGKT TYADSVKGRFTISRD NSKNTLYLQMNSLR AEDTAVYYCAREKT SDLSGSYSBALDYW GQGTL VTVSS | No. 6 |
| TPP2019 | AQDIQMTQSPATTLSLSPGBRAT LSCRASQRVSSSYLTWYQQKP GQAPRLLIYGASSRATGIPDRFS GSGSGTDFTLTISRLEPEDFAVY YCQQYDSTPPLTFGGGTKVEIK RTVAAPSVFIFPPSDEQLKSGTA SVVCLLNNFYPREAKVQWKVD NALQSGNSQESVTEQDSKDST YSLS STLTLSKADYEKHKVYACEVT HQGLSSPVTKSFNRGEC | No. 7 | EVQLLESGGG LVQPGGSLRL SCAASGFTFS RYAMYWVRQA PGKGLEWVSR ISPSGGKTHY ADSVKGRFTI SRDNSKNTLY LQMNSLRAED TAVYYCARLS QTGYYPHYHY YGMDVWGQGT TVTVSS | No. 8 |
| TPP2803 | SSELTQDPAVSVALGQTVRITC QGDSLRSYYASWYQQKPGQAP VLVTYGKNNRPSGIPDRFSGSSS GNTASLTITGAQAEDEADYYC NSRDSSGNHLVFGGGTKLTVL GQPKAAPSVTLFPPSSEELQAN KATLVCLISDFYPGAVTVAWK ADGSPVKAGVETTKPSKQSNN KYAASSYLSLTPEQWKSHRSYS CQVTHEGSTVEKTVAPAECS | No. 9 | EVQLLESGGGLVQPG GSLRLSCAASGFTFSS YRMSWVRQAPGKGL EWVSRIYSSGGRTRY ADSVKGRFTISRDNS KNTLYLQMNSLRAE DTAVYYCAREKASD LSGSFSEALDYWGQ GTLVTVSS | No. 10 |

In at least some possible embodiments, an isolated monoclonal antibody binds to human and inhibits anticoagulant activity, wherein the antibody comprises a heavy chain variable region comprising an amino acid sequence selected from the group consisting of SEQ ID NOS: 2, 4, 6, 8, and 10.

In at least some possible embodiments, an isolated monoclonal antibody binds to human ATβH and inhibits anticoagulant activity, wherein the antibody comprises a light chain variable region comprising an amino acid sequence selected from the group consisting of SEQ ID NOS: 1, 3, 5, 7, and 9.

In at least some possible embodiments an isolated monoclonal antibody binds to human ATβH and inhibits anticoagulant activity, wherein the antibody comprises a heavy chain variable region comprising an amino acid sequence selected from the group consisting of SEQ ID NOS: 2, 4, 6, 8, and 10 and a light chain variable region comprising an amino acid sequence selected from the group consisting of SEQ ID NOS: 1, 3, 5, 7, and 9.

In at least some possible embodiments, the antibody comprises heavy and light chain variable regions comprising:

(a) a heavy chain variable region comprising an amino acid sequence of SEQ ID NO: 2, and a light chain variable region comprising an amino acid sequence of SEQ ID NO: 1;

(b) a heavy chain variable region comprising an amino acid sequence of SEQ ID NO: 4, and a light chain variable region comprising an amino acid sequence of SEQ ID NO: 3;

(c) a heavy chain variable region comprising an amino acid sequence of SEQ ID NO: 6, and a light chain variable region comprising an amino acid sequence of SEQ ID NO: 5; or (d) a heavy chain variable region comprising an amino acid sequence of SEQ ID NO: 8, and a light chain variable region comprising an amino acid sequence of SEQ ID NO: 7; or (e) a heavy chain variable region comprising an amino acid sequence of SEQ ID NO: 10, and a light chain variable region comprising an amino acid sequence of SEQ ID NO: 9.

Table 1B shows heavy and light chain amino acid sequences for humanized IgG mAbs.

TABLE 1B

Heavy and Light Chain Amino Acid Sequences for humanized IgG mAbs.

TPP2009|hIgG|Light_Chain
AQSVLTQDPAVSVALGQTVRITCQGDSLRSYYASWYQQKPGQAPVLVIYG
KNNRPSGIPDRFSGSSSGNTASLTTTGAQAEDEADYYCNSRDSSGNHLVF
GGGTKLTVLGQPKAAPSVTLFPPSSEELQANKATLVCLISDFYPGAVTVA
WKADGSPVKAGVETTKPSKQSNNKYAASSYLSLTPEQWKSHRSYSCQVTH
EGSTVEKTVAPAECS SEQ ID NO: 51

TPP2009|hIgG|Heavy chain
EVQLLESGGGLVQPGGSLRLSCAASGPTFSAYRMGWVRQAPGKGLEWVSR
IYSSGRTRYADSVKGRFTISRDNSKNTLYLQMNSLRAEDTAVYYCAREK
ASDLSGSFSEALDYWGQGTLVTVSSASTKGPSVFPLAPSSKSTSGGTAAL
GCLVKDYPPEPVTVSWNSGALTSGVHTFPAVLQSSGLYSLSSVVTVPSSS
LGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG SEQ ID NO:52

TABLE 1B-continued

Heavy and Light Chain Amino Acid Sequences for humanized IgG mAbs.

TPP-2015|hIgGlight_chain
AQDIQMTQSPGTLSLSPGERATLSCRASQSVSSSYLAWYQQKPGQAPRLL
IYGASSRATGIPDRFSGSGSGTDFTLTISRLEPEDFAVYYCQQYGSSRTF
GQGTKVEIRRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC SEQ ID NO: 53

TPP-2015|hIgG|heavy_chain
EVQLLESGGGLVQPGGSLRLSCAASGFTFSKYKMDWVRQAPGKGLEWVSR
IGPSGGKTMYADSVKGRFTISRDNSKNTLYLQMNSLRAEDTAVYYCAREK
ASDLSGTYSEALDYWGQGTLVTVSSASTKGPSVFPLAPSSKSTSGGrAAL
GCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSG SEQ IDNO: 54

TPP-2016|hIgG|light_chain, Kappa
AQDIQMTQSPATLSVSPGERATLSCRASQNINRNLAWYQQKPGRAPRLLI
HTASTRAPGVPVRITGSGSGTEFTLTISSLEPEDFAVYFCQQYASPPRTF
GQGTKVEIKRTVAAPSVFIFPPSDEQLKSGTASVVCLLNNFYPREAKVQW
KVDNAEQSGNSQESVTEQDSKDSTYSLSSTLTLSKADYEKHKVYACEVTH
QGLSSPVTKSFNRGEC SEQ ID NO: 55

TPP-2016|hIgG|heavy_chain
EVQLLESGGGLVQPGGSLRLSCAASGFTFSKYRMDWVRQAPGKGLEWVSR
IGPSGGKTTYADSVKGRFTISRDNSKNTLYLQMNSLRAEDTAVYYCAREK
TSDLSGSYSEALDYWGQGTLVTVSSASTKGPSVFPLAPSSKSTSGGTAAL
GCLVKDYFPEPVWSWNSGALTSGVHTFPAVLQSSGLYSLSSVVTVPSSSL
GTQTYICNYNHKPSNTKVDKKVEPKSCDKTHTCPPCPAPELLGGPSVFLF
PPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSRDELTKNQVSLTCLVKGFYPSDIAVEWESNGQPBNNYKT
TPPVLDSDGSFFLYSKLTVDKSRWQQGNVFSCSVMHEALHNHYTQKSLSL
SPG SEQ IDNO: 56

TPP-2019|hIgG|light_chain, Kappa
AQDIQMTQSPATLSLSPGERATLSCRASQRVSSSYLTWYQQKPGQAPRLL
IYGASSRATGIPDRFSGSGSGTDFTLTISRLEPEDFAVYYCQQYDSTPPL
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC SEQ ID NO: 57

TPP-2019|hIgG|heavy_chanin
EVQLLESGGGLVQPGGSLRLSCAASGFTSRYAMYWVRQAPGKGLEWVSRI
SPSGGKTHYADSVKGRFTISRDNSKNTLYLQMNSLRAEDTAVYYCARLSQ
TGYYPHYHYYGMDVWGQGTTVTVSSASTKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPG SEQ ID NO: 58

Table 1C—shows TPP2803 IgG2, Germlined and converted to IgG2. TPP2803 IgG2 light chain G2, Lambda, amino acid sequence shown in Table 1C is SEQ ID NO:59 and TPP2803 heavy chain amino acid sequence shown in Table 1C is SEQ ID NO: 60.

TABLE 1C

TPP2803 IgG2, Germlined and converted to IgG2

>TPP-2803|hIgG2|light_chain, lambda
SSELTQDPAVSVALGQTVRITCQGDSLRSYYASWYQQKPGQAPVLVIYGK
NNRPSGIPDRFSGSSSGNTASLTITGAQAEDEADYYCNSRDSSGNHLVFG
GGTKLTVLGQPKAAPSVTLFPPSSEELQANKATLVCLISDFYPGAVTVAW
KADGSPVKAGVETTKPSKQSNNKYAASSYLSLTPEQWKSHRSYSCQVTHE
GSTVEKTVAPAECS SEQ ID NO: 59

TABLE 1C-continued

TPP2803 IgG2, Germlined and converted to IgG2

```
>TPP-2803|hIgG2|heavy_chain
EVQLLESGGGLVQPGGSLRLSCAASGFTFSSYRMSWVRQAPGKGLEWVSR
IYSSGGRTRYADSVKGRFTISRDNSKNTLYLQMNSLRAEDTAVYYCAREK
ASDLSGSFSEALDYWGQGTLVTVSSASTKGPSVFPLAPCSRSTSESTAAL
GCLVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFPPK
PKDTLMISRTPEVTCVVVDVSHEDPEVQFNWYVDGVEVFHNAKTKPREEQ
FNSTFRVVSVLTVVHQDWLNGKEYKCKVSNKGLPAPIEKTISKTKGQPRE
PQVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLSP
G SEQ ID NO: 60
```

Table 2A provides a summary of the SEQ ID NOS: for the CDR regions ("CDR1," "CDR2," and "CDR3") of heavy and light chains of monoclonal antibodies that bind to human ATβH.

TABLE 2A

Sequence Identifiers for CDR Regions of Human Anti-ATβH Antibodies

| Clones | Light Chain Variable Region | | | Heavy Chain Variable Region | | |
|---|---|---|---|---|---|---|
| | CDR1 | CDR2 | CDR3 | CDR1 | CDR2 | CDR3 |
| TPP2009 | 21 | 26 | 31 | 36 | 41 | 46 |
| TPP2015 | 22 | 27 | 32 | 37 | 42 | 47 |
| TPP2016 | 23 | 28 | 33 | 38 | 43 | 48 |
| TPP2019 | 24 | 29 | 34 | 39 | 44 | 49 |
| TPP2803 | 25 | 30 | 35 | 40 | 45 | 50 |

Table 2B provides sequences of the SEQ ID NOS: for the CDR regions ("CDR1," "CDR2," and "CDR3") of heavy and light chains of monoclonal antibodies that bind to human ATβH.

TABLE 2B

Sequences for CDR Regions of Human Anti-ATβH Antibodies

| Clone CDR | Sequence-Identifier | Amino Acid Sequence |
|---|---|---|
| TPP2009 LCDR1 | SEQ IQ NO: 21 | QGDSLRSYYAS |
| TPP2015 LCDR1 | SEQ ID NO: 22 | RASQSVSSSYLA |
| TPP2016 LCDR1 | SEQ ID NO: 23 | RASQNINRNLA |
| TPP2019 LCDR1 | SEQ ID NO: 24 | RASQRVSSSYLT |
| TPP2803 LCDR1 | SEQ ID NO: 25 | QGDSLRSYYAS |
| TPP2009 LCDR2 | SEQ ID NO: 26 | GKNNRPS |
| TPP2015 LCDR2 | SEQ ID NO: 27 | GASSRAT |
| TPP2016 LCDR2 | SEQ ID NO: 28 | TASTRAP |
| TPP2019 LCDR2 | SEQ ID NO: 29 | GASSRAT |
| TPP2803 LCDR2 | SEQ ID NO: 30 | GKNNRPS |
| TPP2009 LCDR3 | SEQ ID NO: 31 | NSRDSSGNHLV |
| TPP2015 LCDR3 | SEQ ID NO: 32 | QQYGSSRT |
| TPP2016 LCDR3 | SEQ ID NO: 33 | QQYASPPRT |
| TPP2019 LCDR3 | SEQ ID NO: 34 | QQYDSTPPLT |
| TPP2803 LCDR3 | SEQ ID NO: 35 | NSRDSSGNHLV |
| TPP2009 HCDR1 | SEQ ID NO: 36 | AYRMG |
| TPP2015 HCDR1 | SEQ ID NO: 37 | KYKMD |
| TPP2016 HCDR1 | SEQ ID NO: 38 | KYRMD |
| TPP2019 HCDR1 | SEQ ID NO: 39 | RYAMY |
| TPP2803 HCDR1 | SEQ ID NO: 40 | SYRMS |
| TPP2009 HCDR2 | SEQ ID NO: 41 | RIYSSGGRTRYADSVKG |
| TPP2015 HCDR2 | SEQ ID NO: 42 | RIGPSGGKTM YADSVKG |
| TPP2016 HCDR2 | SEQ ID NO: 43 | RIGPSGGKTT YADSVKG |
| TPP2019 HCDR2 | SEQ ID NO: 44 | RISPSGGKTH YADSVKG |
| TPP2803 HCDR2 | SEQ ID NO: 45 | RIYSSGGRTR YADSVKG |
| TPP2009 HCDR3 | SEQ ID NO: 46 | AREKASDLSGSFSEALDY |
| TPP2015 HCDR3 | SEQ ID NO: 47 | AREKASDLSG TYSEALDY |
| TPP2016 HCDR3 | SEQ ID NO: 48 | AREKTSDLSG SYSEALDY |
| TPP2019 HCDR3 | SEQ ID NO: 49 | ARLSQTGYYP HYHYYGMDV |
| TPP2803 HCDR3 | SEQ ID NO: 50 | AREKASDLSG SFSEALDY |

In at least some possible embodiments, an isolated monoclonal antibody is provided that binds to human ATβH, wherein the antibody comprises a CDR3 comprising an amino acid sequence of any one of SEQ ID NOS: 46-50. These CDR3s are from a heavy chain of the antibodies identified during panning and screening.

In a further embodiment, this antibody further comprises: (a) a CDR1 comprising an amino acid sequence selected from the group consisting of SEQ ID NOS: 36-40; (b) a CDR2 comprising an amino acid sequence selected from the group consisting of SEQ ID NOS: 41-45; or (c) both a CDR1 comprising an amino acid sequence selected from the group consisting of SEQ ID NOS: 36-40 and a CDR2 comprising an amino acid sequence selected from the group consisting of SEQ ID NOS: 41-45.

In at least some possible embodiments, antibodies share a CDR3 from one of the light chains of the antibodies identified during panning and screening. Thus, also provided is an isolated monoclonal antibody, wherein said antibody binds to ATβH and inhibits anticoagulant activity, wherein said antibody comprises a CDR3 comprising an amino acid sequence selected from the group consisting of SEQ ID NOS: 31-35. In further embodiments, the antibody further comprises (a) a CDR1 comprising an amino acid sequence selected from the group consisting of SEQ ID NOS: 21-25, (b) a CDR2 comprising an amino acid sequence selected from the group consisting of SEQ ID NOS: 26-30, or (c) both a CDR1 comprising an amino acid sequence selected from the group consisting of SEQ ID NOS: 21-25 and a CDR2 comprising an amino acid sequence selected from the group consisting of SEQ ID NOS: 26-30.

In at least some possible embodiments, the antibody comprises a CDR3 from a heavy chain and a light chain of the antibodies identified from screening and panning. Provided is an isolated monoclonal antibody, wherein said antibody binds to ATβH and inhibits anticoagulant activity, wherein said antibody comprises a CDR3 comprising an amino acid sequence selected from the group consisting of SEQ ID NOS: 46-50 and a CDR3 comprising an amino acid sequence selected from the group consisting of SEQ ID NOS: 31-35. In a further embodiment, the antibody further comprises: (a) a CDR1 comprising an amino acid sequence selected from the group consisting of SEQ ID NOS: 36-40; (b) a CDR2 comprising an amino acid sequence selected from the group consisting of SEQ ID NOS: 41-45; (c) a CDR1 comprising an amino acid sequence selected from the group consisting of SEQ ID NOS: 21-25; and/or (d) a CDR2 comprising an amino acid sequence selected from the group consisting of SEQ ID NOs: 26-30.

In some embodiments, the antibody comprises heavy and light chain variable regions comprising:

(a) a light chain variable region comprising an amino acid sequence comprising SEQ ID NOS: 21, 26, and 31 and a heavy chain variable region comprising an amino acid sequence comprising SEQ ID NOS: 36, 41, and 46;
(b) a light chain variable region comprising an amino acid sequence comprising SEQ ID NOS: 22, 27, and 32 and a heavy chain variable region comprising an amino acid sequence comprising SEQ ID NOS: 37, 42, and 47;
(c) a light chain variable region comprising an amino acid sequence comprising SEQ ID NOS: 23, 28, and 33 and a heavy chain variable region comprising an amino acid sequence comprising SEQ ID NOS: 38, 43, and 48;
(d) a light chain variable region comprising an amino acid sequence comprising SEQ ID NOS: 24, 29, and 34 and a heavy chain variable region comprising an amino acid sequence comprising SEQ ID NOS: 39, 44, and 49;
(e) a light chain variable region comprising an amino acid sequence comprising SEQ ID NOS: 25, 30, and 35 and a heavy chain variable region comprising an amino acid sequence comprising SEQ ID NOS: 40, 45, and 50.

Also provided is an isolated monoclonal antibody that binds to AtβH and inhibits anticoagulant activity, wherein said antibody comprises an amino acid sequence having at least about 89%, about 90%, about 91%, about 92%, about 93%, about 94%, about 95%, about 96%, about 97%, about 98%, about 99%, or about 99.5% identity to an amino acid sequence selected from the group consisting of the amino acid sequences set forth in SEQ ID NOS: 1-10.

The antibody can be species specific or can cross react with multiple species. In some embodiments, the antibody can specifically react or cross react with ATβH of human, mouse, rat, rabbit, guinea pig, monkey, pig, dog, cat or other mammalian species.

The antibody can be of any of the various classes of antibodies, such as without limitation an IgG1, an IgG2, an IgG3, an IgG4, an IgM, an IgA1, an IgA2, a secretory IgA, and IgD, and an IgE antibody.

In one embodiment, provided is an isolated fully human monoclonal antibody to human ATIII.

Optimized Variants of Anti-ATβH Antibodies

In some embodiments, the antibodies can be panned, screened and optimized, for example to increase affinity to ATβH, to further decrease any affinity to ATα, to improve cross-reactivity to different species, or to improve blocking activity of ATβH. Such optimization can be performed for example by utilizing site saturation mutagenesis of the CDRs or amino acid residues in close proximity to the CDRs, i.e. about 3 or 4 residues adjacent to the CDRs, of the antibodies.

Also provided are monoclonal antibodies that may have increased or high affinity to ATβH. In some embodiments, the anti-ATβH antibodies may have a binding affinity of at least about $10^8 M^{-1}$, in some other embodiments may have at least about $10^9 M^{-1}$, about $10^{10} M^{-1}$, about $10^{11} M^{-1}$ or greater, e.g., up to about $10^{13} M^{-1}$ or greater.

In some embodiments, additional amino acid modifications can be introduced to reduce divergence from the germ line sequence. In other embodiments, amino acid modifications can be introduced to facilitate antibody production for large scale production processes.

In some embodiments, provided are isolated anti-ATβH monoclonal antibodies that specifically bind to human ATβ, which antibodies may comprise one or more amino acid modifications. In some embodiments, the antibody may comprise about 1, about 2, about 3, about 4, about 5, about 6, about 7, about 8, about 9, about 10, about 11, about 12, about 13, about 14, about 15, about 16, about 17, about 18, about 19, or about 20 or more modifications.

Epitopes

Figure 11B:
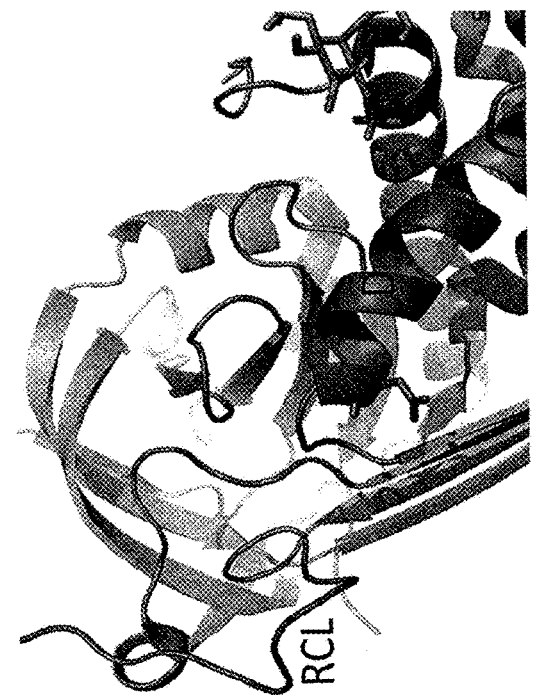
FIGS. 11A and 11B shows a molecular model of the three-dimensional structures of native ATβ complexed with/without heparin (FIG. 11A), and fully activated antibody TPP2009 bound to heparin (FIG. 11B) and its predicted epitope structure. Helix D is extended upon heparin binding B.
Figure 11A:

Also provided is an isolated monoclonal antibody that can bind to a predicted epitope of human ATβH, wherein the epitope comprises one or more of residues from human ATβH as shown in FIG. 11.

In some embodiments, the epitope comprises the N135 site of human ATβH. In other embodiments, the site can comprise part of the amino acid residue sequence of RCL loop of human ATβH.

Also provided are antibodies that can compete with any of the antibodies described herein for binding to human ATβH. For example, such a competing antibody can bind to one or more epitopes described above.

Nucleic Acids, Vectors and Host Cells

Also provided are isolated nucleic acid molecules encoding any of the monoclonal antibodies described herein. Thus, provided is an isolated nucleic acid molecule encoding an antibody that binds to human ATβH. Table 3 shows the nucleotide sequences of some anti-ATβH antibodies.

TABLE 3

Nucleotide sequence of anti-ATβH antibodies.

| | Light Chain | Heavy Chain |
|---|---|---|
| TPP2009 | GCACAGAGCGTCTTG | GAAGTTCAATTGTTAGAGTCTGGTGG |
| | ACTCAGGACCCTGCT | CGGTCTTGTTCAGCCTGGTGGTTCTTT |
| | GTGTCTGTGGCCTTG | ACGTCTTTCTTGCGCTGCTTCCGGATT |
| | GGACAGACAGTCAG | CACTTTCTCTGCTTACCGTATGGGTTG |
| | GATCACATGCCAAGG | GGTTCGCCAAGCTCCTGGTAAAGGTT |
| | AGACAGCCTCAGAA | TGGAGTGGGTTTCTCGTATCTATTCTT |
| | GCTATTATGCAAGCT | CTGGTGGCCGTACTCGTTATGCTGACT |
| | GGTACCAGCAGAAG | CCGTTAAAGGTCGCTTCACTATCTCTA |
| | CCAGGACAGGCCCCT | GAGACAACTCTAAGAATACTCTCTAC |
| | GTACTTGTCATCTAT | TTGCAGATGAACAGCTTAAGGGCTGA |
| | GGTAAAAACAACCG | GGACACGGCCGTGTATTACTGTGCGA |
| | GCCCTCAGGGATCCC | GAGAGAAAGCGTCGGATCTATCGGGG |
| | AGACCGATTCTCTGG | AGTTTTTCTGAGGCCCTTGACTACTGG |
| | CTCCAGCTCAGGAAA | GGCCAGGGAACCCTGGTCACCGTCTC |
| | CACAGCTTCCTTGAC | AAGCGCCTCCACCAAGGGCCCATCGG |
| | CATCACTGGGGCTCA | TCTTCCCGCTAGCACCCAGCAGCAAG |
| | GGCGGAAGATGAGG | AGCACCAGCGGCGGAACAGCCGCCCT |
| | CTGACTATTACTGTA | GGGCTGCCTGGTGAAAGACTACTTCC |

TABLE 3-continued

Nucleotide sequence of anti-ATβH antibodies.

| | Light Chain | Heavy Chain |
|---|---|---|
| | ACTCCCGGGACAGCA GTGGTAACCATCTGG TATTCGGCGGAGGGA CCAAGCTGACCGTCC TAGGTCAGCCCAAGG CTGCCCCCTCGGTCA CTCTGTTCCCGCCCT CCTCTGAGGAGCTTC AAGCCAACAAGGCC ACACTAGTGTGTCTG ATCAGTGACTTCTAC CCGGGAGCTGTGACA GTGGCCTGGAAGGCA GATGGCAGCCCCGTC AAGGCGGGAGTGGA GACCACCAAACCCTC CAAACAGAGCAACA ACAAGTACGCGGCCA GCAGCTACCTGAGCC TGACGCCCGAGCAGT GGAAGTCCCACAGA AGCTACAGCTGCCAG GTCACGCATGAAGGG AGCACCGTGGAGAA GACAGTGGCCCCTGC AGAATGCTCT (SEQ ID NO: 11) | CCGAGCCCGTGACCGTGTCCTGGAAC TCTGGCGCCCTGACCAGCGGAGTGCA TACCTTCCCCGCCGTGCTGCAGAGCA GCGGCCTGTACAGCCTGAGCAGCGTG GTGACAGTGCCCAGCAGCAGCCTGGG AACCCAGACCTACATCTGCAACGTGA ACCACAAGCCCAGCAACACCAAGGTG GACAAGAAGGTGGAACCCAAGAGCT GCGACAAGACCCACACCTGTCCCCCC TGCCCTGCCCCTGAACTGCTGGGCGG ACCCAGCGTGTTCCTGTTCCCCCCAAA GCCCAAGGACACCCTGATGATCAGCC GGACCCCCGAAGTGACCTGCGTGGTG GTGGACGTGTCCCACGAGGACCCAGA AGTGAAGTTTAATTGGTACGTGGACG GCGTGGAAGTGCATAACGCCAAGACC AAGCCCAGAGAGGAACAGTACAACA GCACCTACCGGGTGGTGTCCGTGCTG ACCGTGCTGCACCAGGACTGGCTGAA CGGCAAAGAGTACAAGTGCAAGGTCT CCAACAAGGCCCTGCCTGCCCCCATC GAGAAAACCATCAGCAAGGCCAAGG GCCAGCCCCGCGAGCCTCAGGTGTAC ACACTGCCCCCAGCCGGGATGAGCT GACCAAGAACCAGGTGTCCCTGACCT GTCTGGTGAAAGGCTTCTACCCCAGC GATATCGCCGTGGAATGGGAGAGCAA CGGCCAGCCCGAGAACAATTACAAGA CCACCCCCCCTGTGCTGGACAGCGAC GGCTCATTCTTCCTGTACTCCAAGCTG ACCGTGGACAAGAGCCGGTGGCAGCA GGGCAACGTGTTCAGCTGCAGCGTGA TGCACGAGGCCCTGCACAATCACTAC ACCCAGAAGTCCCTGAGCCTGAGCCC CGGC (SEQ ID NO: 12) |
| TPP2015 | GCACAAGACATCCAG ATGACCCAGTCTCCA GGCACCCTGTCTTTG TCTCCAGGGGAAAGA GCCACCCTCTCCTGC AGGGCCAGTCAGAGT GTTAGCAGCAGCTAC TTAGCCTGGTACCAG CAGAAACCTGGCCAG GCTCCCAGGCTCCTC ATCTATGGTGCATCC AGCAGGGCCACTGGC ATCCCAGACAGGTTC AGTGGCAGTGGGTCT GGGACAGACTTCACT CTCACCATCAGCAGA CGGAGCCTGAAGATT TTGCAGTGTATTACT GTCAGCAGTATGGTA GCTCAACGTTCGGCC AAGGGACCAAGGTG GAAATCAGACGAACT GTGGCTGCAATCTGT CTTCATCTTCCCGCC ATCTGATGAGCAGTT GAAATCTGGAACTGC CTCTGTTGTGTGCCT GCTGAATAACTTCTA TCCCAGAGAGGCCAA AGTACAGTGGAAGGT GGATAACGCCCTCCA ATCGGGTAACTCCCA GGAGAGTGTCACAG AGCAGGACAGCAAG GACAGCACCTACAGC CTCAGCAGCACCCTG ACGCTGAGCAAAGC AGACTACGAGAAAC ACAAAGTCTACGCCT GCGAAGTCACCCATC | GAAGTTCAATTGTTAGAGTCTGGTGG CGGTCTTGTTCAGCCTGGTGGTTCTTT ACGTCTTTCTTGCGCTGCTTCCGGATT CACTTTCTCTAAGTACAAGATGGATTG GGTTCGCCAAGCTCCTGGTAAAGGTT TGGAGTGGGTTTCTCGTATCGGTCCTT CTGGTGGCAAGACTATGTATGCTGAC TCCGTTAAAGGTCGCTTCACTATCTCT AGAGACAACTCTAAGAATACTCTCTA CTTGCAGATGAACAGCTTAAGGGCTG AGGACACGGCCGTGTATTACTGTGCG AGAGAGAAAGCGTCGGATCTATCGGG GACTTATTCTGAGGCCCTTGACTACTG GGGCCAGGGAACCCTGGTCACCGTCT CAAGCGCCTCCACCAAGGGCCCATCG GTCTTCCCGCTAGCACCCAGCAGCAA GAGCACCAGCGGCGGAACAGCCGCCC TGGGCTGCCTGGTGAAGACTACTTC CCCGAGCCCGTGACCGTGTCCTGGAA CTCTGGCGCCCTGACCAGCGGAGTGC ATACCTTCCCCGCCGTGCTGCAGAGC AGCGGCCTGTACAGCCTGAGCAGCGT GGTGACAGTGCCCAGCAGCAGCCTGG GAACCCAGACCTACATCTGCAACGTG AACCACAAGCCCAGCAACACCAAGGT GGACAAGAAGGTGGAACCCAAGAGC TGCGACAAGACCCACACCTGTCCCCC CTGCCCTGCCCCTGAACTGCTGGGCG GACCCAGCGTGTTCCTGTTCCCCCCAA AGCCCAAGGACACCCTGATGATCAGC CGGACCCCCGAAGTGACCTGCGTGGT GGTGGACGTGTCCCACGAGGACCCAG AAGTGAAGTTTAATTGGTACGTGGAC GGCGTGGAAGTGCATAACGCCAAGAC CAAGCCCAGAGAGGAACAGTACAAC AGCACCTACCGGGTGGTGTCCGTGCT GACCGTGCTGCACCAGGACTGGCTGA ACGGCAAAGAGTACAAGTGCAAGGTC TCCAACAAGGCCCTGCCTGCCCCCAT CGAGAAAACCATCAGCAAGGCCAAG |

TABLE 3-continued

Nucleotide sequence of anti-ATβH antibodies.

| | Light Chain | Heavy Chain |
|---|---|---|
| | AGGGCCTGAGCTCGC<br>CCGTCACAAAGAGCT<br>TCAACAGGGGAGAG<br>TGT (SEQ ID NO: 13) | GGCCAGCCCCGCGAGCCTCAGGTGTA<br>CACACTGCCCCCAGCCGGGATGAGC<br>TGACCAAGAACCAGGTGTCCCTGACC<br>TGTCTGGTGAAAGGCTTCTACCCCAG<br>CGATATCGCCGTGGAATGGGAGAGCA<br>ACGGCCAGCCCGAGAACAATTACAAG<br>ACCACCCCCCTGTGCTGGACAGCGA<br>CGGCTCATTCTTCCTGTACTCCAAGCT<br>GACCGTGGACAAGAGCCGGTGGCAGC<br>AGGGCAACGTGTTCAGCTGCAGCGTG<br>ATGCACGAGGCCCTGCACAATCACTA<br>CACCCAGAAGTCCCTGAGCCTGAGCC<br>CCGGC (SEQ ID NO: 14) |
| TPP2016 | GCACAAGACATCCAG<br>ATGACCCAGTCTCCA<br>GCCACCCTGTCTGTG<br>TCTCCAGGGGAAAGA<br>GCCACCCTCTCCTGC<br>AGGGCCAGTCAGAAT<br>ATTAATAGAAACTTG<br>GCCTGGTACCAGCAG<br>AAGCCTGGCCGGGCT<br>CCCAGACTCCTCATC<br>CATACCGCATCCACT<br>AGGGCCCCTGGTGTC<br>CCAGTCAGGATCACT<br>GGCAGTGGGTCTGGA<br>ACAGAGTTCACTCTC<br>ACCATCAGCAGCCTG<br>GAACCTGAAGATTTT<br>GCAGTGTATTTCTGT<br>CAGCAGTATGCTAGC<br>CCACCTCGGACGTTC<br>GGCCAAGGGACCAA<br>GGTGGAAATCAAGC<br>GAACTGTGGCTGCAC<br>CATCTGTCTTCATCTT<br>CCCGCCATCTGATGA<br>GCAGTTGAAATCTGG<br>AACTGCCTCTGTTGT<br>GTGCCTGCTGAATAA<br>CTTCTATCCCAGAGA<br>GGCCAAAGTACAGTG<br>GAAGGTGGATAACG<br>CCCTCCAATCGGGTA<br>ACTCCCAGGAGAGTG<br>TCACAGAGCAGGAC<br>AGCAAGGACAGCAC<br>CTACAGCCTCAGCAG<br>CACCCTGACGCTGAG<br>CAAAGCAGACTACG<br>AGAAACACAAAGTCT<br>ACGCCTGCGAAGTCA<br>CCCATCAGGGCCTGA<br>GCTCGCCCGTCACAA<br>AGAGC<br>TTCAACAGGGGAGA<br>GTGT (SEQ ID NO: 15) | GAAGTTCAATTGTTAGAGTCTGGTGG<br>CGGTCTTGTTCAGCCTGGTGGTTCTTT<br>ACGTCTTTCTTGCGCTGCTTCCGGATT<br>CACTTTCTCTAAGTACCGTATGGATTG<br>GGTTCGCCAAGCTCCTGGTAAAGGTT<br>TGGAGTGGGTTTCTCGTATCGGTCCTT<br>CTGGTGGCAAGACTACTTATGCTGAC<br>TCCGTTAAAGGTCGCTTCACTATCTCT<br>AGAGACAACTCTAAGAATACTCTCTA<br>CTTGCAGATGAACAGCTTAAGGGCTG<br>AGGACACGGCCGTGTATTACTGTGCG<br>AGAGAGAAAACGTCGGATCTATCGGG<br>GAGTTATTCTGAGGCCCTTGACTACTG<br>GGGCCAGGGAACCCTGGTCACCGTCT<br>CAAGCGCCTCCACCAAGGGCCCATCG<br>GTCTTCCCGCTAGCACCCAGCAGCAA<br>GAGCACCAGCGGCGGAACAGCCGCCC<br>TGGGCTGCCTGGTGAAAGACTACTTC<br>CCCGAGCCCGTGACCGTGTCCTGGAA<br>CTCTGGCGCCCTGACCAGCGGAGTGC<br>ATACCTTCCCCGCCGTGCTGCAGAGC<br>AGCGGCCTGTACAGCCTGAGCAGCGT<br>GGTGACAGTGCCCAGCAGCAGCCTGG<br>GAACCCAGACCTACATCTGCAACGTG<br>AACCACAAGCCCAGCAACACCAAGGT<br>GGACAAGAAGGTGGAACCCAAGAGC<br>TGCGACAAGACCCACACCTGTCCCCC<br>CTGCCCTGCCCCTGAACTGCTGGGCG<br>GACCCAGCGTGTTCCTGTTCCCCCCAA<br>AGCCCAAGGACACCCTGATGATCAGC<br>CGGACCCCCGAAGTGACCTGCGTGGT<br>GGTGGACGTGTCCCACGAGGACCCAG<br>AAGTGAAGTTTAATTGGTACGTGGAC<br>GGCGTGGAAGTGCATAACGCCAAGAC<br>CAAGCCCAGAGAGGAACAGTACAAC<br>AGCACCTACCGGGTGGTGTCCGTGCT<br>GACCGTGCTGCACCAGGACTGGCTGA<br>ACGGCAAAGAGTACAAGTGCAAGGTC<br>TCCAACAAGGCCCTGCCTGCCCCCAT<br>CGAGAAAACCATCAGCAAGGCCAAG<br>GGCCAGCCCCGCGAGCCTCAGGTGTA<br>CACACTGCCCCCAGCCGGGATGAGC<br>TGACCAAGAACCAGGTGTCCCTGACC<br>TGTCTGGTGAAAGGCTTCTACCCCAG<br>CGATATCGCCGTGGAATGGGAGAGCA<br>ACGGCCAGCCCGAGAACAATTACAAG<br>ACCACCCCCCTGTGCTGGACAGCGA<br>CGGCTCATTCTTCCTGTACTCCAAGCT<br>GACCGTGGACAAGAGCCGGTGGCAGC<br>AGGGCAACGTGTTCAGCTGCAGCGTG<br>ATGCACGAGGCCCTGCACAATCACTA<br>CACCCAGAAGTCCCTGAGCCTGAGCC<br>CCGGC (SEQ ID NO: 16) |
| TPP2019 | GCACAAGACATCCAG<br>ATGACCCAGTCTCCA<br>GCCACCCTGTCTTTG<br>TCTCCAGGGGAAAGA<br>GCCACCCTCTCCTGC<br>AGGGCCAGTCAGCGT<br>GTTAGCAGCAGCTAC<br>TTAACCTGGTACCAG | GAAGTTCAATTGTTAGAGTCTGGTGG<br>CGGTCTTGTTCAGCCTGGTGGTTCTTT<br>ACGTCTTTCTTGCGCTGCTTCCGGATT<br>CACTTTCTCTCGTTACGCTATGTATTG<br>GGTTCGCCAAGCTCCTGGTAAAGGTT<br>TGGAGTGGGTTTCTCGTATCTCTCCTT<br>CTGGTGGCAAGACTCATTATGCTGAC<br>TCCGTTAAAGGTCGCTTCACTATCTCT |

TABLE 3-continued

Nucleotide sequence of anti-ATβH antibodies.

| | Light Chain | Heavy Chain |
|---|---|---|
| | CAGAAACCTGGCCAG<br>GCTCCCAGGCTCCTC<br>ATCTATGGTGCATCC<br>AGCAGGGCCACTGGC<br>ATCCCAGACAGGTTC<br>AGTGGCAGTGGGTCT<br>GGGACAGACTTCACT<br>CTCACCATCAGCAGA<br>CTGGAGCCTGAAGAT<br>TTTGCAGTTTATTACT<br>GTCAGCAGTATGATA<br>GTACGCCTCCGCTCA<br>CCTTCGGCGGAGGGA<br>CCAAGGTGGAGATCA<br>AACGAACTGTGGCTG<br>CACCATCTGTCTTCA<br>TCTTCCCGCCATCTG<br>ATGAGCAGTTGAAAT<br>CTGGAACTGCCTCTG<br>TTGTGTGCCTGCTGA<br>ATAACTTCTATCCCA<br>GAGAGGCCAAAGTA<br>CAGTGGAAGGTGGAT<br>AACGCCCTCCAATCG<br>GGTAACTCCCAGGAG<br>AGTGTCACAGAGCAG<br>GACAGCAAGGACAG<br>CACCTACAGCCTCAG<br>CAGCACCCTGACGCT<br>GAGCAAAGCAGACT<br>ACGAGAAACACAAA<br>GTCTACGCCTGCGAA<br>GTCACCCATCAGGGC<br>CTGAGCFCGCCCGTC<br>ACAAAGAGCTTCAAC<br>AGGGGAGAGTGT<br>(SEQ ID NO: 17) | AGAGACAACTCTAAGAATACTCTCTA<br>CTTGCAGATGAACAGCTTAAGGGCTG<br>AGGACACGGCCGTGTATTACTGTGCG<br>AGACTGTCTCAAACTGGTTATTACCCT<br>CACTACCACTACTACGGTATGGACGT<br>CTGGGGCCAAGGGACCACGGTCACCG<br>TCTCAAGCGCCTCCACCAAGGGCCCA<br>TCGGTCTTCCCGCTAGCACCCAGCAG<br>CAAGAGCACCAGCGGCGGAACAGCC<br>GCCCTGGGCTGCCTGGTGAAGACTA<br>CTTCCCCGAGCCCGTGACCGTGTCCTG<br>GAACTCTGGCGCCCTGACCAGCGGAG<br>TGCATACCTTCCCGCGTGCTGCAGA<br>GCAGCGGCCTGTACAGCCTGAGCAGC<br>GTGGTGACAGTGCCCAGCAGCAGCCT<br>GGGAACCCAGACCTACATCTGCAACG<br>TGAACCACAAGCCCAGCAACACCAAG<br>GTGGACAAGAAGGTGGAACCCAAGA<br>GCTGCGACAAGACCCACACCTGTCCC<br>CCCTGCCCTGCCCCTGAACTGCTGGGC<br>GGACCCAGCGTGTTCCTGTTCCCCCCA<br>AAGCCCAAGGACACCCTGATGATCAG<br>CCGGACCCCCGAAGTGACCTGCGTGG<br>TGGTGGACGTGTCCCACGAGGACCCA<br>GAAGTGAAGTTTAATTGGTACGTGGA<br>CGGCGTGGAAGTGCATAACGCCAAGA<br>CCAAGCCCAGAGAGGAACAGTACAAC<br>AGCACCTACCGGGTGGTGTCCGTGCT<br>GACCGTGCTGCACCAGGACTGGCTGA<br>ACGGCAAAGAGTACAAGTGCAAGGTC<br>TCCAACAAGGCCCTGCCTGCCCCCAT<br>CGAGAAAACCATCAGCAAGGCCAAG<br>GGCCAGCCCCGCGAGCCTCAGGTGTA<br>CACACTGCCCCCCAGCCGGGATGAGC<br>TGACCAAGAACCAGGTGTCCCTGACC<br>TGTCTGGTGAAAGGCTTCTACCCCAG<br>CGATATCGCCGTGGAATGGGAGAGCA<br>ACGGCCAGCCCGAGAACAATTACAAG<br>ACCACCCCCCTGTGCTGGACAGCGA<br>CGGCTCATTCTTCCTGTACTCCAAGCT<br>GACCGTGGACAAGAGCCGGTGGCAGC<br>AGGGCAACGTGTTCAGCTGCAGCGTG<br>ATGCACGAGGCCCTGCACAATCACTA<br>CACCCAGAAGTCCCTGAGCCTGAGCC<br>CCGGC (SEQ ID NO: 18) |
| TPP2803 | AGCGAATTGACTCAG<br>GACCCTGCTGTGTCT<br>GTGGCCTTGGGACAG<br>ACAGTCAGGATCACA<br>TGCCAAGGAGACAG<br>CCTCAGAAGCTATTA<br>TGCAAGCTGGTACCA<br>GCAGAAGCCAGGAC<br>AGGCCCCTGTACTTG<br>TCATCTATGGTAAAA<br>ACAACCGGCCCTCAG<br>GGATCCCAGACCGAT<br>TCTCTGGCTCCAGCT<br>CAGGAAACACAGCTT<br>CCTTGACCATCACTG<br>GGGCTCAGGCGGAA<br>GATGAGGCTGACTAT<br>TACTGTAACTCCCGG<br>GACAGCAGTGGTAAC<br>CATCTGGTATTCGGC<br>GGAGGGACCAAGCT<br>GACCGTCCTAGGTCA<br>GCCCAAGGCTGCCCC<br>CTCGGTCACTCTGTT<br>CCCGCCCTCCTCTGA<br>GGAGCTTCAAGCCAA<br>CAAGGCCACACTAGT<br>GTGTCTGATCAGTGA<br>CTTCTACCCGGGAGC<br>TGTGACAGTGGCCTG | GAAGTGCAGCTGCTGGAAAGCGGCGG<br>AGGCCTGGTGCAGCCTGGCGUATCTC<br>TGAGACTCTAGCTGTGCCGCCAGCGGC<br>TTCACCTTCAGCAGCTACAGAATGAG<br>CTGGGTGCGCCAGGCCCCTGGCAAGG<br>GACTGGAATGGGTGTCCCGGATCTAC<br>AGCAGCGGCGGCAGAACCAGATACGC<br>CGACAGCGTGAAGGGCCGGTTCACCA<br>TCTCCCGGGACAACAGCAAGAACACC<br>CTGTACCTGCAGATGAACAGCCTGCG<br>GGCCGAGGACACCGCCGTGTACTATT<br>GCGCCAGAGAGAAGGCCAGCGACCTG<br>AGCGGCAGCTTTAGCGAGGCCCTGGA<br>TTATTGGGGCCAGGGCACACTCGTGA<br>CCGTGTCTAGCGCCAGCACAAAGGGC<br>CCCAGCGTGTTCCCTCTGGCCCCTTGT<br>AGCAGAAGCACCAGCGAGTCTACAGC<br>CGCCCTGGGCTGCCTCGTGAAGGACT<br>ACTTTCCCGAGCCCGTGACAGTGTCCT<br>GGAACTCTGGCGCCCTGACAAGCGGC<br>GTGCACACCTTTCCAGCCGTGCTGCA<br>GAGCAGCGGCCTGTACTCTCTGAGCA<br>GCGTCGTGACTGTGCCCAGCAGCAAC<br>TTCGGCACCCAGACCTACACCTGTAA<br>CGTGGACCACAAGCCCAGCAACACCA<br>AGGTGGACAAGACCGTGGAACGGAA<br>GTGCTGCGTGGAATGCCCCCCTTGTCC<br>TGCCCCTCCAGTGGCTGGCCCTTCCGT<br>GTTCCTGTTCCCCCAAAGCCCAAGG<br>ACACCCTGATGATCAGCCGGACCCCG |

TABLE 3-continued

Nucleotide sequence of anti-ATβH antibodies.

| Light Chain | Heavy Chain |
|---|---|
| GAAGGCAGATGGCA GCCCCGTCAAGGCGG GAGTGGAGACCACC AAACCCTCCAAACAG AGCAACAACAAGTA CGCGGCCAGCAGCTA CCTGAGCCTGACGCC CGAGCAGTGGAAGTC CCACAGAAGCTACAG CTGCCAGGTCACGCA TGAAGGGAGCACCGT GGAGAAGACAGTGG CCCCTGCAGAATGCT CT (SEQ ID NO: 19) | AAGTGACCTGCGTGGTGGTGGATGTG TCCCACGAGGACCCCGAGGTGCAGTT CAATTGGTACGTGGACGGCGTGGAAG TGCACAACGCCAAGACCAAGCCCAGA GAGGAACAGTTCAACAGCACCTTCCG GGTGGTGTCCGTGCTGACCGTGGTGC ATCAGGACTGGCTGAACGGCAAAGAG TACAAGTGCAAGGTGTCCAACAAGGG CCTGCCTGCCCCCATCGAGAAAACCA TCAGCAAGACCAAAGGCCAGCCCCGC GAGCCCCAGGTGTACACACTGCCTCC AAGCCGGGAAGAGATGACCAAGAAC CAGGTGTCCCTGACCTGTCTCGTGAA AGGCTTCTACCCCTCCGATATCGCCGT GGAATGUGAGAGCAACGGCCAGCCC GAGAACAACTACAAGACCACCCCCCC CATGCTGGACAGCGCGGCTCATTCTTC CTGTACAGCAAGCTCTACAGTGGACAA GTCCCGGTGGCAGCAGGGCAACGTGT TCAGCTGCAGCGTGATGCACGAAGCC CTGCACAACCACTACACCCAGAAGTC CCTGAGCCTGAGCCCTGGC (SEQ ID NO: 20) |

In some embodiments, isolated nucleic acid molecules encode an antibody that binds to ATβH and inhibits anticoagulant activity but has minimal binding to ATα, wherein the antibody comprises a heavy chain variable region comprising an amino acid sequence selected from the group consisting of SEQ ID NOS: 2, 4, 6, 8, and 10.

In some embodiments, isolated nucleic acid molecules encode an antibody that binds to ATβH and inhibits anticoagulant activity but has minimal binding to ATα, wherein the antibody comprises a light chain variable region comprising an amino acid sequence selected from the group consisting of SEQ ID NOS: 1, 3, 5, 7, and 9.

In other embodiments, isolated nucleic acid molecules encode an antibody that binds to ATβ and inhibits anticoagulant activity of ATβ, wherein the antibody comprises a heavy chain variable region comprising an amino acid sequence selected from the group consisting of SEQ ID NOS: 2, 4, 6, 8, and 10 or a light chain variable region comprising an amino acid sequence selected from the group consisting of SEQ ID NOS: 1, 3, 5, 7, and 9 and one or more amino acid modifications in the heavy chain variable region or light chain variable region.

Further, also provided are vectors comprising the isolated nucleic acid molecules encoding any of the monoclonal antibodies described above and host cells comprising such vectors.

Methods of Preparing Antibodies to ATβH

The monoclonal antibody can be produced recombinantly by expressing a nucleotide sequence encoding the variable regions of the monoclonal antibody according to one of the present embodiments in a host cell. With the aid of an expression vector, a nucleic acid containing the nucleotide sequence can be transfected and expressed in a host cell suitable for the production. Accordingly, an exemplary method for producing a monoclonal antibody that binds with human ATβH can comprise: (a) transfecting a nucleic acid molecule encoding a monoclonal antibody into a host cell; (b) culturing the host cell so to express the monoclonal antibody in the host cell, and (c) optionally isolating and purifying the produced monoclonal antibody, wherein the nucleic acid molecule comprises a nucleotide sequence encoding a monoclonal antibody.

In one example, to express the antibodies, or antibody fragments thereof; DNAs encoding partial or full-length light and heavy chains obtained by standard molecular biology techniques are inserted into expression vectors such that the genes are operatively linked to transcriptional and translational control sequences. In this context, the term "operatively linked" refers to an antibody gene that is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, alternatively, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segments) within the vector and the VL segment is operatively linked to the CL segment within the vector.

Additionally, or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein). In addition to the antibody chain encoding genes, the recombinant expression vectors carry regulatory sequences that control the expression of the antibody chain genes in a host cell. The term "regulatory sequence" includes promoters, enhancers, and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences can depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, non-viral regulatory sequences can be used, such as the ubiquitin promoter or β-globin promoter.

In addition to the antibody chain genes and regulatory sequences, the recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665; and 5,179,017, all by Axel et al.). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" encompasses a wide variety of techniques commonly used for the introduction of exogenous DNA into a prokaryotic or eukaryotic host cell, e.g., electroporation, calcium-phosphate precipitation, DEAE-dextran transfection, and the like. Although it is theoretically possible to express the antibodies in either prokaryotic or eukaryotic host cells, expression of antibodies in eukaryotic cells, including mammalian host cells, is typical because such eukaryotic cells, and in particular mammalian cells, are more likely than prokaryotic cells to assemble and secrete a properly folded and immunologically active antibody. Examples of mammalian host cells for expressing the recombinant antibodies include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells, HKB11 cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods, such as ultrafiltration, size exclusion chromatography, ion exchange chromatography and centrifugation.

Use of Partial Antibody Sequences to Express Intact Antibodies

Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. Sci. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. It is not necessary to obtain the entire DNA sequence of a particular antibody in order to recreate an intact recombinant antibody having binding properties similar to those of the original antibody (see WO 99/45962).

Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, the corresponding germline leader sequence is used for expression constructs. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has advantages such as elimination or inclusion or particular restriction sites, or optimization of particular codons. The nucleotide sequences of heavy and light chain transcripts are used to design an overlapping set of synthetic oligonucleotides to create synthetic V sequences with identical amino acid coding capacities as the natural sequences. The synthetic heavy and light chain sequences can differ from the natural sequences. For example, strings of repeated nucleotide bases are interrupted to facilitate oligonucleotide synthesis and PCR amplification; and optimal translation initiation sites are incorporated according to Kozak's rules (Kozak, 1991, J. Biol. Chem. 266:19867-19870); and restriction sites are engineered upstream or downstream of the translation initiation sites. For both the heavy and light chain variable regions, the optimized coding, and corresponding non-coding, strand sequences are broken down into 30-50 nucleotide sections at approximately the midpoint of the corresponding non-coding oligonucleotide. For each chain, the oligonucleotides can be assembled into overlapping double stranded sets that span segments of 150-400 nucleotides. The pools are then used as templates to produce PCR amplification products of 150-400 nucleotides.

Typically, a single variable region oligonucleotide set will be broken down into two pools which are separately amplified to generate two overlapping PCR products. These overlapping products are then combined by PCR amplification to form the complete variable region. It can also be desirable to include an overlapping fragment of the heavy or light chain constant region in the PCR amplification to generate fragments that can easily be cloned into the expression vector constructs. The reconstructed heavy and light chain variable regions are then combined with cloned promoter, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. In another aspect, the structural features of a human anti-ATβH antibody are used to create structurally related human anti-ATβH antibodies that retain the function of binding to ATβ. For example, one or more CDRs of the specifically identified heavy and light chain regions of the monoclonal antibodies can be combined recombinantly with known human framework regions and CDRs to create additional, recombinantly-engineered, human anti-ATβH antibodies.

Pro-Coagulant Efficacy of Anti-ATβH mAbs

Pro-coagulant efficacy of anti-ATβH mAbs was investigated using various assays.

Table 4 shows pro-coagulant efficacy of Anti-ATβH mAbs TPP2009 and TPP2803 in plasma from various animal species in the FXa-activated clotting assay.

TABLE 4

Pro-coagulant efficacy of TPP2009 and TPP2803 in plasma from various animal species.

| Species | Normal Plasma ($EC_{50}$ nM) | | HEM A Plasma ($EC_{50}$ in nM) | | HEM A Plasma ($EC_{50}$ in nM) |
|---|---|---|---|---|---|
| | 2009 | 2803 | 2009 | 2803 | 2009 |
| | FXa-Activated Clotting Assay | | | | dPT |
| Human | 10.5 | 2.4 | 4.7 | 2.7 | 9.0 |
| Mouse | NDR | ND | ND | ND | NDR |
| Rat | NDR | ND | ND | ND | ND |
| Rabbit | 25.7 | ND | 10.5 | ND | NDR |
| Beagle | NDR | ND | ND | ND | NDR |
| Cyno | 21.5 | ND | 4.3 | ND | 13.9 |

NDR: no dose response,
ND: not determined,
dPT: diluted prothrombin time,
HEM-A: Hemophilia A plasma.

Anti-ATβH mAbs TPP2009 and TPP2803 both exhibited pro-coagulant efficacy in human normal plasma and hemophilia A plasma in the FXa-activated clotting assay. Specifically, TPP2009 exhibited pro-coagulant efficacy in human normal plasma and hemophilia A plasma in the FXa-activated clotting assay with $EC_{50}$'s of 10.5 nM and 4.7 nM, respectively. TPP2803 exhibited pro-coagulant efficacy in human normal plasma and hemophilia A plasma in the FXa-activated clotting assay with $EC_{50}$'s of 2.4 and 2.7 nM, respectively.

Figure 12:
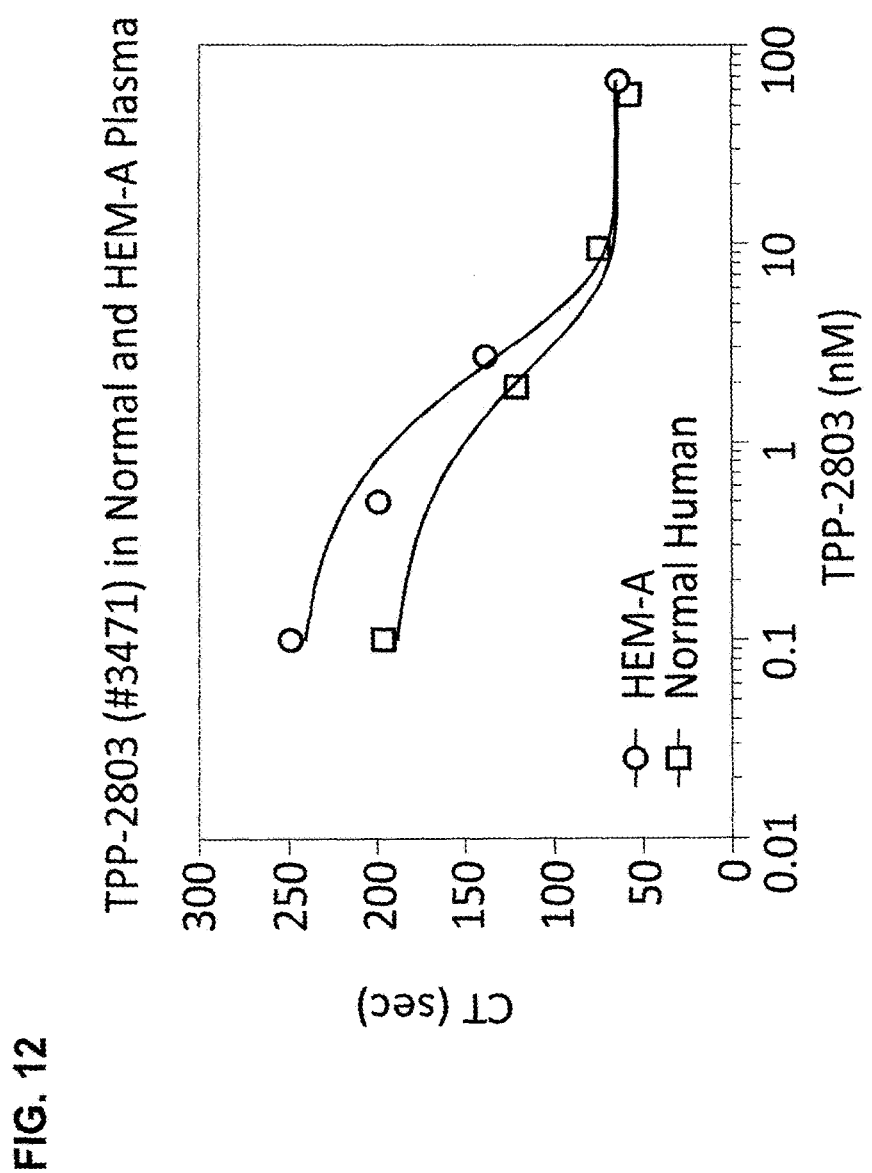
FIG. 12 shows a TPP2803 exhibited dose-dependent shortening of the clotting time in both normal human plasma and hemophilia patient plasma using the FXa activated clotting assay. CT: clotting time, HEM-A: Hemophilia A plasma.

In addition, Anti-ATβH mAb TPP2803 exhibited dose-dependent shortening of the clotting time in both normal human plasma and hemophilia patient plasma using the FXa activated clotting assay, as shown in FIG. 12. CT: clotting time, HEM-A: Hemophilia A plasma.

Figure 13:
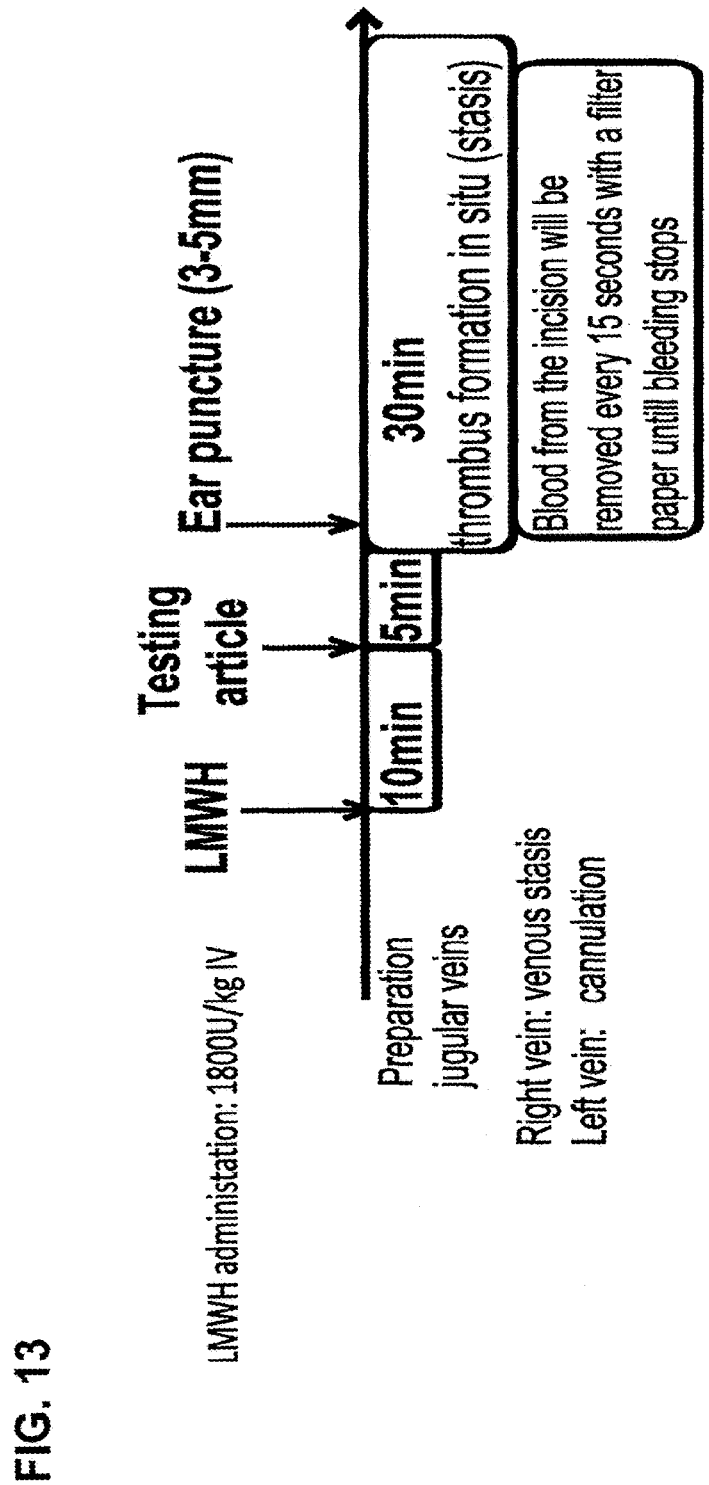
FIG. 13 shows an experimental design of the heparinized rabbit bleeding model; Experimental groups: Vehicle, PBS; Positive control, Protamine sulfate, (28 mg/kg IV); Negative control, M14 IgG2; treatment: 30 mg/kg; TPP2803, 3 mg/kg; TPP2803, 30 mg/kg.
Figure 14:
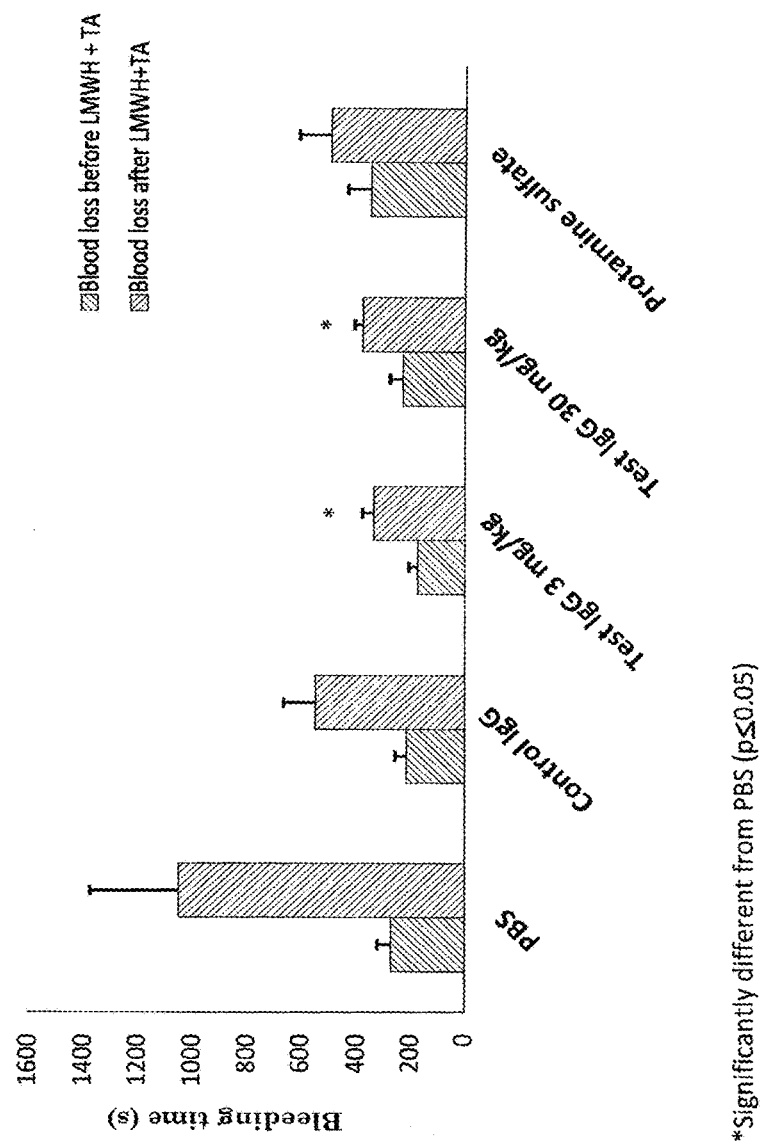
FIG. 14. shows the effect of a control and TPP2803 on bleeding time before and after LMWH and compound administration in a heparinized rabbit bleeding model.
Figure 15:
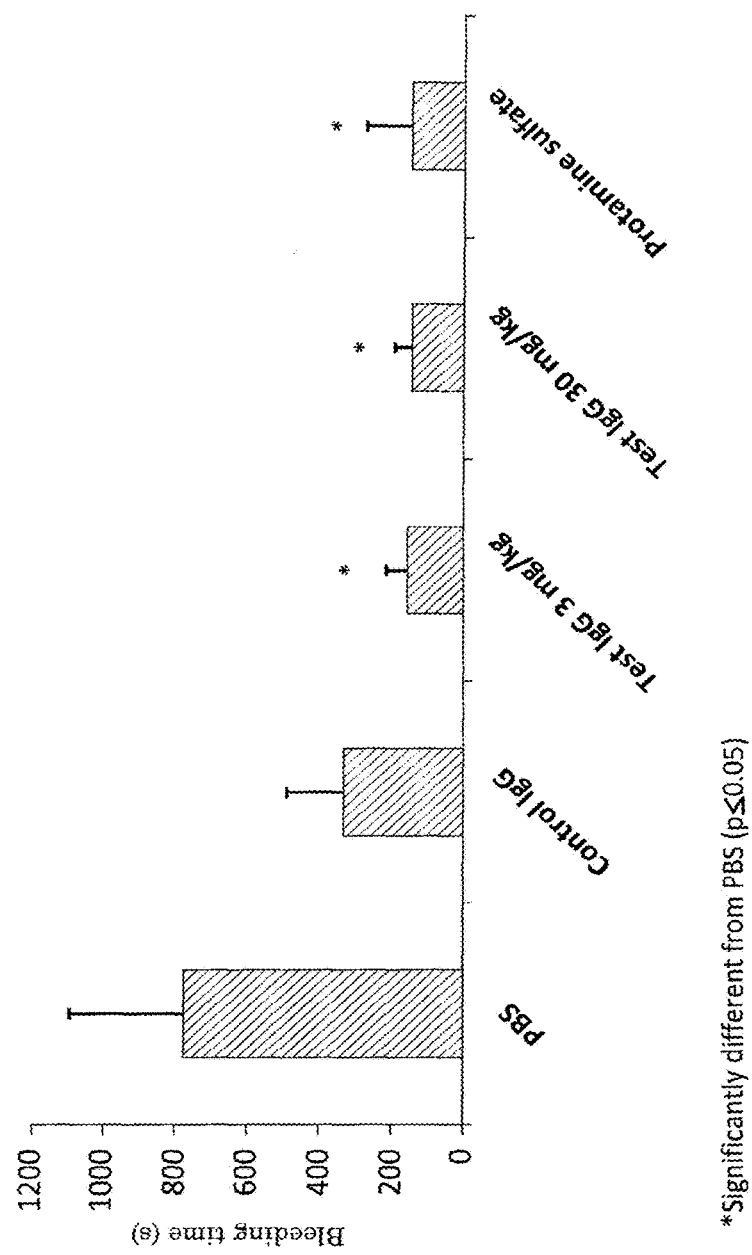
FIG. 15. shows the effect of a control and TPP2803 on delta bleeding time Significantly different from PBS (p≤0.05; T-test).
Figure 16:
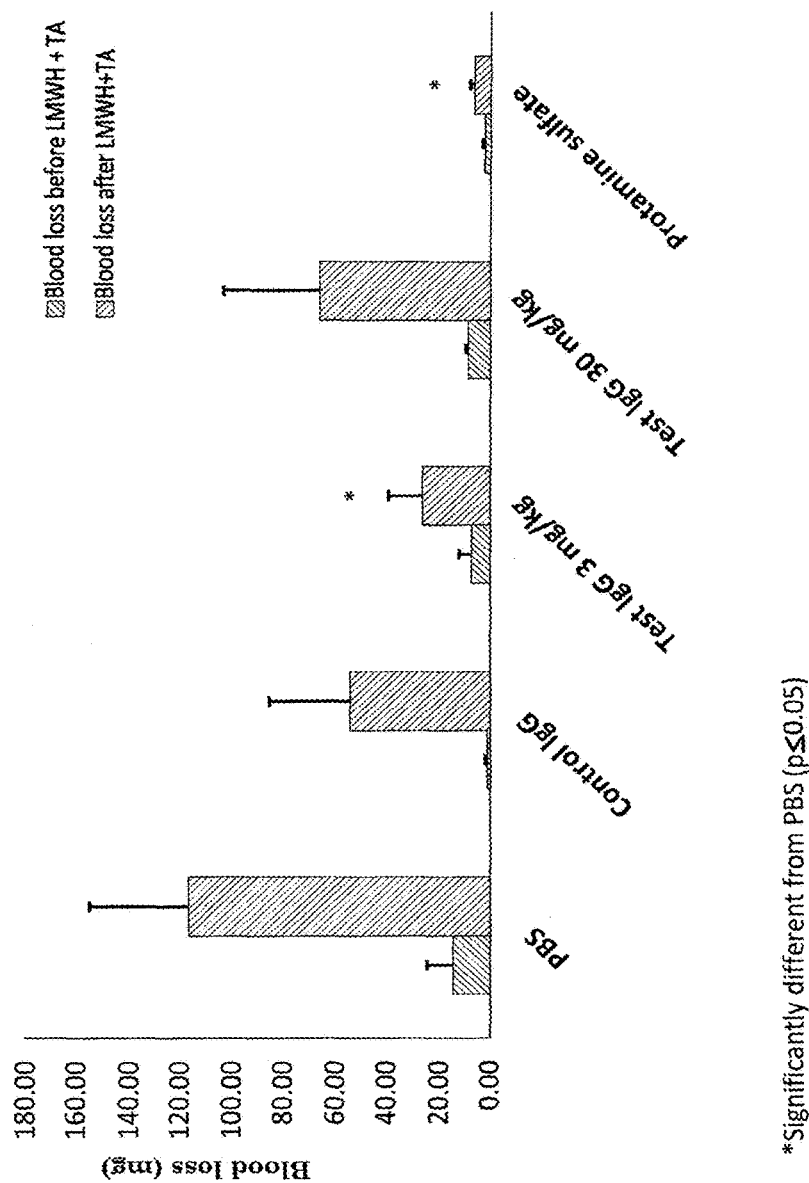
FIG. 16. shows the effect of a control and TPP2803 on blood loss before and after LMWH and antibody administration. (Significance by the T-test).

The heparinized rabbit bleeding model outlined in FIG. 13 was employed to demonstrate in vivo pro-coagulant efficacy of Anti-ATβH mAb TPP2803. The effect of a control and TPP2803 on bleeding time before and after LMWH and compound administration in a heparinized rabbit bleeding model are shown in FIG. 14. Bleeding time after administration of LMWH and Test Article (either 3 mg/kg or 30 mg/kg TPP2803) was significantly reduced compared to bleeding time after LMWH in PBS.Delta bleeding time after administration of either Test Article (either 3 mg/kg or 30 mg/kg TPP2803), or positive control protamine sulfate, was significantly different from PBS ($p \leq 0.05$; * significance by T-test) as shown in FIG. 15. The effect of a control and TPP2803 on blood loss before and after LMWH and antibody administration is shown in FIG. 16. TPP2803 (3 mg/kg) and positive control protamine sulfate both exhibited a significant change in blood loss (*Significance by the T-test) after administration of LMWH.

Pharmaceutical Compositions

Also provided are pharmaceutical compositions comprising therapeutically effective amounts of anti-ATβH monoclonal antibody and a pharmaceutically acceptable carrier. "Pharmaceutically acceptable carrier" as used herein refers to a substance that can be added to the active ingredient to help formulate or stabilize the preparation and causes no significant adverse toxicological effects to the patient. Examples of such carriers are well known to those skilled in the art and include water, sugars such as maltose or sucrose, albumin, salts such as sodium chloride, etc. Other carriers are described for example in Remington's Pharmaceutical Sciences by E. W. Martin. Such compositions will contain a therapeutically effective amount of at least one monoclonal antibody.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. The composition is in some embodiments formulated for parenteral injection. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In some cases, the composition of the carrier includes isotonic agents, for example, sugars, polyalcohols such as mannitol, sorbitol, or sodium chloride.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

Pharmaceutical Uses

The monoclonal antibody can be used for therapeutic purposes for treating genetic and acquired deficiencies or defects in coagulation. For example, the monoclonal antibodies in the embodiments described above can be used to block the interaction of ATβH with its substrate, which can include Factor Xa or Factor IIa. The monoclonal antibodies have therapeutic use in the treatment of disorders of hemostasis such as thrombocytopenia, platelet disorders and bleeding disorders (e.g., hemophilia A, hemophilia B and hemophilia C). Such disorders can be treated by administering a therapeutically effective amount of the anti-ATβH monoclonal antibody to a patient in need thereof. The monoclonal antibodies also have therapeutic use in the treatment of uncontrolled bleeds in indications such as trauma and hemorrhagic stroke. Thus, also provided is a method for shortening the bleeding time comprising administering a therapeutically effective amount of an anti-ATβH monoclonal antibody to a patient in need thereof.

In another embodiment, the anti-ATβH antibody can be useful as an antidote for AT treated patients, including for example wherein AT is used for the treatment of sepsis or bleeding disorder.

The antibodies can be used as monotherapy or in combination with other therapies to address a hemostatic disorder. For example, co-administration of one or more antibodies with a clotting factor such as Factor VIIa, Factor VIII or Factor IX is believed useful for treating hemophilia. In at least some embodiments, a method for treating genetic and acquired deficiencies or defects in coagulation comprises administering: (a) a first amount of a monoclonal antibody that binds to human tissue factor pathway inhibitor; and (b) a second amount of Factor VIII or Factor IX, wherein said first and second amounts together are effective for treating said deficiencies or defects. In at least some embodiments, a method for treating genetic and acquired deficiencies or defects in coagulation comprises administering: (a) a first amount of a monoclonal antibody that binds to human tissue factor pathway inhibitor; and (b) a second amount of factor VIII or Factor IX, wherein said first and second amounts together are effective for treating said deficiencies or defects, and further wherein Factor VII is not co-administered. Also provided is a pharmaceutical composition comprising a therapeutically effective amount of the combination of a monoclonal antibody and Factor VIII or Factor IX, wherein the composition does not contain Factor VII. "Factor VII" includes Factor VII and Factor VIIa. These combination therapies are likely to reduce the necessary infusion frequency of the clotting factor. By co-administration or combination therapy is meant administration of the two therapeutic drugs each formulated separately or formulated together in one composition, and, when formulated separately, administered either at approximately the same time or at different times, but over the same therapeutic period.

In some embodiments, one or more antibodies described herein can be used in combination to address a hemostatic disorder. For example, co-administration of two or more of the antibodies described herein is believed useful for treating hemophilia or other hemostatic disorder.

The pharmaceutical compositions can be parenterally administered to subjects suffering from hemophilia A or B at a dosage and frequency that can vary with the severity of the bleeding episode or, in the case of prophylactic therapy, can vary with the severity of the patient's clotting deficiency.

The compositions can be administered to patients in need as a bolus or by continuous infusion. For example, a bolus administration of an antibody as a Fab fragment can be in an amount from about 0.0025 to about 100 mg/kg body weight, about 0.025 to about 0.25 nag/kg, about 0.010 to about 0.10 mg/kg or about 0.10 to about 0.50 mg/kg. For continuous infusion, an inventive antibody present as an Fab fragment can be administered at about 0.001 to about 100 mg/kg body weight/minute, about 0.0125 to about 1.25 mg/kg/min, about 0.010 to about 0.75 mg/kg/min, about 0.010 to about 1.0 mg/kg/min, or about 0.10 to about 0.50 mg/kg/min for a period of about 1-24 hours, about 1-12 hours, about 2-12 hours, about 6-12 hours, about 2-8 hours, or about 1-2 hours. For administration of an inventive antibody present as a full-length antibody (with full constant regions), dosage amounts can be about 1-10 mg/kg body weight, about 2-8 mg/kg, or about 5-6 mg/kg. Such full-length antibodies would typically be administered by infusion extending for a period of thirty minutes to three hours. The frequency of the administration would depend upon the severity of the condition. Frequency could range from three times per week to once every two weeks to six months.

Additionally, the compositions can be administered to patients via subcutaneous injection. For example, a dose of about 10 to about 100 mg anti-ATβH antibody can be administered to patients via subcutaneous injection weekly, biweekly or monthly. As used herein, "therapeutically effective amount" means an amount of an anti-ATβH monoclonal antibody or of a combination of such antibody and Factor VIII or Factor IX that is needed to effectively increase the clotting time in vivo or otherwise cause a measurable benefit in vivo to a patient in need thereof. The precise amount will depend upon numerous factors, including the components and physical characteristics of the therapeutic composition, intended patient population, individual patient considerations, and the like, and can readily be determined by one skilled in the art.

Aspects of the present disclosure may be further understood in light of the following examples, which should not be construed as limiting the scope of the present teachings in any way.

Example 1—Human and Rabbit ATα and ATβ Purification

ATα and ATβ were purified from human and rabbit plasma by affinity chromatography on heparin-sepharose according to methods previously described (Carlson and Atencio 1982; Peterson and Blackburn 1985) at Enzyme Research laboratory' (South Bend, Ind.). Briefly, the supernatant from a dextran sulphate/calcium chloride precipitation was applied to a heparin-sepharose affinity column (Pharmacia). ATα and ATβ were separated with a NaCl gradient: ATα and ATβ were eluted at 0.8 M and 1.3 M NaCl, respectively. Anion-exchange chromatography (Hi-Trap-Q, Pharmacia) was employed for further purification of ATβ. Purity and glycan profile of ATα and ATβ were evaluated by protein SDS-PAGE and LC-MS.

Example 2—Determination of the Number and Position of Glycans on ATα and ATβ by Mass-Spectrometry Analysis Due to the distinct number of glycans, ATα and ATβ were differentiated based on their mass by Agilent 6520 LC-MS system which is equipped with duo-ESI (or nano ChipCube) source, MassHunter acquisition software and qualitative analysis software including Bioconfirm. Glycosylation sites were determined by a bottom-up method in which proteins are digested by trypsin and Arg-c followed by target MSMS to identify the glycosylated and mono-glycosylated peptide sequences. Data was collected in two experiments: Fragmentor voltage 175v and 430v.

Example 3—AT Antigen Biotinylation

Human and rabbit ATα and ATβ were labeled with biotins on the surface lysine residues by NHS-biotin. For lysine biotinylation, proteins were first desalted into PBS/$Ca^{++}$ buffer (Life Technologies Corporation, Carlsbad, Calif.) to remove any amines that might be inhibitory to the biotinylation reaction. Concentrations of desalted proteins were determined by OD280 on the NanoDrop. Protein were then incubated for 1 hour at room temperature (RT) with Sulfo-NHS-Biotin (Pierce Thermo Scientific, Rockford, Ill.) at the 1:5 and/or 1:3 molar ratio of AT:NHS-biotin (i.e. biotin in excess). Free biotin was removed by overnight dialysis into PBS/$Ca^{++}$ buffer. The amount of biotin in the biotinylated proteins was quantified using Biotin Quantitation Kit (Pierce Thermo Scientific, Rockford, Ill.). Biotinylated ATα and ATβ were analyzed by SDS-PAGE, and biotinylation was confirmed by Western blot analysis using streptavidin-HRP (Pierce Thermo Scientific, Rockford, Ill.) as probe. The functional activities of biotinylated AT were evaluated by FXa inhibition assay. By comparison of the biotinylated ATα and ATβ with unbiotinylated ATα and ATβ, only slight reductions in AT inhibition activity were observed after biotinylation, indicating the biotinylated ATβ and ATα prepared in this way would be representative and could be used in panning for ATβH binders as selective anti-coagulant blockers.

Example 4—Human Monoclonal Antibody Discovery by Phage Display and Panning

A four-arm panning strategy was designed to discover Fabs specifically against ATβH from a human Fab library (Dyax Fab310). The library was first depleted with biotinylated heparin/Fondaparinux-bound ATα and biotinylated ATα and then was panned against heparin/Fondaparinux-bound ATβ and biotinylated ATβ on streptavidin beads, respectively. For each round of panning, the heparin-bound ATα (ATαH) was included in the binding buffer as a competitor. To keep hATβ in active conformation (heparin bound form), heparin was added to the wash buffer in all three rounds of panning. After panning, pooled clones were screened for hATβ and hATβH specific binding and counter-screened for hATα by ELISA. These clones were also examined for differential binding to rabbit ATβ over rabbit ATα. Clones showing differential binding to both hATβH and rATβH over hATα and rATα were further subject to FXa—deinhibition assay with hATβ spike-in. Positive hits (Fabs) were reformatted into IgG1, expressed in HEK293 cells and purified by protein-A column. These purified IgG1s were extensively tested in AT-depleted human plasma and hemA patient plasma for TGA assay (Thrombin Generation Assay) and dPT (diluted Prothrombin Time) assay to measure the clotting time.

Example 5—ELISA (Enzyme-Linked Immunosorbent Assay)

2 ug/ml biotinlyated AT antigens in PBS were coated on Streptavidin Microplates (Greiner, 781997) with or without heparin (50 ug/ml, heparin-Natrium-5000, Apotheke, Fa. Ratiopharm). After overnight antigen coating at 4° C., plates were washed with PBST+/−heparin and blocked with 5% milk in PBST+/−heparin at 37° C. for one hour. After removal of blocking buffer, 20 ug/ml Fab or 4 ug/ml IgG in blocking buffer (5% milk in PBST+/−heparin) was then added to the plates and plates were incubated at room temperature for 1 hour. Plates were then washed three times. Anti-human IgG POD (Sigma, A0170) in blocking buffer was added to plates and plates were incubated at room temperature for 30 minutes. Amplex red (In vitrogen, Cat #A22170) was used for detection at 1:1000 together with $H_2O_2$. After 30 min incubation, plates were read at Ex535, Em 590 in a fluorescent plate reader.

Example 6—FXa De-Inhibition Assay—AT with Heparin

Heparin was incubated with ATβ or ATα to form stable ATβH complexes. Antibody was then added to the ATβH or ATαH complexes. In the meantime, 10 μl of 200 ng/ml FXa (HTI) and 20 μl of 50 μg/ml Fluophen FXa fluorogenic substrate (Hyphen Biomed) were mixed in a separate plate. The antibody-ATβH mixture was added to the FXa/substrate solution quickly and fluorescent kinetic measurement was started immediately at Ex360 nm and Em465 nm. All necessary dilutions is made in 100 mM NaCl, 20 mM Tris, 2.5 mM $CaCl_2$, 0.1% BSA, 0.1% PEG8000.

Example 7—Thrombin Generation Assay (TGA) in FVIII Deficiency Human Plasma

A 1:2 serial dilution of ATβH antibody was made in HemA human plasma starting from 1 uM of final concentration to 0.015 uM. Heparin was added in each antibody solution at a final concentration of 50 nM. An 80 ul of the antibody-heparin-plasma mixture was then added to each well containing 20 ul of reconstitute PPP reagent or calibrator in a 96 well TGA plate. The plate was placed in the TGA instrument and the machine automatically dispensed 20 ul of FluCa (Fluo substrate+$CaCl_2$) into each well. The reaction was allowed to run 60 min. Plasma alone was used as the negative control.

Example 8—Thrombin Generation Assay (TGA) in AT-Depleted Human Plasma with Spiked-in ATα and ATβ Respectively Antibodies were added to human AT-deficient plasma spiked with 15 nm of ATα or ATβ. Heparin was then pipetted into each reaction at a final concentration of 50 nM. 80 ul of plasma samples containing ATH-specific antibody, heparin and ATα or ATβ were added into wells of a 96 well TGA plate with 20 ul of PPP reagent or calibrator. Plates were placed in the TGA instrument, and then 20 ul of FluCa (Fluo substrate+$CaCl_2$) was dispensed into each well. Reactions were allowed to continue for 60 min.

Example 9—Diluted Prothrombin Time Assay (dPT) in Human hemA Plasma and AT Deficient Plasma A serial dilution of anti-ATβH hmAbs was made in hemA plasma starting at 250 nM with 0.1 U/mL of heparin. The mixture of antibody, plasma and heparin was incubated at room temperature for 20-30 min. Then 50 uL of this mixture was added to a 50 uL of diluted Innovin (1/2000) (Dade Behring), incubated for 4 min at 37° C., followed by adding 50 uL of 25 mM CaCl2 (HemSil). dPT test program was set on ACL Top coagulometer with acquisition time of 360 seconds. For dTP in AT deficient plasma, AT-DP was spiked in with either ATα or ATβ at a final concentration of 0.2 uM with 0.1 U/ml of heparin. Anti-ATβH mAbs was added to AT-DP/heparin/ATα or AT-DP/heparin/ATβ mixtures at a final concentration of 0.25 uM and incubated at room temperature for 20-30 min. For each reaction, a 50 uL of plasma/antibody/heparin mixture was added to 50 uL of diluted Innovin (1/4000), incubate 4 min at 37° C., followed by adding 50 uL of 25 mM CaCl2 (HemSil) as above.

Example 10—Antibody Purification

Pre-washed protein A agarose beads were incubated with antibody in binding buffer (volume ratio: 1:1) with rotation overnight at 4° C. Beads were then packed into a column and washed with 1×PBS until O.D.$_{280}$<0.05. Residual solution was drained. Antibodies were eluted with elution buffer and collected into tubes containing neutralizing buffer. Eluted fractions were dialyzed against 1×PBS overnight at 4° C. with at least twice buffer changes. IgG concentration was measured at 280 nm by nanodrop. The antibody purity was examined by either ELISA, SDS-PAGE or SSC.

Example 11—Antibody Binding Affinity Study by Biacore

Antibody affinity measurement was performed on a Biacore T100 or T200 processing unit. Anti-human Fc antibody or streptavidin was immobilized on a CM5 chip. hATβH or biotinylated hmAb antibodies were injected and captured on the chip. ATβ or ATα at different concentration with/without heparin were injected. Only AT and ATH bound to the antibodies generate binding constants. The binding results were reported as Equilibrium Dissociation Constants (KD) in nanoMoles. When AT/heparin complex was analyzed, heparin at 1 uM is included in the running buffer.

Example 12—Heparinized Rabbit Bleeding Model

Experimental design of the heparinized rabbit bleeding model is outlined in FIG. 13. Following preparation of rabbit jugular veins (right vein: venous stasis; left vein: cannulation), low molecular weight heparin (LMWH) is administered to the rabbit (1800 U/kg) IV in PBS vehicle at time 0. After 10 minutes, the test article is administered. Experimental groups include Vehicle, PBS; Positive control, Protamine sulfate, (28 mg/kg IV); Negative control, M14 IgG2; treatment: 30 mg/kg; TPP2803, 3 mg/kg; TPP2803, 30 mg/kg. Five minutes after administration of test article, an ear puncture (3-5 mm) is performed and thrombus formation in situ (stasis) is monitored over a 30 min period. Blood from the incision is removed every 15 seconds with a filter paper until the bleeding stops.

The foregoing disclosure and examples are not intended to narrow the scope of the claims in any way. It should be understood that various modifications and changes can be made, and equivalents can be substituted, to the foregoing embodiments and teachings without departing from the true spirit and scope of the claims appended hereto. The specification and examples are, accordingly, to be regarded in an illustrative sense rather than in a restrictive sense. Furthermore, the disclosure of all articles, books, patent applications, patents, and other material referred to herein are incorporated herein by reference in their entireties.

We claim:

1. A method for treating coagulopathy comprising administering a therapeutically effective amount of a pharmaceutical composition comprising a monoclonal antibody capable of binding the antithrombin (β) heparin complex (ATβH), wherein:
the heavy chain of said antibody comprises: a CDR1 sequence of amino acids 31 to 35 (AYRMG) of SEQ ID NO: 2, a CDR2 sequence of amino acids 50 to 66 (RIYSSGGRTRYADSVKG) of SEQ ID NO: 2, and a CDR3 sequence of amino acids 97 to 114 (AREKASDLSGSFSEALDY) of SEQ ID NO: 2; and
the light chain of said antibody comprises: a CDR1 sequence of amino acids 24 to 34 (QGDSLRSYYAS) of SEQ ID NO: 1, a CDR2 sequence of amino acids 50 to 56 (GKNNRPS) of SEQ ID NO: 1; and a CDR3 sequence of amino acids 89 to 99 (NSRDSSGNHLV) of SEQ ID NO: 1.

2. The method of claim 1, wherein the coagulopathy is hemophilia A, hemophilia B, or hemophilia C.

3. The method of claim 1, wherein the coagulopathy is trauma-induced coagulopathy or severe bleeding.

4. The method of claim 1, further comprising administering a clotting factor.

5. The method of claim 4, wherein the clotting factor is selected from the group consisting of Factor VIIa, Factor VIII, and Factor IX.

6. The method of claim 1, wherein the monoclonal antibody is an IgG1 antibody, an IgG2 antibody, an IgG3 antibody, an IgG4 antibody, an IgM antibody, an IgA1 antibody, an IgA2 antibody, a secretory IgA antibody, an IgD antibody, an IgE antibody, or an antibody fragment.

7. A method for treating coagulopathy comprising administering a therapeutically effective amount of a pharmaceutical composition comprising a monoclonal antibody capable of binding the antithrombin (β) heparin complex (ATβH), wherein:
the heavy chain of said antibody comprises: a CDR1 sequence of amino acids 31 to 35 (KYKMD) of SEQ ID NO: 4, a CDR2 sequence of amino acids 50 to 66 (RIGPSGGKTM YADSVKG) of SEQ ID NO: 4, and a CDR3 sequence of amino acids 97 to 114 (AREKASDLSG TYSEALDY) of SEQ ID NO: 4; and
the light chain of said antibody comprises: a CDR1 sequence of amino acids 26 to 37 (RASQSVSSSYLA) of SEQ ID NO: 3, a CDR2 sequence of amino acids 53 to 59 (GASSRAT) of SEQ ID NO: 3, and a CDR3 sequence of amino acids 92 to 99 (QQYGSSRT) of SEQ ID NO: 3.

8. The method of claim 7, wherein the coagulopathy is hemophilia A, hemophilia B, or hemophilia C.

9. The method of claim 7, wherein the coagulopathy is trauma-induced coagulopathy or severe bleeding.

10. The method of claim 7, further comprising administering a clotting factor.

11. The method of claim 10, wherein the clotting factor is selected from the group consisting of Factor VIIa, Factor VIII, and Factor IX.

12. The method of claim 7, wherein the monoclonal antibody is an IgG1 antibody, an IgG2 antibody, an IgG3 antibody, an IgG4 antibody, an IgM antibody, an IgA1 antibody, an IgA2 antibody, a secretory IgA antibody, an IgD antibody, an IgE antibody, or an antibody fragment.

13. A method for treating coagulopathy comprising administering a therapeutically effective amount of a pharmaceutical composition comprising a monoclonal antibody capable of binding the antithrombin 03) heparin complex (ATβH), wherein:
the heavy chain of said antibody comprises: a CDR1 sequence of amino acids 31 to 35 (KYRMD) of SEQ ID NO: 6, a CDR2 sequence of amino acids 50 to 66 (RIGPSGGKTT YADSVKG) of SEQ ID NO: 6, and a CDR3 sequence of amino acids 97 to 114 (AREKTSDLSG SYSEALDY) of SEQ ID NO: 6; and
the light chain of said antibody comprises: a CDR1 sequence of amino acids 26 to 36 (RASQNINRNLA) of SEQ ID NO: 5, a CDR2 sequence of amino acids 52 to 58 (TASTRAP) of SEQ ID NO: 5, and a CDR3 sequence of amino acids 91 to 99 (QQYASPPRT) of SEQ ID NO: 6.

14. The method of claim 13, wherein the coagulopathy is hemophilia A, hemophilia B, or hemophilia C.

15. The method of claim 13, wherein the coagulopathy is trauma-induced coagulopathy or severe bleeding.

16. The method of claim 13, further comprising administering a clotting factor.

17. The method of claim 16, wherein the clotting factor is selected from the group consisting of Factor VIIa, Factor VIII, and Factor IX.

18. The method of claim 16, wherein the monoclonal antibody is an IgG1 antibody, an IgG2 antibody, an IgG3 antibody, an IgG4 antibody, an IgM antibody, an IgA1 antibody, an IgA2 antibody, a secretory IgA antibody, an IgD antibody, an IgE antibody, or an antibody fragment.

* * * * *